(12) United States Patent
Kawde et al.

(10) Patent No.: US 11,474,067 B2
(45) Date of Patent: Oct. 18, 2022

(54) DETECTION OF SERUM METHIONINE AND GLUCOSE BY GRAPHITE PENCIL ELECTRODE

(71) Applicant: KING FAHD UNIVERSITY OF PETROLEUM AND MINERALS, Dhahran (SA)

(72) Inventors: Abdel-Nasser M. Kawde, Dhahran (SA); Nurudeen Adewale Odewunmi, Dhahran (SA)

(73) Assignee: KING FAHD UNIVERSITY OF PETROLEUM AND MINERALS, Dhahran (SA)

( * ) Notice: Subject to any disclaimer, the term of this patent is extended or adjusted under 35 U.S.C. 154(b) by 569 days.

(21) Appl. No.: 16/182,758

(22) Filed: Nov. 7, 2018

(65) Prior Publication Data

US 2020/0141891 A1    May 7, 2020

(51) Int. Cl.
| | | |
|---|---|---|
| G01N 27/327 | (2006.01) | |
| G01N 27/30 | (2006.01) | |
| G01N 33/66 | (2006.01) | |
| G01N 33/68 | (2006.01) | |
| G01N 27/48 | (2006.01) | |

(52) U.S. Cl.
CPC ....... *G01N 27/3277* (2013.01); *G01N 27/308* (2013.01); *G01N 27/48* (2013.01); *G01N 33/66* (2013.01); *G01N 33/68* (2013.01)

(58) Field of Classification Search
CPC ............ G01N 27/308; G01N 27/3277; G01N 27/3278; G01N 27/48; G01N 33/66; G01N 33/68
See application file for complete search history.

(56) References Cited

U.S. PATENT DOCUMENTS

| | | |
|---|---|---|
| 9,851,325 B2 | 12/2017 | Kawde et al. |
| 2015/0090601 A1 | 4/2015 | Kawde et al. |
| 2017/0082571 A1 | 3/2017 | Kawde et al. |
| 2018/0052134 A1 | 2/2018 | Kawde et al. |

OTHER PUBLICATIONS

W. Zheng, et al., Copper nanoparticles/polyaniline/graphene composite as a highly sensitive electrochemical glucose sensor, Journal of Electroanalytical Chemistry 781 (2016) 155-160 (Year: 2016).*
B. B. Prasad, et al., Multiwalled carbon nanotubes-based pencil graphite electrode modified with an electrosynthesized molecularly imprinted nanofilm for electrochemical sensing of methionine enantiomers, Sensors and Actuators B 176 (2013) 863-874 (Year: 2013).*

(Continued)

*Primary Examiner* — Maris R Kessel
(74) *Attorney, Agent, or Firm* — Oblon, McClelland, Maier & Neustadt, L.L.P.

(57) ABSTRACT

A method of using a graphite electrode to measure a concentration of glucose or methionine from a biological sample is described. A mechanical pencil lead may be used, as the graphite electrode, and the biological sample may come from a patient's serum. The glucose or methionine may produce a peak current response within a range of 0.4-0.8 V when the sample is subjected to linear scan voltammetry.

20 Claims, 24 Drawing Sheets

(56) References Cited

OTHER PUBLICATIONS

Y. Z. Song, et al., Electrochemical Assembling of Methionine—Gold Nanoparticles and Catalysis on the Surface of Glassy Carbon Electrode, Russian Journal of Physical Chemistry A, 2014, vol. 88, No. 13, pp. 2380-2384 (Year: 2014).*

J. Zhang, et al., In situ attachment of cupric oxide nanoparticles to mesoporous carbons for sensitive amperometric non-enzymatic sensing of glucose, Sensors and Actuators B 178 (2013) 125-131 (Year: 2013).*

Sima Pourbeyram, et al., "Nonenzymatic giucose sensor based on disposable pencil graphite electrode modified by copper nanoparticles", Journal of Food and Drug Analysis, vol. 24, 2016, pp. 894-902.

Bhim Ball Prasad, et al., "Electrochemically grown imprinted polybenzidine nanofilm on multiwailed carbon nanotubes anchored pencil graphite fibers for enantioselective micro-solid phase extraction coupled with ultratrace sensing of $_D$- and $_L$-methionine", Journal of Chromatography B, vol. 912, 2013, pp. 65-74.

Özlem Sağlam, et al., "Biosensing of glucose in flow injection analysis system based on glucose oxidase-quantum dot modified pencil graphite electrode", Talanta, vol. 147, 2016, pp. 315-321.

Muamer Dervisevic, et al., "Development of glucose biosensor based on reconstitution of glucose oxidase onto polymeric redox mediator coated pencil graphite electrodes", Enzyme and Microbial Technology, vol. 68, 2014, pp. 69-76.

Ozge Surucu, et al., "Electrochemical and nonenzymatic glucose biosensor based on MDPA/MWNT/PGE nanocomposite", Materials Science and Engineering C, vol. 78, 2017, pp. 539-545.

* cited by examiner

DETECTION OF SERUM METHIONINE AND GLUCOSE BY GRAPHITE PENCIL ELECTRODE

BACKGROUND OF THE INVENTION

Technical Field

The present invention relates to a method of using an in situ modified graphite pencil electrode for the electrochemical measurement of analyte concentrations in aqueous samples.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Diabetes is an infamous clinical ailment that is responsible for disability and death worldwide as a result of alteration of genes and expression of proteins relating to human metabolism. See W. Jin, M. -E. Patti, Genetic determinants and molecular pathways in the pathogenesis of Type 2 diabetes, Clinical Science, 116 (2009) 99-111, incorporated herein by reference in its entirety. Deteriorating health conditions as a result of lifestyle changes brought about by technological advancement in developed nations and poor health systems in under-developed countries have both been linked to diabetes. Healthful management of diabetes necessitates regular monitoring of glucose levels in blood. See L. Guariguata, D. R. Whiting, I Hambleton, J. Beagley, U. Linnenkamp, J. E. Shaw, Global estimates of diabetes prevalence for 2013 and projections for 2035, Diabetes Research and Clinical Practice, 103 (2014) 137-149, incorporated herein by reference in its entirety.

The dominance of enzyme-based glucose biosensors in the global market is due to the superiority of glucose oxidase (GOD) in terms of its essential stability, immobilization property, biocompatibility, and low operating potential. However, its performance is still limited by surrounding humidity, lower temperatures, and pH between 2 and 8 due to its intrinsic protein nature and smaller dynamic range compared with the first two glucose sensing generations. See J. Wang, Electrochemical glucose biosensors, Chemical Reviews, 108 (2008) 814-825; J. Liu, C. Guo. C. M. Li, Y. Li, Q. Chi, X. Huang, L. Liao, T. Yu, Carbon-decorated ZnO nanowire array: A novel platform for direct electrochemistry of enzymes and biosensing applications, Electrochemistry Communications, 11 (2009) 202-205; and Y. Xiao, F. Patolsky, E. Katz, J. F. Hainfeld, I. Willner, Plugging into enzymes: Nanowiring of redox enzymes by a gold nanoparticle, Science, 299 (2003) 1877-1881, each incorporated herein by reference in their entirety.

Efforts such as entrapment of enzymes as a sol-gel, cross linkage of enzymes, wiring of GOD electrochemically, and incorporation of enzymes within a polymer via electropolymerization have been reported to preserve the stability of enzymatic glucose sensors but could only be achieved with a single-use device due to the inability to withstand modifications resulting from chemical and physical processes involved in fabrication. See K. Han, Z. Wu, J. Lee, I. S. Ahn, J. W. Park, B. R. Min, K. Lee, Activity of glucose oxidase entrapped in mesoporous gels, Biochemical Engineering Journal, 22 (2005) 161-166; B. Wu, G. Zhang, S. Shuang, M. M. F. Choi, Biosensors for determination of glucose with glucose oxidase immobilized on an eggshell membrane, Talanta, 64 (2004) 546-553; T. J. Ohara, R. Rajagopalan, A. Heller, "Wired" enzyme electrodes for amperometric determination of glucose or lactate in the presence of interfering substances, Analytical Chemistry, 66 (1994) 2451-2454; and J. Li, X. Lin, Glucose biosensor based on itnnaobilization of glucose oxidase in poly(o-aminophenol) film on polypyrrole-Pt nanocomposite modified glassy carbon electrode, Biosensors and Bioelectronics, 22 (2007) 2898-2905, each incorporated herein by reference in their entirety.

Several transition metals at nanoscale levels have been reported to be effective electro-catalysts for the non-enzymatic detection of glucose. These metals include gold, platinum, nickel, and copper, which have been noted to overcome the challenges of using enzymes in sensor fabrication. See M. A. Beluomini, J. L. da Silva. G. C. Sedenho, N. R. Stradiotto D-mannitol sensor based on molecularly imprinted polymer on electrode modified with reduced graphene oxide decorated with gold nanoparticles, Talanta, 165 (2017) 1-239; N. S. Ismail. Q. H. Le, H. Yoshikawa, M. Saito, E. Tamiya, Development of Non-enzymatic Electrochemical Glucose Sensor Based on Graphene Oxide Nanoribbon—Gold Nanoparticle Hybrid, Electrochimica Acta, 146 (2014) 98-105; D. Feng, F. Wang, Z. Chen, Electrochemical glucose sensor based on one-step construction of gold nanoparticle-chitosan composite film, Sensors and Actuators, B: Chemical, 138 (2009) 539-544; Y. Ma, J. Di, X. Yan, M. Zhao, Z. Lu, Y. Tu, Direct electrodeposition of gold nanoparticles on indium tin oxide surface and its application, Biosensors and Bioelectronics, 24 (2009) 1480-1483; F. Kurniawan, V. Tsakova, V. M. Mirsky, Gold nanoparticles in nonenzymatic electrochemical detection of sugars, Electroanalysis, 18 (2006) 1937-1942; B. K. Jena, C. R. Raj, Enzyme-free amperometric sensing of glucose by using gold nanoparticles, Chemistry—A European Journal, 12 (2006) 2702-2708; A. -N. Kawde, M. A. Aziz, M. El-Zohri, N. Baig, N. Odewumni, Cathodized Gold Nanoparticle-Modified Graphite Pencil Electrode for Non-Enzymatic Sensitive Voltanumetric Detection of Gincose, Electroanalysis, 29 (2017) 1214-1221; Y. Ding, Y. Liu, L. Zhang, Y. Wang, M. Bellagamba, J. Parisi, C. M. Li, Y. Lei, Sensitive and selective nonenzymatic glucose detection using functional NiO-Pt hybrid nanofibers Electrochimica Acta, 58 (2011) 209-214; Q. Shen, L. Jiang, H. Zhang, Q. MM, W. Hou, J. J. Zhu, Three-dimensional dendritic Pt nanostructures: Sonoelectrochemical synthesis and electrochemical applications, Journal of Physical Chemistry C, 112 (2008) 16385-16392; J. Yuan, K. Wang, X. Xia, Highly ordered platinum-nanotubule arrays for amperometric glucose sensing, Advanced Functional Materials, 15 (2005) 803-809; B. Singh, E. Dempsey, C. Dickinson, F. Laffir, Inside/outside Pt nanoparticles decoration of functionalised carbon nanofibers (Pt19.2/f-CNF80.8) for sensitive non-enzymatic electrochemical glucose detection, Analyst, 137 (2012) 1639-1646; J. Zhu, J. Jiang, J. Liu, R. Ding, Y. Li, H. Ding, Y. Feng, G. Wei, X. Huang, CNT-network modified Ni nanostructured arrays for high performance non-enzymatic glucose sensors, RSC Advances, 1 (2011) 1020-1025; T. Watanabe, Y. Einaga, Design and fabrication of nickel microdisk-arrayed diamond electrodes for a non-enzymatic glucose sensor based on control of diffusion profiles, Biosensors and Bioelectronics, 24 (2009) 2684-2689; and X. Zhang, G. Wang, Y. Huang, L. Yu, B. Fang, Non-enzymatic glucose detection using Ni/multi-walled carbon nanotubes composite, Micro and Nano Letters, 7 (2012) 168-170, each incorporated herein by reference in their entirety.

However, copper is one of the most studied of these transition metals for enzyme-free detection of glucose. Electrodes composed of copper nanoparticles modified with a graphene sheet (CuNPs/GS), copper-porous silicon nanocomposite (Cu/PSi), hollow copper (II) oxide (CuO) polyhedron, disposable pencil graphite copper nano-particle (PGE-CuNPs), CuNPs functionalized with phosphorus and molybdenum on glassy carbon (CuNPs-P-M-GC), copper nano-flower (CuNF) modified reduced graphene oxide on flexible paper (CuNF-RGO-FP), carbon clothes composed of different forms (nanowire, nanoparticles and nanosheet) of copper oxides and other copper nanostructures have been reported to be reliable sensors of glucose. See J. Luo, S. Jiang, H. Zhang, t Jiang, X. Liu, A novel non-enzymatic glucose sensor based on Cu nanoparticle modified graphene sheets electrode, Analytica Chimica Acta, 709 (2012) 47-53; A. A. Ensafi, M. M. Abarghoui, B. Rezaei, A new non-enzymatic glucose sensor based on copper/porous nanocomposite, Electrochimica Acta, 123 (2014) 219-226; C. Kong, L. Tang, X. Zhang, S. Sun, S. Yang, X. Song, Z. Yang, Templating synthesis of hollow CuO polyhedron and its application for nonenzymatic glucose detection, Journal of Materials Chemistry A. 2 (2014) 7306-7312; S. Pombeyram, K. Mehdizadeh, Nonenzymatic glucose sensor based on disposable pencil graphite electrode modified by copper nanoparticles, Journal of Food and Drug Analysis, 24 (2016) 894-902; J. Xu, X. Cao, J. Xia, S. Gong, Z. Wang, L. Lu, Phosphomolybdic acid functionalized graphene loading copper nanoparticles modified electrodes for non-enzymatic electrochemical sensing of glucose, Analytica Chimica Acta, 934 (2016) 44-51; B. Wang, Y. Wu, Y. Chen, B. Weng, C. Li, Flexible paper sensor fabricated via in situ growth of Cu nanoflower on RGO sheets towards amperometrically non-enzymatic detection of glucose, Sensors and Actuators B: Chemical, 238 (2017) 802-808; Y. Zhao, J. Zhao, D. Ma, Y. Li, X. Hao, L. Li, C. Yu, L. Zhang, Y. Lu, Z. Wang, Synthesis, growth mechanism of different Cu nanostructures and their application for non-enzymatic glucose sensing, Colloids and Surfaces A: Physicochemical and Engineering Aspects, 409 (2012) 105-111; and Y. Zhong, T. Shi, Z. Liu, S. Cheng, Y. Huang, X. Tao, G. Liao, Z. Tang, Ultrasensitive non-enzymatic glucose sensors based on different copper oxide nanostructures by in-situ growth, Sensors and Actuators B: Chemical, 236 (2016) 326-333, each incorporated herein by reference in their entirety.

Surprisingly, because of the close or similar electro-decomposition potentials of the immobilized compounds (metallic and non-metallic) with the oxidation potential of glucose, most of these non-enzymatic glucose sensors are based on an amperometric measurement technique rather than on other yoltammetric methods. This is because these other voltammetric methods tend to result in multiple, broad, and unresolved peaks, which quickly become more complicated with the complexity of the immobilized compounds on the transducer. These issues may be responsible for the adoption or adaptation of amperometric technique in the existing glucose sensor applications, as these do not distinguish among currents resulting from glucose, potential interferences, and immobilized compounds once a potential is applied.

Graphite Pencil Electrodes (GPE) have been reported as a fascinating electrochemical transducer for various environmental and clinical applications based on cost effectiveness, availability, flexibility, and renewability. See N. Baig, A. -N. Kawde, A cost-effective disposable graphene-modified electrode decorated with alternating layers of Au NPs for the simultaneous detection of dopamine and uric acid in human urine, RSC Advances, 6 (2016) 80756-80765; A.-N. Kawde, N. Baig, M. Sand, Graphite pencil electrodes as electrochemical sensors for environmental analysis: a review of features, developments, and applications, RSC Advances, 6 (2016) 91325-91340; A.-N. Kawde, M. Aziz, N. Baig, Y. Temerk, A facile fabrication of platinum nanoparticle-modified graphite pencil electrode for highly sensitive detection of hydrogen peroxide, Journal of Electroanalytical Chemistry, 740 (2015) 68-74; M. A. Aziz, A.-N. Kawde, Gold nanoparticle-modified graphite pencil electrode for the high-sensitivity detection of hydrazine, Talanta, 115 (2013) 214-221; A. N. Kawde, M. Aziz, Porous Copper-Modified Graphite Pencil Electrode for the Amperometric Detection of 4-Nitrophenol, Electroanalysis, 26 (2014) 2484-2490; and M. Akanda, M. Sohail, M. Aziz, A. N. Kawde, Recent Advances in Nanornaterial-Modified Pencil Graphite Electrodes for Electroanalysis, Electroanalysis, (2015), each incorporated herein by reference in their entirety.

Besides these advantages, the enhancement of GPE's catalytic properties for redox reactions of some species such as glucose allows detection at significantly lower concentrations.

Based on availability, ease of use, and cost-effectiveness, graphite pencil electrodes (CAPE) have also been reported to be efficient electrodes for various electroanalytical sensor applications and possible future sustainable transducers for numerous environmental related laboratory and industrial studies. See A. -N. Kawde, N. Baig, M. Sajid, Graphite pencil electrodes as electrochemical sensors for environmental analysis: A review of features, developments, and applications, RSC Adv. 6 (2016) 91325-91340; N. Baig A.-N. Kawde, A cost-effective disposable graphene-modified electrode decorated with alternating layers of Au NPs for the simultaneous detection of dopamine and uric acid in human urine, RSC Adv. 6 (2016) 80756-80765; A. -N. Kawde, M. Aziz, N. Baig, Y. Temerk, A facile fabrication of platinum nanoparticle-modified graphite pencil electrode for highly sensitive detection of hydrogen peroxide, J. Electroanal. Chem. 740 (2015) 68-74; M. A. Aziz, A. -N. Kawde, Gold nanoparticle-modified graphite pencil electrode for the high-sensitivity detection of hydrazine, Talanta 115 (2013) 214-221; A. -N. Kawde, M. Aziz, Porous Copper-Modified Graphite Pencil Electrode for the Amperometric Detection of 4-Nitrophenol, Electroanal. 26 (2014) 2484-2490; and M. Akanda, M. Sohail, M. Aziz, A. N. Kawde, Recent Advances in Nanomaterial-Modified Pencil Graphite Electrodes for Electroanalysis, Electroanal. 28 (2015) 408-242, each incorporated herein by reference in their entirety.

In order to maximize the potential of GPE for sensing target compounds or elements at trace levels, there is need to enhance the electro-catalytic activity of GPEs. Various forms of silver compounds (AgCs) as an alloy, oxide film, and nanoparticle have been reported as an essential constituent in the fabrication of advanced electrode materials for enhanced electron transfer ability. These advanced electrode materials have been used in devices such as a super capacitor, a transistor for amplifying electrical systems, a semiconductor diode for emitting light, a solar cell, and as a convener of greenhouse gas to a useful product through hydrogen evolution inhibition. See Z. Wu, L. Xie, Y. Xiao, D. Wang, Silver wrapped $MoS_2$ hybrid electrode materials for high-performance supercapacitor, J. Alloys Compd. 708 (2017) 763-768; K. Devarayan, J. Park, H. -Y. Kim, B. -S. Kim, Facile green synthesis of silver nanodendrite/cellulose acetate thin film electrodes for flexible supercapacitors, Carbohydr. Polym. 163 (2017) 153-161; M. Mirzaeian, A. A. Ogwin H. F. Jirandehi, S. Aidarova, Z. Ospanova, N. Tsendzughul. Surface characteristics of silver oxide thin film electrodes for supercapacitor applications. Colloids and Surf., A 519 (2017) 223-230; K. Aoshima, S. Arai, K. Fukuhara, T. Yamada, T. Hasegawa, Surface modification of printed silver electrodes for efficient carrier injection in organic thin-film transistors, Org. Electron. 41 (2017) 137-142; E. Jung, C. Kim, M. Kim, H. Chae, J. H. Cho, S. M. Cho, Roll-to-roll preparation of silver-nanowire transparent electrode and its application to large-area organic light-emitting diodes, Org. Electron. 41 (2017) 190-197; Y. Lee, M. Suh, K. Kim, H. Kim, D. Kim, H. Chang. D. Lee, Y. Kiln, S. W. Kim, D. Y. icon, Conjugated polyelectrolyte-assisted vacuum-free transfer-printing of silver nanowire network for top electrode of polymer light-emitting diodes, Org. Electron. 43 (2017) 64-69; S. Ghasemi, S. R. Hosseini, F. Mousavi, Electrophoretic deposition of graphene nanosheets: A suitable method for fabrication of silver-graphene counter electrode for dye-sensitized solar cell, Colloids and Surf., A 520 (2017) 477-487; and F. Quan, M. Xiong, F. Jia, L. Zhang, Efficient electroreduction of $CO_2$ on bulk silver electrode in aqueous solution via the inhibition of hydrogen evolution, Appl. Surf. Sci. 399 (2017) 48-54, each incorporated herein by reference in their entirety.

Application of Ag electrodes in voltammetric sensor applications is limited based on its characteristic redox peaks but is found to improve the electrocatalytic properties of other electrodes, and is thus used as a modifier in many sensor applications. See Y. Feng, H. Liu, P. Wang. F. Ye, Q. Tan, J. Yang, Enhancing the Electrocatalytic Property of Hollow Structured Platinum Nanoparticles for Methanol Oxidation Through A Hybrid Construction, Sci. Rep. 4 (2014) 6204, incorporated herein by reference in its entirety. A few of these Ag modified electrodes include screen printed electrodes for nitrite detection by a flow injection amperometric technique, voltammetric investigation, and detection of some essential antibiotics by a film made of a Ag-amalgam, a Zinc-AgNPs framework electrode for peroxide detection and an immunosensor film made of AgNPs and graphene oxide. See K. Promsuwan, P. Thavarungkul, P. Kanatharana, W. Limbut, Flow injection amperometric nitrite sensor based on silver microcubics-poly (acrylic acid)/poly (vinyl alcohol) modified 117 screen primed carbon electrode, Electrochim. Acta 232 (2017) 357-369; O. Vajdle, V. Guzsvány, D. Škorić, J. Csartádi, M. Petković, M. Avramov-Ivić, Z. Kónya, S. Petrović, A. Bobrowski, Voltammetric behavior and determination of the macrolide antibiotics azithromycin, clarithromycin and roxithromycin at a renewable silver—amalgam film electrode, Electrochim. Acta 229 (2017) 334-344; P. Arul, S. A. John, Silver nanoparticles built-in zinc metal organic framework modified electrode for the selective non-enzymatic determination of H2O2, Electrochim. Acta 235 (2017) 680-689; and S. X. Lee, H. N. Lim, I. Ibrahim, A. Jamil, A. Pandikumar, N. M. Huang, Horseradish peroxidase-labeled silver/reduced graphene oxide thin film-modified screen-printed electrode for detection of carcinoembryonic antigen, Biosens. Bioelectron. 89, Part 1 (2017) 673-680, each incorporated herein by reference in their entirety.

Methionine is not naturally produced in the body but is abundant in almost all foods consumed by humans (nuts, meat, chicken, cheese, fish, egg, dairy, beans, vegetables etc.). Being a precursor to many essential amino acids (homocysteine, cysteine, taurine, glutathione, glycine, threonine), it has been credited for involvement in many detoxifying processes, protecting cells from pollutants, slowing cell aging, increasing absorption and bio-availability of some macronutrients, aiding excretion, and preventing excess fat build-up. See Oliver D. K. Maddocks, Christiaan F. Labuschagne, Peter D. Adams, Karen H. Vousden, Serine Metabolism Supports the Methionine Cycle and DNA/RNA Methylation through De Novo ATP Synthesis in Cancer Cells. Mol Cell. 61 (2016) 210-221, incorporated herein by reference in its entirety.

The presence of sulphur in a side chain makes redox reaction easy, and was found to help in improving growth of cells, which favors its use as an additive in pharmaceutical products. See W. Srimahaprom, A. E. Flood, Crystal growth rates and optical resolution of dl-methionine hydrochloride by preferential crystallization from aqueous solution, Journal of Crys. Growth 362 (2013) 88-92, incorporated herein by reference in its entirety. High levels of plasma methionine have been found not to have any adverse effect on humans, but may have a role in elevating homocysteine levels in metabolic disorders, especially for non-insulin dependent diabetes (non-cardiovascular disease). See P. J. Garlick. Toxicity of methionine in humans, J. Nutr. 136 (2006) 17225-17255; A. Chico, A. Pérez, A. Córdoba, R. Arcelús, G. Carreras, A. de Leiva, F. González-Sastre. F. Blanco-Vaca, Plasma homocysteine is related to albumin excretion rate in patients with diabetes mellitus: A new link between diabetic nephropathy and cardiovascular disease?, Diabetologia 41 (1998) 684-693; and E. K. Hoogeveen, P. J. Kostense, P. J. Beks, A. J. Mackaay, C. Jakobs, L. M. Bouter, R. J. Heine, C. D. Stehouwer, Hyperhomocysteinemia is associated with an increased risk of cardiovascular disease, especially in noninsulin-dependent diabetes mellitus, Arterioscler Thorn. Vase. Biol. 18 (1998) 133-138, each incorporated herein by reference in their entirety. Folic acid, vitamins C, B-6, and B-12 supplements have been recommended for the moderation of an integral part of the methionine cycle but are not very effective. See M. R. Malinow, A. G. Bostom, R. M. Krauss, Homocyst(e)ine, Diet, and Cardiovascular Diseases, A Statement for Healthcare Professionals From the Nutrition Committee, J Am. Heart Assoc. 99 (1999) 178-182, incorporated herein by reference in its entirety. Emergence of neurological disorder diseases such as Alzheimer, long-term central nervous disorder disease (Parkinson) and many other reduced oxygen species related diseases associated with residual methionine. See D. A. Butterfield, A. I. Bush, Alzheimer's amyloid β-peptide (1-42): Involvement of methionine residue 35 in the oxidative stress and neurotoxicity properties of this peptide, Neurobiol. Aging 25 (2004) 563-568; D.A. Butterfield, J. KartsId, Methionine residue 35 is critical for the oxidative stress and neurotoxic properties of Alzheimer's amyloid β-peptide 1-42, Peptides 23 (2002) 1299-1309; C. Schoneich, Redox processes of methionine relevant to β-amyloid oxidation and Alzheimer's disease, Arch. Biochem. Biophys. 397 (2002) 370-376; and C. B. Glaser, G. Yamin, V. N. Uversky, A. L. Fink, Methionine oxidation, α-synuclein and Parkinson's disease, BBA. Proteins and Proteomics 1703 (2005) 157-169. each>incorporated herein by reference in their entirety. Methionine restriction diet (MRD) is a recent potent treatment or preventative for some chronic health conditions including cancer, depression, insulin sensitivity, and insulin resistance. MRDs have been reported to improve renal insulin in aged kidney, improve glucose tolerance, decrease fasting glucose, lead to the remodeling of white adipose tissue, and reverse liver malfunctioning in mice. See L. Grant, E. K. Lees, L. A. Forney, N. Mody, T. Ge P. A. J. Brown, H. M. Wilson, M. Delibegovic, Methionine restriction improves renal insulin signalling in aged kidneys, Mech. Ageing Dev. 157 (2016) 35-43; and E. K. Lees, E. Krol, L. Grant, K. Shearer, C. Wyse, E. Moncur, A. S. Bykowska, N. Mody, T. W. Gettys, M. Delibegovic, Methionine restriction restores a younger metabolic phenotype in adult mice with alterations in fibroblast growth factor 21, Aging Cell 13 (2014) 817-827, each incorporated herein by reference in their entirety. MRD is not limited to mitigation of diabetes mellitus but has been attributed to prevention of cancer cell growth and life span extension hypothesis strategy in animals and humans. See E. Cellarier, X. Durando, M. P. Vasson, M. C. Farges, A. Demiden, J. C. Maurizis, J. C. Madelmont, P. Chollet, Methionine dependency and cancer treatment, Cancer Treat. Rev. 29 (2003) 489-499; and P. Cavuoto, M. F. Fenech, A review of methionine dependency and the role of methionine restriction in cancer growth control and life-span extension, Cancer Treat. Rev. 38 (2012) 726-736, each incorporated herein by reference in their entirety. All these consequences of methionine are concerns for effective detection of methionine in body plasma.

Due to the complex nature of methionine, there is a need for its separation from other sulphur-containing compounds before it can be quantified or reliably detected. Low sensitivity, longer analysis time, and cost effectiveness have been a challenge for the sustainability of rugged chromatographic, flow analysis, and colorimetric techniques developed for its routine analysis. See K. Borowczyk, G. Chwatko, P. Kubalczyk, H. Jakubowski, J. Kubalska, R. Glowacki, Simultaneous Determination of Methionine and Homocysteine by on-column derivatization with o-phaldialdehyde, Talanta 161 (2016) 917-924; Y. Jiang, B. Mistretta, S. Elsea, Q. Sun, Simultaneous determination of plasma total homocysteine and methionine by liquid chromatography-tandem as spectrometry, Olin, Chim. Acta 464 (2017) 93-97; Z. Deáková, Z. Ďuračlová, D. W. Armstrona, J. Lehotay, Two-dimensional high performance liquid chromatography for determination of homocysteine, methionine, and cysteine enantiomers in human serum, J. Chromatogr., A 1408 (2015) 118-124; M. Zhou, A. Wang, C. Li, X. Luo, Y. Ma, Flow-based determination of methionine in pharmaceutical formulations exploiting TGA-capped CdTe quantum dots for enhancing the luminol-KIO4 chemiluminescence, J. Lumin. 183 (2017) 206-211; and L. Kuang, L. Zhang, A. -Z. Xu, Z. -M. Li, R. -P. Liang, J. -D. Qiu, Bio-dots assembly-induced aggregation of gold nanoparticles for highly sensitive and selective colorimetric detection of methionine, Sens. Actuators, B 244 (2017) 1031-1036, each incorporated herein by reference in their entirety.

Expensive, delicate, and tediously modified electrodes such as electropolymerized film of non-peripheral copper-amine complex, composite nanotubes comprising Pt and $TiO_2$ on glassy carbon electrode ($TiO_2$-Pt/CNT/GCE), nanofilm electrochemically synthesized by molecular imprint on graphite pencil electrode (MWCNT-NFMIP/GPE), aminic nicotine gold nanoparticle, oxygen electrochemically controlled graphene oxide, acrylic acid complexed ZnO modified carbon paste, carbon ceramics electrode (CCE) modified with nickel powder prepared by sol-gel methods and a bimetallic nanoparticle comprising silver and gold on GCE (Au—Ag/GCE) have been reported. See A. J. Jeevagan, S. A. John, Electrochemical determination of L-methionine using the electropolymerized film of non-peripheral amine substituted Cu(II) phthalocyanine on glassy carbon electrode, Bioelectrochem. 85 (2012) 50-55; F. Chekin, S. Bagheri, S. B. Abd Hamid, Synthesis of Pt doped $TiO_2$ nanoparticles: Characterization and application for electrocatalytic oxidation of l-methionine, Sens. Actuators, B 177 (2013) 898-903; B. B. Prasad, I. Pandey, A. Srivastava, D. Kumar, M. P. Tiwari, Multiwalled carbon nanotubes-based pencil graphite electrode modified with an electrosynthesized molecularly imprinted nanofilm for electrochemical sensing of methionine enantiomers, Sens. Actuators, B, 176 (2013) 863-874: K. A. Rawat, S. K. Kailasa, 4-Amino nicotinic acid mediated synthesis of gold nanoparticles for visual detection of arginine, histidine, methionine and tryptophan, Sens. Actuators, B 222 (2016) 780-789; D. Zhang, C. Xu, S. Li, R. Zhang, H. Yan, H. Miao, Y. Fan, B. Yuan, Electrochemically controlling oxygen functional groups in graphene oxide for the optimization in the electro-catalytic oxidation of dihydroxybenzene isomers and L-methionine, J. Electroanal. Chem. 717-718 (2014) 219-224; E. Molaakbari, A. Mostafavi, H. Beitollahi, Simultaneous electrochemical determination of dopamine, melatonin, methionine and caffeine, Sens. Actuators, B 208 (2015) 195-203; A. Salimi, M. Roushani, Electrocatalytic Oxidation of Sulfur Containing Amino Acids at Renewable Ni-Powder Doped Carbon Ceramic Electrode: Application to Amperometric Detection L-Cystine, L-Cysteine and L-Methionine, Electroanal. 18 (2006) 2129-2136; and M. Murugavelu, B. Karthikeyan, Synthesis, characterization of Ag—Au core-shell bimetal nanoparticles and its application for electrocatalytic oxidation/sensing of I-methionine, Mater. Sci. Eng., C 70 Part 1 (2017) 656-664, each incorporated herein by reference in their entirety. However, there is a need for the development of a simple, cost effective, proficient and efficient electroanalytical method for electroanalytical determination of methionine.

Thus, the present work is also aimed at developing a facile electroanalytical technique utilizing in-situ GPE modification with $AgNO_3$ solution for determination of methionine and/or glucose, and for the fabrication of a cost effective, prompt, and ease-to-use electrochemical sensor.

In view of the foregoing, one objective of the present invention is to provide a method for using an unmodified graphite electrode for measuring glucose and methionine concentrations in an aqueous biological sample.

BRIEF SUMMARY OF THE INVENTION

According to a first aspect, the present disclosure relates to a method of measuring a concentration of an analyte in an aqueous sample. This method involves the steps of immersing a graphite electrode, a reference electrode, and a counter electrode in the aqueous sample, and measuring a current response at a voltage of 0.4-0.8 V. The concentration is determined by comparing the current response to a correlation chart. The analyte is glucose or methionine at a concentration of 1.0 µM-10.0 mM, and the aqueous sample comprises an inorganic base at a concentration of 0.02-1.0 M and a metal salt at a concentration of 0.1-10 ppm. The metal salt comprises at least one metal ion selected from the group consisting of $Cu^{2+}$, $Ag^+$, $Ni^{2+}$, $Co^{2+}$, $Co^{3+}$, $Zn^{2+}$, $Sn^{2+}$, $Pb^{2+}$, $Fe^{2+}$, $Fe^{3+}$, $Cr^{2+}$, and $Cr^{3+}$.

In one embodiment, the inorganic base is NaOH, and the aqueous sample has a pH of 12.0 14.0.

In one embodiment, the graphite electrode has no surface modification prior to the immersing.

In one embodiment, the graphite electrode has a diameter or width of 0.1-2.0 mm and a length of 3.0-20.0 mm in contact with the aqueous sample after the immersing.

In one embodiment, the aqueous sample further comprises at least one selected from the group consisting of ascorbic acid, alanine, fructose, uric acid, and cysteine, each independently at a concentration of 0.01-1.00 mM.

In one embodiment, the reference electrode is an Ag/AgCl electrode, and the counter electrode comprises platinum.

In one embodiment, the method further comprises removing a precipitated protein from the aqueous sample prior to the immersing, wherein the aqueous solution further comprises serum.

In a further embodiment, the removing involves mixing an alcohol with a serum at a volume ratio of 1:4-4:1 to produce a precipitated protein and then centrifuging the precipitated protein.

In a further embodiment, where the aqueous solution further comprises serum, the serum is derived from a human donor.

In one embodiment, the measuring involves applying cyclic voltammetry to the aqueous sample.

In one embodiment, the measuring further involves constructing a calibration curve from a current response of two or more standard solutions.

In one embodiment, the analyte is glucose, and the metal salt comprises $Cu^{2+}$. The $Cu^{2+}$ has a concentration of 1-5 ppm in the aqueous sample.

In a further embodiment, the glucose is present in the aqueous sample at a concentration of 0.06-4.0 mM.

In a further embodiment, the voltage is 0.60-0.65 V.

In a further embodiment, the metal salt is $Cu(NO_3)_2$.

In one embodiment, the analyte is methionine, and the metal salt comprises $Ag^+$. The $Ag^+$ has a concentration of 2-6 ppm in the aqueous sample.

In a further embodiment, the methionine is present in the aqueous sample at a concentration of 0.01-0.50 mM.

In a further embodiment, the voltage is 0.63-0.67 V.

In a further embodiment, the metal salt is $AgNO_3$.

In a further embodiment, the measuring produces silver oxide nanoparticles on the graphite electrode.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1:
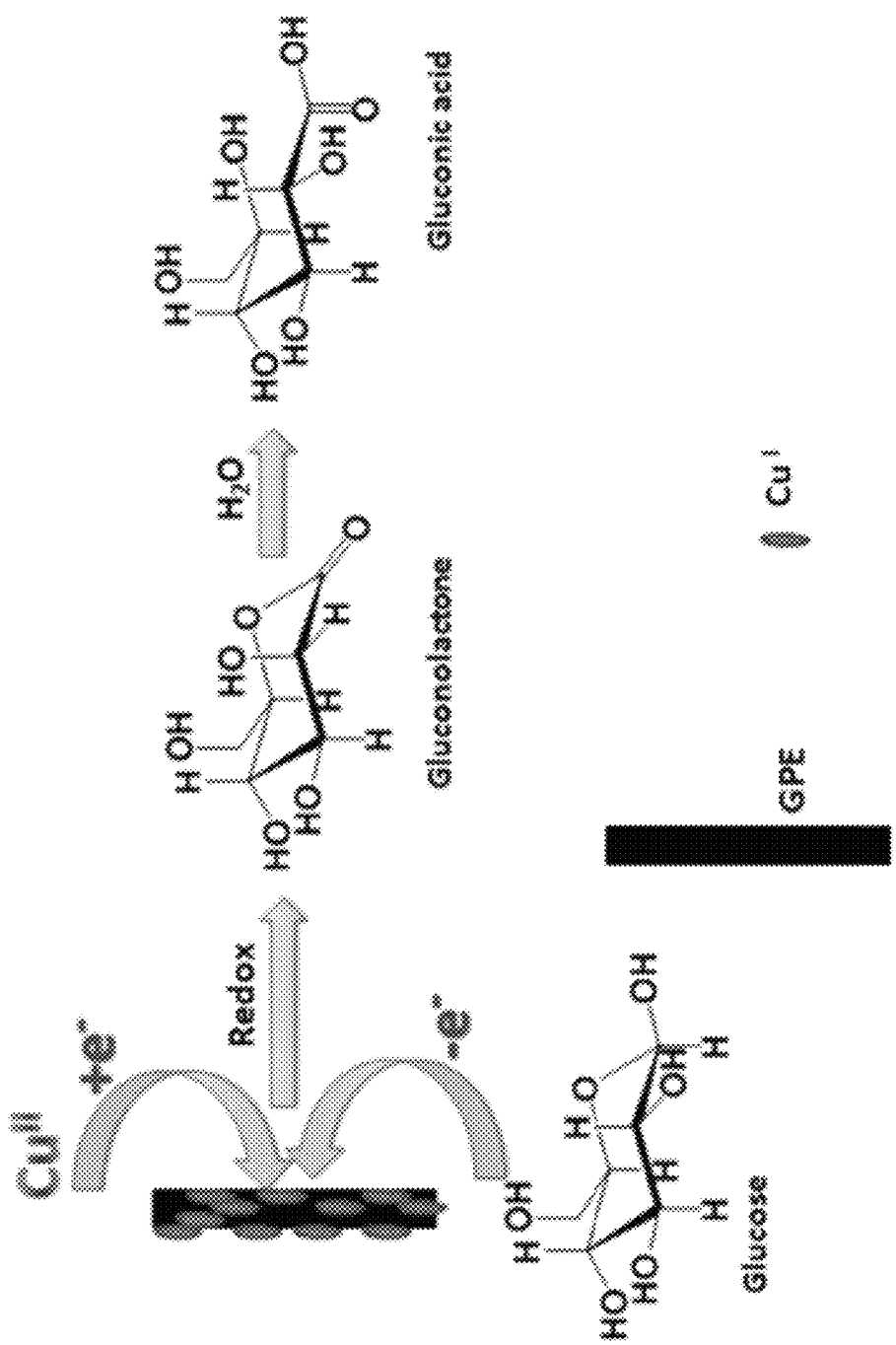
FIG. 1 is a schematic of a redox reaction occurring during the method of measuring a concentration of glucose.

Embodiments of the present disclosure will now be described more fully hereinafter with reference to the accompanying drawings, in which some, but not all embodiments of the disclosure are shown.

The present disclosure will be better understood with reference to the following definitions. As used herein, the words "a" and "an" and the like carry the meaning of "one or more." Within the description of this disclosure, where a numerical limit or range is stated, the endpoints are included unless stated otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the words "about," "approximately," or "substantially similar" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), +/−15% of the stated value (or range of values), or +/−20% of the stated value (or range of values). Within the, description of this disclosure, where a numerical limit or range is stated, the endpoints are included unless stated otherwise. Also, all values and subranges within a numerical limit or range are specifically included as if explicitly written out.

As used herein, "compound" is intended to refer to a chemical entity, whether as a solid, liquid, or gas, and whether in a crude mixture or isolated and purified.

As used herein, "composite" refers to a combination of two or more distinct constituent materials into one. The individual components, on an atomic level, remain separate and distinct within the finished structure. The materials may have different physical or chemical properties, that when combined, produce a material with characteristics different from the original components. In some embodiments, a composite may have at least two constituent materials that comprise the same empirical formula but are distinguished by different densities, crystal phases, or a lack of a crystal phase (i.e. an amorphous phase).

In addition, the present disclosure is intended to include all isotopes of atoms occurring in the present compounds and complexes. Isotopes include those atoms having the same atomic number but different mass numbers. By way of general example, and without limitation, isotopes of hydrogen include deuterium and tritium. Isotopes of carbon include $^{13}C$ and $^{14}C$. Isotopes of silver include $^{107}Ag$ and $^{108}Ag$. Isotopes of copper include $^{63}Cu$ and $^{64}Cu$. Isotopically-labeled compounds of the disclosure may generally be prepared by conventional techniques known to those skilled in the art or by processes analogous to those described herein, using an appropriate isotopically-labeled reagent place of the non-labeled reagent otherwise employed.

According to a first aspect, the present disclosure relates to a method of measuring a concentration of an analyte in an aqueous sample. This method involves the steps of immersing a graphite electrode, a reference electrode, and a counter electrode in the aqueous sample, and measuring a current response at a Voltage of 0.4-0.8 V preferably 0-5 0.7, more preferably 0.60-0.68 V.

As used herein, the term "analyte" refers to a substance that is (or whose chemical constituents are) being identified, detected, and/or measured by the modified graphite electrode. An analyte may be a component of a fluid (e.g., vapor liquid) sample in which the graphite electrode is immersed. Exemplary analytes include, without limitation, biologically important catecholamines (tetrachlorohydroquinone, caffeic acid, rutin, p,p'-bisphenol, 3,4-dihydroxyphenylacetic acid, 3,4-di-t-butylcatechol, hydroquinone, catechol, isoproterenol, 3,4 -dihydroxyephedrine, epinephrine, 3,4-dihydroxybenzyl amine, dopamine, norepinephrine, 2,5-dihydroxybenzene-p-disulfonic acid), analytes of environmental interest, such as picric acid, 2,4-dinitrophenol, plunavin, triflalin, 4-amino-2-nitrophenol, p-nitrophenol, p-nitroaniline, alkylphenols (4-methylthiophenol, 4-methylthio-o-cresol, carbofuran phenol, 2,3,6-trimethylphenol, 2,4-dimethylphenol, 2,3,5-trimethylphenol, 3,5-di-t-butylphenol, 4-ethylphenol, 2-methylphenol, 2-isopropylphenol, phenol, terbutalin, and 3,5-dimethylphenol), and chlorophenols (2-benzyl-4-chlorophenol, 2,4,6-trichlorophenol, 2,3,4,6-tetrachlorophenol, 4-chloro-3,5-dimethylphenol, pentachlorophenol, 2,4-dichlorophenol, 2-chlorophenol 4-chlorophenol, 2,4,5-trichlorophenol, 2,5-dichlorophenol, and 3-chlorophenol), biologically important analytes (glucose, lactate, oxygen, glutamate, choline, phosphate, acetylcholine, dioxybutyrate, homocysteine, D-cysteine, creatine, creatinine, sucrose, fructose, nitric oxide, galactose, arsenite, cholesterol, fructosamine, bilirubin, glycine, methionine, L-citrulline, phosphatidic acid, lysophosphatidic acid, arachidonic acid, asy-minetric dimethylarginine, 1,3-diaminopropane, 21-deoxycortisol, aminoadipic acid, D-2-hydroxyglutaric acid, L-2-hydroxyglutaric acid, aminoadipic acid, 2-hydroxyadipic acid, oxoadipic acid, oxoglutaric acid, 7-hydroxyprogesterone, 3-hydroxyisovaleric acid, 3-hydroxymethylglutaric acid, 3-inethylcrotonylglycine, 3-methylglutaconic acid, adipic acid, ammonia, methylglutaric acid (S)-3-hydroxyisobutyric acid, 3-hydroxyisovaleric acid, 3-methylcrownylglycine, 3-hydroxyisovaleric acid, pyruvic acid, (S)-3,4-dihydroxybutyric acid, pyroglutamic acid, ganglioside GM3, glucosylceramide, lactosylceramide, tetrahexosylceramide, trihexosylceramide, 2-hydroxyestradiol, 2-hydroxyestrone, 20-hydroxyeicosatetraenoic acid, 5-acetylamino-6-amino-3-methyluracil, alpha-N-phenylacetyl-L-glutamine, androstenedione, benzoic acid, bromide, cadaverine, cholic acid, coproporphyrin I, coproporphyrin III, deoxycholic acid, deoxycytidine, DHEA sulfate, DL-homocystine, estradiol, estriol, estrone, estrone sulfate, fluorine, glycocholic acid, guanine, hexanal hydroxyphenyllactic acid, iodide, L-aspartic acid, L-cysteine, L-glutamine, L-lactic acid, L-malic acid, L-methionine, malondialdehyde, myoinositol hexakisphosphate, N-acetylaspartylglutamic acid, orotidine, progesterone, salicyluric acid, selenomethionine, thymine, uric acid, vanilpyruvic acid, cortisol, anabasine, cotinine, hydroxycotinine, L(-)-nicotine pestanal nornicotine, heptacarboxylporphyrin 1, enkephalin L, 24-hydroxycholesterol, 27-hydroxycholesterol, deoxyadenosine, 1 -methyladenine, succinyladenosine, hexacosanoic acid, phytanic acid, pristanic acid, L-pipecolic acid, erucic acid, 7C-aglycone, 5C-aglycone, (R)-salsolinol, alpha-carotene. 5-methyltetrahydrofolic acid, butyric acid, mannitol neopterin, quinolinic acid, 2-butanol, acetone, butanone, ethanol, isopropyl alcohol, methanol, acetaldehyde, nicotinic acid, pantothenic acid, riboflavin, scyllitol, thiamine, honmogentisic acid, aminoadipic acid, L-histidine, 1,5-anhydrosorbitol, 1-methylhistidine, 3,4-dihydroxybenzeneacetic acid, 3-methylhistidine, 4-hydroxy-L-proline, 4-hydroxynonenal, 5-hydroxylysine, 8-hydroxyguanine, 8-hydroxyguanosine, anserine, camosine, citrulline, epsilon-(ganlilla-glutamyl)-lysine, folic acid, fumaric acid, galactitol, ganlilla-aminobutyric acid, glycerophosphocho line, glycylproline, hydroxyproline, L-2,4-diaminobutyric acid, L-alpha-aminobutyric acid, L-arabitol, L-arginine, L-asparagine, L-cystathionine, L-DOPA, L-glutamic acid, L-isoleucine, L-leucine, L-lysine, L-phenylalanine, L-proline, L-serine, L-threonine, L-tryptophan, methylmalonic acid, myoinositol, ornithine, pentosidine, phosphorylcholine, prolylhydroxyproline, ribitol, sorbitol, succinic acid, thiamine monophosphate, thiamine pyrophosphate, estriol-3-sulfate-16-glucuronide, estriol-3-glucuronide, acetylglycine, N-acetylserine, L-thyronine, prostaglandin E2, kynurenic acid, 24,25-dihydroxyvitamin D, 25,26-dihydroxyvitamin D, 25-hydroxyvitamin D2, calcidiol, ergocalciferol, vitamin D3, 11-dehydro-thromboxane B2, 5a-tetrahydrocortisol, ethylmalonic acid, FAD, flavin mononucleotide, glutaric acid, isovalerylglycine, liothyronine, suberic acid, tetrahydrocortisone, thyroxine, 3-hydroxybutyric acid, acetoacetic acid, isocitric acid, L-glutamic acid, L-malic acid, oxalacetic acid, indolcacetic acid, argininosuccinic acid, uracil, 3-methoxytyrosine, 5-mydroxyindoleacetic acid, homovanillic acid, N-acetyl-L-tyrosine, N-acetylvanilalanine, vanillylmandelic acid, vanyiglycol, taurocyamine, aspartylglycosamine 1,3,7-trimethyluric acid, 1,3-dimethyluric acid, 1,7-dimethyluric acid, 1-methylxanthine, 11b-PGF2a, 3-chlorotyrosine, 3-methylxanfhine, 5-HETE, 7-methylxanththe, caffeine, paraxanthine, theobromine, theophylline, iodotyrosine, dimethyl-L-arginine, 13S- hydroxyoctadecadienoic acid, symmetric dimethyl arginine, androstanediol, trans-trans-muconic acid, 2-methyl-3-hydroxybutyric acid, 2-methylacetoacetic acid, tiglylglycine, acetaminophen glueuronide, ubiquinol, dihydrothymine, urcidoisobutyric acid, chenodeoxycholic acid, chenodeoxycholic acid glycine conjugate, hyaluronic acid, taurochenodesoxycholic acid, taurocholic acid, 1b,3a,12a-trihydroxy-5b-cholanoic acid, hyocholic acid, hyodeoxycholic acid, ursodeoxycholic acid, isoursodeoxycholic acid, lithocholic acid, ursocholic acid, 2-methylcitric acid, 3-methyl-crotonylglycine, hydroxypropionic acid, 2-pyrrolidinone, dimethyl amine, 8-isoprostane, ascorbic acid, glutathione, o-phosphoethanolamine, 3,5-diiodothyronine, 1,3-diaminopropane, 1-methylguanosine, 16a-hydroxyestrone, enterodiol, enterolactone, N1-acetylspermidine, N8-acetylspermidine, perillic acid, perillyl alcohol, ribothymidine, xanthosine, testosterone, 1-methyluric acid, 3-methyladenine, citric acid, cytidine, hypoxanthine, inosine, N-acetyl-L-aspartic acid, orotic acid, oxidized glutathione, pseudouridine, thymidine, uridine, xanthine, 1 -methylinosine, 16a-hydroxydehydroisoandrosterone, 5a-tetrahydrocorticosterone, alpha-linolenic acid, alpha-tocopherol, B-carotene, beta-cortol, docosaltexaenoic acid, docosapentaenoic acid, gama-tocopherol, linoleic acid, lycopene, putrescine, tetrahydrodeoxycorticosterone, tetrahydrodeoxycortisol, vitamin A, L-fucose, prostaglandin F2a, leukotriene B4, 6-ketoprostaglandin Fla, sebacic acid, butyrylcarnitine, decanoylcamitine, dodecanoylcamitine, isovalerylcarnitine, L-hexanoylcarnitine, L-octanoyicarnitine, L-palmitoylcarnitine, lactulose, propionylcamitine, stearoylcarnitine, tiglylcarnitine, dihydrouracil, 5-alpha-cholestanol, lathosterol, 1-methyladenosine, 3,5-diiodo-L-tyrosine, betaine, cyclic AMP, guanidine, guanidinosuccinic acid, guanidoacetic acid, methyl guanidine, picolinic acid, 2,3-butanediol, 2-hydroxyphenethylamine, 2-oxoarginine, 4-guanidinobutanoic acid, 7a-hydroxycholesterol, argininic acid, cholesterol sulfate, homo-L-arginine, methanethiol, p-octopamine, propylene glycol, sulfolithocholylglycine, tyramine, urea, L-kynurenine, beta-leucine, cob(I)alamin, inosinic acid, 16-a-hydroxypregnenolone, pyridinoline, histamine, lipoxin A4, hydrogen peroxide, thromboxane A2, D-xylose, 19-hydroxyandrost-4-ene-3,17-dione, glyceric acid, L-a-glutamyl-L-lysine, corticosterone, cortisone, 1-methylhistamine, (R)-3-hydroxybutyric acid, (R)-3-hydroxyisobutyric acid, (S)-3-hydroxyrsobutyric acid, 1-butanol, 4-heptanone, D-Lactic acid, glycerol, hyaluronan, L-carnitine, pyruvaldehyde, S-adenosylmethionine, hydrogen carbonate, ureidopropionic acid, beta-alanine, cartel; cortolone, leukotriene C4, leukotriene E4, adenosine triphosphate, ADP, guanosine diphosphate, guanosine triphosphate, p-hydroxyphenylacetic acid, taurine, 2-methylbutyrylglycine, isobutyrylglycine, methylsuccinic acid, N-butyrylglycine, epitestosterone, thyroxine sulfate, etiocholanolone, diphenhydramine, 3-hydroxydodecanoic acid, diadenosine hexaphosphate, diadenosine pentaphosphate, diadenosine tetraphosphate, diadenosine triphosphate, xanthurenic acid, cyanocobalamin, pyridoxine, hydrogen sulfide, thiosulfate, aldosterone 18-glucuronide, p-synephrine, m-tyramine, serotonin, 1-naphtliol, 2-naphthol, retinol ester, 2-pyrocatechuic acid, gentisic acid, dopamine glucuronide, isomaltose, melanin, N2,N2-dimethylguanosnie, phenylacetic acid, trimethylamine N-oxide), and mixtures thereof.

In one embodiment, the analyte is glucose or methionine at a concentration of 1.0 µM-10.0 mM, and the aqueous sample comprises an inorganic base at a concentration of 0.02-1.0 M and a metal salt at a concentration of 0.1-10 ppm.

In one embodiment, the analyte is glucose and is present in the aqueous sample at a concentration of 0.06-4.0 mM, preferably 0.1-3.5 mM, more preferably 0.5-2.5 mM, though in some embodiments, the glucose may be present at a concentration of less than 0.06 mM or greater than 4.0 mM.

In ogre embodiment, the analyte is methionine and is present in the aqueous sample at a concentration of 0.01-0.50 mM, preferably 0.05-0.35 mM, more preferably 0.08-0.25 mM, though in some embodiments, the methionine may be present at a concentration of less than 0.01 mM or greater than 0.50 mM.

As mentioned above, the aqueous sample comprises a metal salt. The metal salt may have a concentration of 0.1-10 ppm, preferably 0.5-8 ppm, more preferably 2-5 ppm, though may have a concentration of less than 0.1 ppm or greater than 10 ppm. Here, ppm is considered equivalent to a mass of a solute in milligrams (mg), per liter (L) solution: mg/L. The metal salt may comprise at least one metal ion selected from the group consisting of $Cu^{2+}$, $Ag^+$, $Ni^{2+}$, $Co^{2+}$, $Co^{3+}$, $Zn^{2+}$, $Sn^{2+}$, $Pb^{2+}$, $Fe^{2+}$, $Fe^{3+}$, $Cr^{2+}$, and $Cr^{3+}$. Preferably the metal salt comprises $Cu^{2+}$, $Ag^+$, $Ni^{2+}$, $Co^{2+}$, $Zn^{2+}$, $Sn^{2+}$, $Pb^{2+}$, $Fe^{2+}$, $Fe^{3+}$, $Cr^{2+}$, and/or $Cr^{3+}$, more preferably $Cu^{2+}$, $Ag^+$, $Ni^{2+}$, $Co^{2+}$, $Zn^{2+}$, and/or $Sn^{2+}$, even more preferably $Cu^{2+}$ and/or $Ag^+$. The counter ion of the metal salt may be $SO_4^{2-}$, $Br^-$, $NO_3^-$, $OH^-$, $Cl^-$, acetate, or some other anion.

In one embodiment, the metal salt comprises $Ag^+$, and the $Ag^+$ has a concentration in the aqueous sample of 2-6 ppm, preferably 2-5 ppm, more preferably 2.5-4.0 ppm, or about 3.0 ppm. In some embodiments, the $Ag^+$ may have a concentration of less than 2 ppm (for instance, 1 ppm) or greater than 6 ppm (for instance, 10 or 100 ppm). In one embodiment, the metal salt is $AgNO_3$.

In one embodiment, the metal salt comprises $Cu^{2+}$. The $Cu_{2+}$ has a concentration of 1-5 ppm in the aqueous sample, preferably 1.5-4 ppm, more preferably 2-3 ppm, or about 2 ppm. However, in other embodiments, the $Cu^{2+}$ may be present at a concentration of less is than 1 ppm or greater than 5 ppm, for instance, 10 or 100 ppm. In one embodiment, the metal salt is $Cu(NO_3)_2$.

In a preferred embodiment, where the analyte is methionine, the metal salt comprises $Ag^+$, and where the analyte is glucose, the metal salt comprises $Cu^{2+}$.

In one embodiment, the inorganic base may be NaOH, KOH, LiOH, $Mg(OH)_2$, $Ca(OH)_2$, $Ba(OH)_2$, $NH_4OH$, or some other inorganic base. In alternative embodiments, an organic base may be used, such as sodium carbonate or sodium acetate. The inorganic base may have a concentration of 0.02-1.0 M, preferably 0.05-0.8 M, more preferably 0.08-0.5 M, though in some embodiments, the concentration may be less than 0.02 M or greater than 1.0 M. Preferably, the inorganic base is NaOH. In other embodiments, other bases may be used, such as sodium acetate or potassium carbonate. In one embodiment, the aqueous sample has a pH of 12.0-14.0, preferably 12.5-13.9, more preferably 13.0-13.8, or about 13.7. However, in some embodiments, the aqueous sample may have a pH lower than 12.0, such as a pH of 8.0-12.0, 9.0-11.5, or 9.5-11.0.

In one embodiment, the graphite electrode has a diameter or width in contact with the aqueous sample after the immersing of 0.1-2.0 mm, preferably 0.3-1.1 mm, more preferably 0.4-0.7 mm, or about 0.5 mm. The graphite electrode has a length of 3.0-20.0 mm, preferably 4.0-15.0 mm, more preferably 5.0-10.0 mm, or about 7.00 mm, in contact with the aqueous sample after the immersing. However, in some embodiments, the diameter or width may be less than 0.1 mm or greater than 2.0 mm, and in other embodiments, the to length may be less than 3.0 mm or greater than 20.0 mm. The graphite electrode may have a surface area of 5-50 $mm^2$, preferably 6-40 $mm^2$, more preferably 7-20 $mm^2$, or about 11.4 $mm^2$, in contact with the aqueous sample. However, in some embodiments the graphite electrode may have a surface area of less than 5 $mm^2$ or greater than 50 $mm^2$ in contact with the aqueous sample.

Preferably the graphite electrode has the shape of a cylinder; however, other elongated forms of graphite with various cross-sections (such as ellipses, squares, rectangles, hexagons, or irregular shapes) may be used as the graphite electrode. in some embodiments, the graphite electrode may consist of graphite, or comprise at least 99 wt % graphite, preferably at least 99.9 wt % graphite. In another embodiment, the graphite electrode may consist of carbon, or comprise at least 99 wt % carbon, preferably at least 99.9 wt % carbon, more preferably at least 99.99 wt % carbon. In one embodiment, the graphite may be considered an amorphous graphite, or one in which crystalline flakes of graphite are pressed together, where the crystalline flakes have an average longest dimension of 0.2-200 µm, preferably 1-100 µm, more preferably 3-50 µm. These crystalline flakes may be flat, plate-like particles with hexagonal edges, and comprise individual layers of graphene.

In one embodiment, the graphite electrode has a shape similar to a pencil lead (for instance, a mechanical pencil lead). In a preferred embodiment, the graphite electrode may be obtained as a mechanical pencil lead. In an alternative embodiment, the graphite electrode may be of the type used in a wooden pencil. The pencil lead for the graphite electrode may be of type 6H, HB, F, B, 2B, or 4H, however, other hardness es may be used successfully. A mechanical pencil lead being ed for a graphite electrode may comprise clay or wax as binding materials. For instance, a mechanical pencil lead may further comprise 40-95 wt %, graphite, preferably 50-90 wt % graphite, more preferably 65-60 wt % graphite, 1-55 wt % clay, preferably 3-40 wt % clay, more preferably 10-20 wt % clay, and 0-8 wt % wax, preferably 2-7 wt % wax, each relative to a total weight of the mechanical pencil lead. The graphite in a mechanical pencil lead may be amorphous or powdered graphite that is held together by the clay and/or wax binders. The graphite may be made from beneficiated graphite, milled graphite, intercalated graphite, a graphite intercalation compound, such as $MC_8$ (M=K, Rb and Cs) and $M'C_6$ (M'=Li', $Sr^{2+}$, $Ba^{2+}$, $Eu^{2+}$, $Yb^{3+}$, and $Ca^{2+}$), graphite bisulfate, halogen-graphite compounds, and mixtures thereof.

In another embodiment, the graphite electrode may comprise some other type of binder, such as a conductive polymer (polypyrrole, for instance).

Preferably, the graphite electrode has no surface modification prior to the immersing, preferably immediately prior to the immersing. Here, upon immersing and before applying a potential, the graphite electrode surface is in direct contact with the aqueous solution and its solutes. Where the graphite electrode is obtained as a mechanical pencil lead, preferably no surface treatment was performed As defined here, surface modification refers to adsorbing molecules onto the surface of the graphite electrode or chemically reacting the surface of the graphite electrode. Surface modification by this definition does not include changing the physical surface morphology, for instance, by polishing, sanding, nicking, or reshaping the graphite surface, as long as graphite remains.

In an alternative embodiment, other forms of carbon may be used for the electrode, in addition to or in place of graphite. For instance, glassy carbon, carbon black, pyrolytic carbon, carbon paste, or activated charcoal may be used. Other carbon allotropes such tis carbon nanotubes or graphene sheets may be produced on or attached to the surface of an electrode.

In other alternative embodiments, the graphite electrode may be surface modified, for instance, by adding graphene oxide, decorating with metallic nanoparticles (including but not limited to gold and silver nanoparticles), or depositing metal oxides or other compounds. Other types of surface modification may also be possible.

While it is preferred that the graphite electrode has no surface modification prior to the immersing, or immediately prior to the immersing, some surface modification may result when the graphite electrode is passed a current in an electrolytic cell. In other words, the is measuring process may cause surface modification of the graphite electrode. This may be considered an in situ surface modification. For instance, in one embodiment where the aqueous sample comprises $Ag^+$, silver oxide (Ago) nanoparticles may form on the surface of the graphite electrode by the oxidation of $Ag^+$. These AgO nanoparticles may have an average diameter of 5-800 nm, preferably 150-600 nm, more preferably 200-400 nm, and in some embodiments, the size and number of the nanoparticles may depend on the amount of current and voltage applied, as well as the composition of the aqueous sample. Other structures or nanostructures of silver oxide may form.

In another embodiment, where the aqueous sample comprises $Cu^{2+}$ nanoparticles of copper oxide ($Cu_2O$) may form on the surface of the graphite electrode due to, the reduction of $Cu^{2+}$ to $Cu^+$. These nanoparticles of copper oxide may have an average diameter of 50-500 nm, preferably 80-400 nm, more preferably 100-300 nm, and the size and number of the nanoparticles may also depend on the amount of current and voltage applied, and the composition of the aqueous sample. Other structures or nanostructures of copper oxide may also form. In other embodiments, molecules from the aqueous solution may adsorb to the graphite electrode, such as biomolecules, or compounds such as one or snore of the analytes listed previously. In some cases these biomolecules or compounds may be oxidized and adsorbed to the graphite electrode surface. The graphite electrode having surface modification may have affected electrical properties, for instance, an increased resistance, or an increased or decreased electroactive surface area.

In some embodiments, the non-immersed part of the graphite electrode may be attached to a potentiostat or other electrical source through a soldered connection, a clip, a conductive adhesive, or some other means. A non-immersed part of the graphite electrode may additionally be secured within a mechanical pencil.

In one embodiment, the aqueous sample further comprises at least one biomolecule selected from the group consisting of ascorbic acid, alanine, fructose, uric acid, phenylalanine, and cysteine, each independently at a concentration of 0.01-1.00 mM, preferably 0.02-0.50 mM, more preferably 0.05-0.20 mM, or preferably 0.01-0.20 mM, more preferably 0.01-0.10 mM. Preferably these biomolecules do not interfere with the detection of either methionine or glucose. In an alternative embodiment, a compound that interferes in a way to increase a current peak reading of a analyte may be added to apt aqueous sample to increase the sensitivity or measurement range of a graphite electrode.

In one embodiment of the method, glucose at a concentration of 0.01-1.00 mM, preferably 0.01-0.03 mM does not interfere with the detection of methionine. Similarly in another embodiment of the method, methionine at a concentration of 0.05-0.50 mM, preferably 0.08-0.30 mM does not interfere with the detection of glucose. However, in one embodiment, glucose and methionine, if both present, may interfere with each other, and a measurement may be adjusted to calculate a combined concentration.

In one embodiment, the molar ratio between an analyte (such as glucose or methionine) and another type of bio molecule in the aqueous sample may be 1:1-50:1, preferably 2:1-20:1, more preferably 4:1-15:1, or about 5:1 or about 10:1. Preferably, the measurement is also robust in the presence of common inorganic aqueous ions, which include, without limitation, $Na^+$, $K^+$, $Li^+$, $Ni^{2+}$, $SO_4^{2-}$, and $Cl^-$.

The aqueous sample may have a total volume of 1 mL-10 L, preferably 5 mL-1 L, more preferably 10mL-500 mL, even more preferably 15 mL-300 mL.

Because of no or low interference from other molecules, the method can be used to detect glucose or methionine in various samples such as whole blood, plasma, serum, saliva, sweat, urine, washes of tissues, extracts of tissues, amniotic fluid, and placental fluid. Preferably, the method is used to detect glucose or methionine concentrations in whole blood, plasma, or serum samples. In one embodiment, where the method is used to measure an aqueous sample comprising serum, the serum is derived or taken from a human donor.

However, where the serum is derived from a human donor, excess protein may first need to be precipitated and removed from the sample before immersing the electrodes and measuring the current response. Here, the method may further comprise removing a precipitated protein from an aqueous sample that comprises serum. The protein may first be precipitated from a serum sample by chemical denaturation (for instance, mixing the serum with a base, detergent, and/or an organic solvent) or heating. In an alternative embodiment, the protein may be removed by chromatography, and without denaturation.

In one embodiment, the serum sample from a patient is mixed with an alcohol, including, but not limited to, methanol, ethanol, n-propanol, isopropanol, and n-butanol. Preferably the sample is mixed with methanol. The serum sample may be mixed with the alcohol at a volume ratio of 1:4-4:1, preferably 1:4-1:1, more preferably 1:3-1:2, or about 1:2. The serum sample and alcohol may be mixed for 5 min-3 hours, preferably 10 min-1 hour, or as long as overnight. This mixing may produce a precipitated protein.

The precipitated protein may then be removed by centrifugation and/or filtration. This may be performed by standard laboratory techniques. In one embodiment, the serum sample comprising precipitated protein may be centrifuged at 1,000-10,000 rpm, preferably 1,500-3,000 rpm, or about 2,000 rpm for 5-30 minutes, preferably 15-25 minutes, or about 20 minutes, to produce a clear supernatant. The clear supernatant may be filtered, for instance, with a 0.2-0.45 μm pore size filter.

The clear supernatant, or some other sample containing the analyte, may also be diluted before measurement. The clear supernatant or sample may be diluted 20-10,000 times, preferably 40-500 times, more preferably 50-300 times. It is preferred that a dilution factor is chosen so that an analyte concentration falls within or close to the linear response of the electrode measurement.

In one embodiment, some amount of analyte from a sample may be lost, especially if a sample is processed or filtered to remove protein or other compounds. However, the methods described herein may show a high amount of analyte recovery, preferably at least 96%, more preferably at least 97%, even more preferably at least 98%. Here, the analyte recovery is the percentage of the measured analyte concentration of the analyte with respect to the actual analyte concentration.

The reference electrode may be a standard hydrogen electrode, a normal hydrogen electrode, a reversible hydrogen electrode, a saturated calomel electrode, a silver chloride (Ag/AgCl) electrode, or a dynamic hydrogen electrode. Preferably, the reference electrode is a silver chloride (Ag/AgCl) electrode. In one embodiment, the reference electrode is an Ag/AgCl electrode, and the counter electrode comprises platinum, gold, or some other metal. Preferably the counter electrode is a platinum wire. The counter electrode may also be called an auxiliary electrode.

The graphite electrode is in electrical communication with the reference electrode. After the immersing, a potential is applied between the reference electrode and the modified graphite electrode to produce a current within the aqueous sample. The biasing potential may have the waveform of a linear scan voltammetry, a square wave voltammetry, or a cyclic voltammetry. In one embodiment, cyclic voltammetry may be applied, using a linear scan of voltage in both directions (low to high potential and high to low potential). In another embodiment, linear scan voltammetry may be used with a scan in only one direction. For instance, linear scan voltammetry may be used to scan from a high potential to a low potential, which is also called cathodic sweep linear scan voltammetry (CSLSV) is used. The potential applied in this region may cause surface oxidation reactions on the surface of the graphite electrode, which may be noticeable as current peaks. CSLSV may be used to scan from 1.5 V to −0.5 V, preferably 1.0 to −0.2 V. A voltage scan rate may be 10-400 mV/s, preferably 50-200 mV/s, more preferably 80-120 mV/s, or about 100 mV/s. However, in some embodiments, the voltage scan rate may be slower than 10 mV/s or faster than 400 mV/s. In an alternative embodiment, voltammetry may be used that does not scan linearly through a range of potentials, for instance, different potentials may be applied at discrete steps.

Changes in the current as a result of reduction or oxidation of analytes may be compared to a correlation chart or a calibration curve to determine the concentration of analyte. Here, the correlation chart or calibration curve relates an analyte concentration for a particular value of current measured. The correlation chart or calibration curve may be further influenced by other parameters such as voltage, temperature, pH, electrolyte concentration, and other solution conditions. Because of the influence of several solution conditions on the measurement of the analyte, the method may comprise a step of measuring standard solutions to construct a correlation chart or calibration curve. This provides a way to better ensure that certain solution conditions do not differ significantly between samples and standard solutions.

In one embodiment, cyclic voltammetry may be used with an aqueous sample to first identify the location of current peaks as a result of redox reactions. One or more current peaks may be observed in the cathodic sweep (high to low potential) and/or the anodic sweep (low to high potential). The value of the current peaks may be used from those cyclic voltammograms, or a linear scan voltammetry may next be applied using only a cathodic sweep or only an anodic sweep.

By changing the applied potential in any form of voltammetry, the current may vary based on electrochemical reaction of analyte. As mentioned previously, the current may peak during the voltage scan. For a particular analyte, this peak may occur at a particular voltage or within a smaller range of voltages, and the value of the current at the peak may be linearly dependent on the concentration of analyte. In one embodiment, the analyte is glucose, and the voltage of its current peak is 0.60-0.65 V. preferably 0.61-0.64 V, or about 0.63 V. In one embodiment, the analyte is methionine, and the voltage of its current peak is 0.63-0.67 V, preferably 0.64-0.66 V, or about 0.65 V. Preferably, these current peaks of glucose and methionine are observed in the cathodic region of the voltammogram (high potential to low potential), and these current peaks may be considered secondary oxidation peaks.

Alternatively, a linear response in current may be obtained by applying a potential at or near the voltage relating to the current peak of the particular analyte. In this sense, the measurement technique may be more similar to amperometry. The voltage may be constant or relatively stable, and the current or an average value of current is measured.

In one embodiment, the measuring further involves constructing a calibration curve from a current response of two or more standard solutions. This may be considered equivalent to constructing a calibration curve from a correlation chart. Preferably, the standard solutions comprise an identical analyte to the one being measured, though in other embodiments, the standard solutions may comprise a different species that has a similar electrochemical response. Preferably the standard solutions produce currents within the linear response range of the graphite electrode, so that a linear calibration curve may be determined to relate current to analyte concentration. Preferably, more than two standard solutions of different concentrations are used, for instance, 3-10 standard solutions, or 4-6 standard solutions. In one embodiment, separate standard solutions may each be prepared and measured one at a time. However, in another embodiment, standard solutions may be measured by a standard addition method, where one volume is measured, and then, is mixed with standard solution (usually of a volume 10-1,000 times smaller), while the electrodes are kept in place.

Preferably, where standard solutions are used to construct a linear calibration curve, preferably the standard solutions are within a linear response range of the graphite electrode, so that the linear calibration curve has a correlation coefficient, $R^2$, of at least 0.90, preferably at least 0.95, more preferably at least 0.97, even more preferably at least 0.99.

In one embodiment, where the analyte is glucose, the measurement method may have a limit of detection (LOD) of 0.03-5.0 μM, preferably 0.1-4.0 μM, more preferably 1.0-1.4 μM, or about 1.36 μM. The sensitivity of the electrode in this embodiment may be 20-1000 $\mu A \cdot mM^{-1} \cdot cm^{-2}$, preferably 100-800 $\mu A \cdot mM^{-1} \cdot cm^{-2}$, or about 315 $\mu A \cdot mM^{-1} \cdot cm^{-2}$.

In the embodiment where the analyte is methionine, the measurement method may have a limit of detection (LOD) of 0.01-5.0 μM, preferably 0.05-1.0 μM, more preferably 0.20-0.8 μM, or about 0.42 μM. The sensitivity of the electrode in this embodiment may be 100-10,000 $\mu A \cdot mM^{-1} \cdot cm^{-2}$, preferably 800-8,000 $\mu A \cdot mM^{-1} \cdot cm^{-2}$, or about 4,500 µA·mM$^{-1}$·cm$^{-2}$. The limit of quantification (LOQ) may be 0.5-70 µM, preferably 5-20 µM, or about 10 µM.

In one embodiment, rather than measuring a concentration of an analyte, linear scan voltammetry or cyclic voltammetry of the aqueous sample may be used to detect whether or not a sample is present. In this embodiment, the analyte concentration may be lower than, within, or greater than the linear response range of the graphite electrode. Additionally, this method of detection may rely on reporting the presence or absence of a peak in a voltammogram, rather than a particular value of current.

In one embodiment, the analyte concentration may be determined using amperometry and standard additions. Here, the potential may be held constant, and the level of current may be measured by sequentially adding and mixing standard additions. In order to increase the concentration by approximately the same amount each time. Each addition may be spaced by a time interval such as 20-100 s, or 30-60 s. A linear calibration curve may be similarly constructed as mentioned previously.

Following the measuring, the graphite electrode may be reusable and may be capable of repeated detection without calibration or replacement.

In one embodiment, the graphite electrode may be part of, or integrated in, a sensing device which comprises the aforementioned reference electrode and counter electrode. The sensing device may include a housing that comprises at least one graphite electrode, and a fluid distribution manifold that comprises a fluid flow path that is in fluid communication with the graphite electrode, the counter electrode, and the reference electrode. The fluid flow path may bring a fluid comprising at least one analyte in contact with the graphite electrode for sensing.

The sensing device may be in communication with at least one readout device that may generally be capable of measuring the current and/or potential at the graphite electrode.

In most embodiments, the readout device may be a set of electronics. An electronic readout device, for example, may be capable of detecting current changes. Moreover, the readout device may be a component of the sensing device or may be separated from the sensing device. Furthermore, the readout device may also be linked to an adapter that may interface with a controller device. Preferably, a readout circuit used to enable determination of the presence and/or amount of analyte may form part of the readout device. In some embodiments, the readout circuit may be configured to measure the current and/or the potential at the graphite electrode. The readout circuit may also be configured to indicate the current and/or potential value(s) to a user of the sensing device such that he/she may detect the presence of the analyte and quantify it based on this measurement. To achieve this, the readout circuit may comprise an electronic display and/or a loudspeaker for presenting the current and/or potential value(s) to the user, and may further comprise a transmitter (or transceiver) for transmitting the data to another device. The latter feature enables the user to monitor the environment from a remote location. In another embodiment, the readout circuit may be configured to determine the presence and/or amount of analyte using the current and/or potential value(s) and indicate the result to the user (with or without the current and/or potential value(s)). This embodiment therefore provides the user with the end result without requiring him/her to derive it from the raw data.

In practice, this analysis would be performed by the processor in combination with a storage medium. For example, a processor may be configured to receive the current and/or potential value(s) from the readout circuit and compare this with predetermined calibration data (e.g. predetermined measurements of current and/or potential difference versus analyte concentration) from the storage medium to determine the presence and/or amount of analyte.

The examples below are intended to further illustrate protocols for preparing, and using graphite pencil electrodes for measurement and detection of glucose and methionine, and are not intended to limit the scope of the claims.

EXAMPLE 1

Materials and Methods for Glucose Detection
Chemicals

A Cu AAS specification standard solution (1000ppm±4.0) was prepared with nitric acid (HNO$_3$) and sodium phosphate mono-basic anhydrous (NaH$_2$PO$_4$) obtained from Fluka. Sodium phosphate di-basic anhydrous (Na$_2$HPO$_4$), sodium hydroxide pellets, D-glucose, uric acid (UA), D-fructose, L-ascorbic acid (AA), and L-alanine were all used as purchased from Sigma-Aldrich. All solutions were prepared with double distilled water obtained from an AQUATRON water still A4000D water purification system.

Electroanalytical Apparatus and Procedures

The three electrode system comprises a pencil, made in Korea, which has a graphite lead that can be propelled or extruded mechanically as a working electrode, an Ag/AgCl saturated KCl electrode as a reference electrode, and platinum wire as a counter electrode. These three electrodes were connected with a CHI potentiostat workstation (CH11140A, CH Instruments Inc, Austin, Tex., USA) for all electrochemical experiments and measurements, which additionally used a 0.10 M NaOH solution as supporting electrolyte. Descriptions, fabrication and working principle of the mechanical pencil have been reported in the literature. See J. Wang, A. -N. Kawcle, Pencil-based renewable biosensor for label-free electrochemical detection of DNA hybridization, Analytica Chimica Acta, 431 (2001) 219-224, incorporated herein by reference in its entirety. About 7.00 mm length of graphite lead of 0.50 mm diameter propelled out of the vertically fixed pencil with an electrical contact achieved by soldering of copper on its metallic part were made to be in contact with the electrolyte solution corresponding to surface area of about 11.39 mm$^2$.

Cyclic voltammetry (CV) measurements were done in the potential window of −0.20 V to 0.80 V with scan rate of 100 mV/s. Cathodic sweep linear scan voltammetry (CSLS V) techniques were employed as the electrochemical technique for glucose determination between 1.00 V and −0.20 V potential. Measurements were taken at room temperature, and the accumulations step was done under stilling before cathodic sweeping at quiescent condition after 5 s of quiet time.

GPE Surface Characterization

Images of GPE were recorded with FE-SEM and EDX instruments by TESCAN LYRA 3 at the the Center of Research Excellence in Nanotechnology, King Fahd University of Petroleum and Minerals (KFUPM), Kingdom of Saudi Arabia (KSA). X-ray photon Spectroscopy (XPS) investigation was performed with Thermo-Scientific ESCALAB-250Xi instrument with monochromatic Al Kα radiation, hv=1486.6 eV, installed in the Physics Department of KFUPM, KSA. Data obtained from XPS was processed with THERMO AVANTAGE, version 5.51, Surface Chemical Analysis software.

Scrum Sample Collection and Preparation

A serum sample was collected from a healthy patient with the assistance of the Imam Abdulrahman Teaching Hospital blood bank section (King Fand Teaching Hospital). The serum sample was stored in the refrigerator to defrost, and a 450 µL aliquot was taken and treated with methanol (900 µL) in a 1:2 volume ratio to precipitate protein from the serum sample. The precipitated protein was from the sample with 20 minutes of centrifugation at 2000 rpm and filtering the clear supernatant with a of 0.45 µm pore size MIL-LIPORE filter.

EXAMPLE 2

Figure 2A:
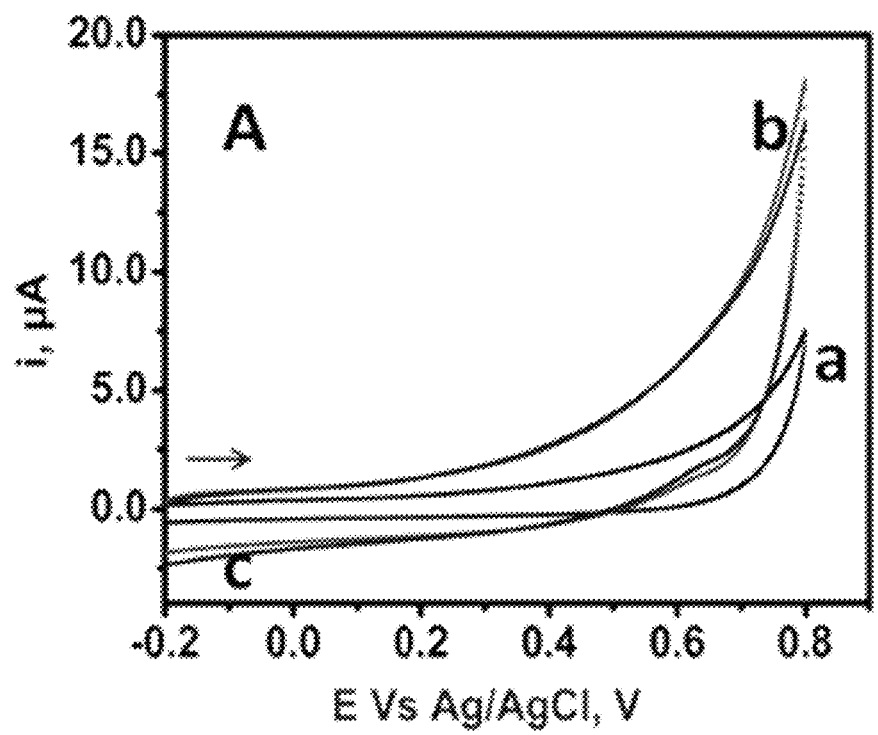
FIG. 2A is a cyclic voltammogram by a GPE in 0.10 NaOH in the absence of Cu and with (a) 0, (b) 2 mM, or (c) 4 mM glucose.

Results and Discussion for Glucose Detection
Redox Reactions of Glucose in the Presence of Copper on GPE In the absence of Cu, as shown in curves "b" and "c" of FIG. 2A, a secondary oxidation peak of 2 mM and 4 mM glucose respectively can be observed at about 0.63 V on a bare GPE in 0.10 M NaOH. This is due to the graphitic nature of GPE as compared to other solid electrodes that could not show similar response without any surface modifications. However, enhanced peaks of glucose were observed in in curves and "c" of FIG. 2B for the same glucose concentrations as in FIG. 2A due to the presence of 5.00 ppm $Cu(NO_3)_2$ solution. However, no redox peaks of Cu could be noticed in curve "a" of FIG. 2B despite the presence of the 5.00 ppm $Cu(NO_3)_2$ solution. Oxidation peaks could not be observed either is due to the presence of Cu in form of $Cu^{2+}$ in the medium which could no longer be oxidized, or because of the lower concentration of Cu accumulated on GPE which might be below the detection limit. Besides, there is a possibility of reduction of $Cu^{2+}$ to $Cu^+$ which is also not noticed in the cathodic region of the cyclic voltammogram in "a" of FIG. 2B. This can be attributed to the instability of the $Cu^+$ species in aqueous solution. Besides, a peak resulting from the reduction of $Cu^{2+}$ to $Cu^+$ has been successfully reported with the aid of selected ligand as a chelating agent in the electrochemical investigations of Cu on Cu electrodes. See C. Giacomelli, F. C. Giact A. L. Santana, V. Schmidt, A. T. N. Pires, J. R. Bertolino, A. Spinelli, Interaction of poly(4-vinylpyridine) with copper surfaces: electrochemical, thermal and spectroscopic studies, Journal of the Brazilian Chemical Society, 15 (2004) 818-824; and R. S. Gonsalves, A. M. S. Lucho, Electrochemical studies of copper in N—N, dimethylformamide in the presence of water, ethanol and acetic acid as additives, Journal of the Brazilian Chemical Society, 11 (2000) 486-490, each incorporated herein by reference in their entirety. Surprisingly, the secondary oxidation peak of glucose observed in "b" and "c" of FIG. 2A was enhanced by the presence of Cu in the medium. The reduction peak resulting from the reduction of $Cu^{2+}$ to $Cu^+$ on the surface of the GPE is likely to be responsible for the enhancement of glucose peaks observed in "b" and "c" of FIG. 2B.

Figure 3A:
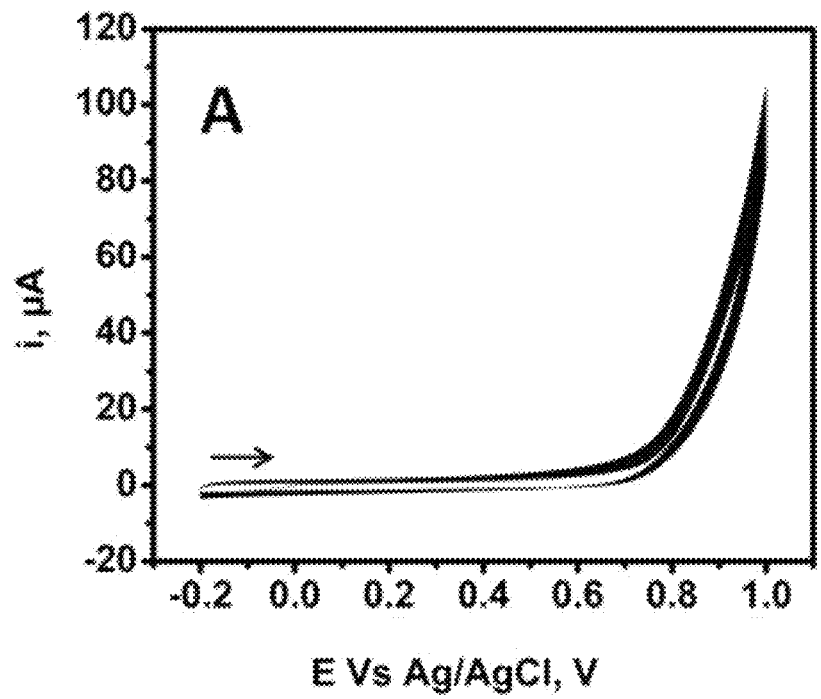
FIG. 3A shows a cyclic voltammogram with 25 voltage sweeps with a GPE in 0.10 M NaOH in the absence of $Cu(NO_3)_2$.
Figure 3B:
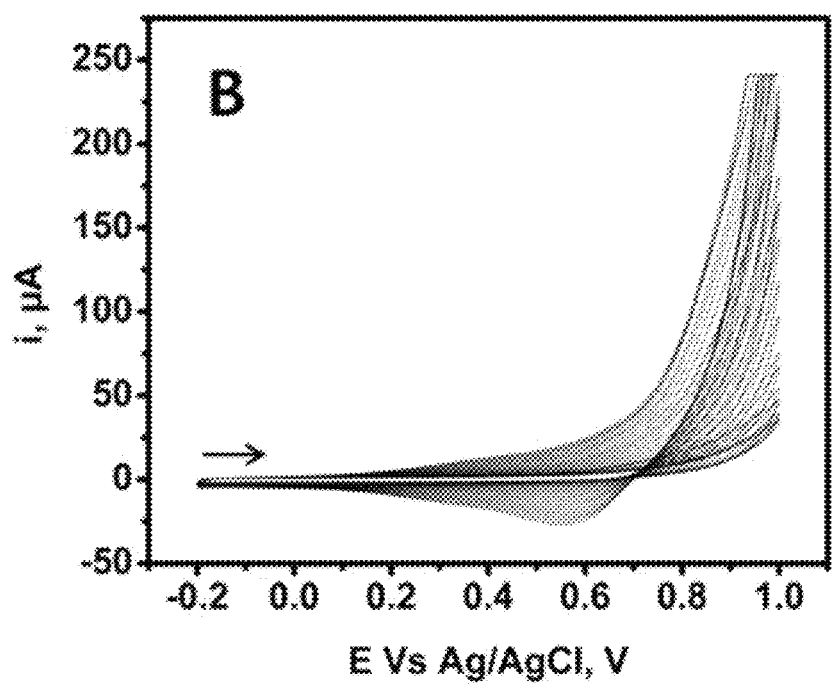
FIG. 3B shows a cyclic voltammogram with 25 voltage sweeps with a GPE in 0.10 M NaOH in the presence of 10.00 ppm $Cu(NO_3)_2$.

The electrochemical redox reaction of $Cu(NO_3)_2$ on the surface of GPE was studied by multiple cycles of CV to probe the reduction peak of $Cu^{2+}$ to $Cu^+$ in 0.1 M NaOH solution. FIG. 3A and 3B represent 25 cycles with GPE in NaOH in the absence and presence of 10.00 ppm $Cu(NO_3)_2$ solution, respectively. A broad accumulation reduction peak of $Cu^{2+}$ to $Cu^+$ can be observed in FIG. 3B in the cathodic region of the multiple CV sweep.

FE-SEM and LDX Analysis

Figure 4A:
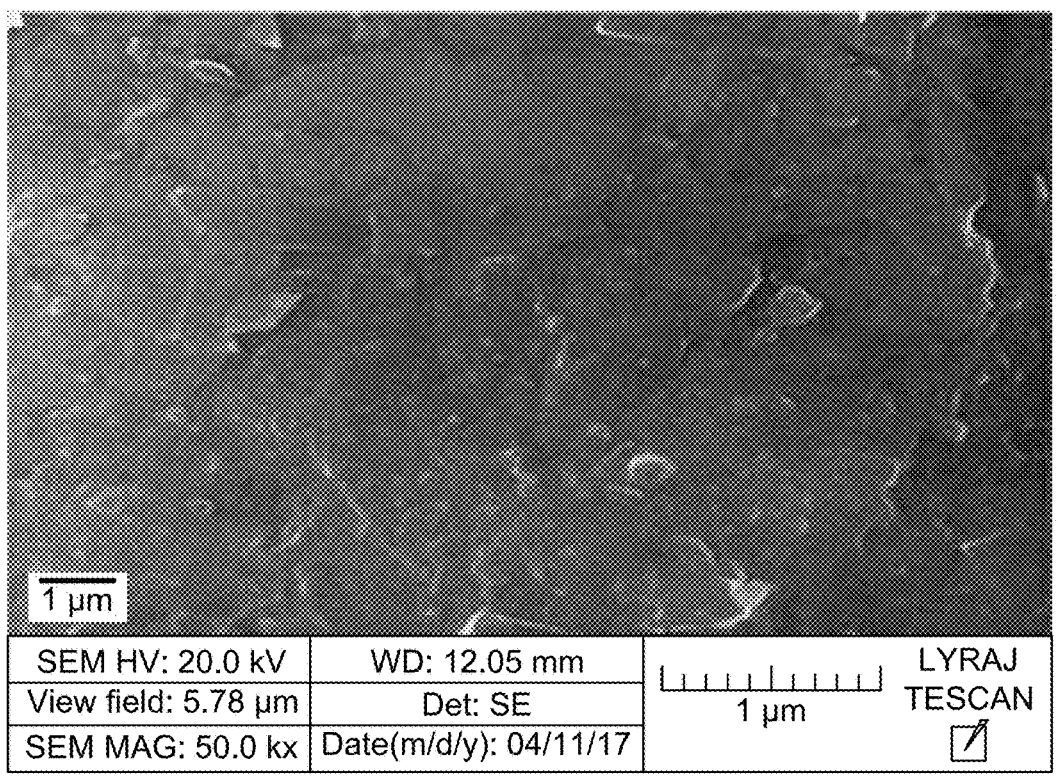
FIG. 4A is a FE-SEM image of a bare GPE.
Figure 4B:
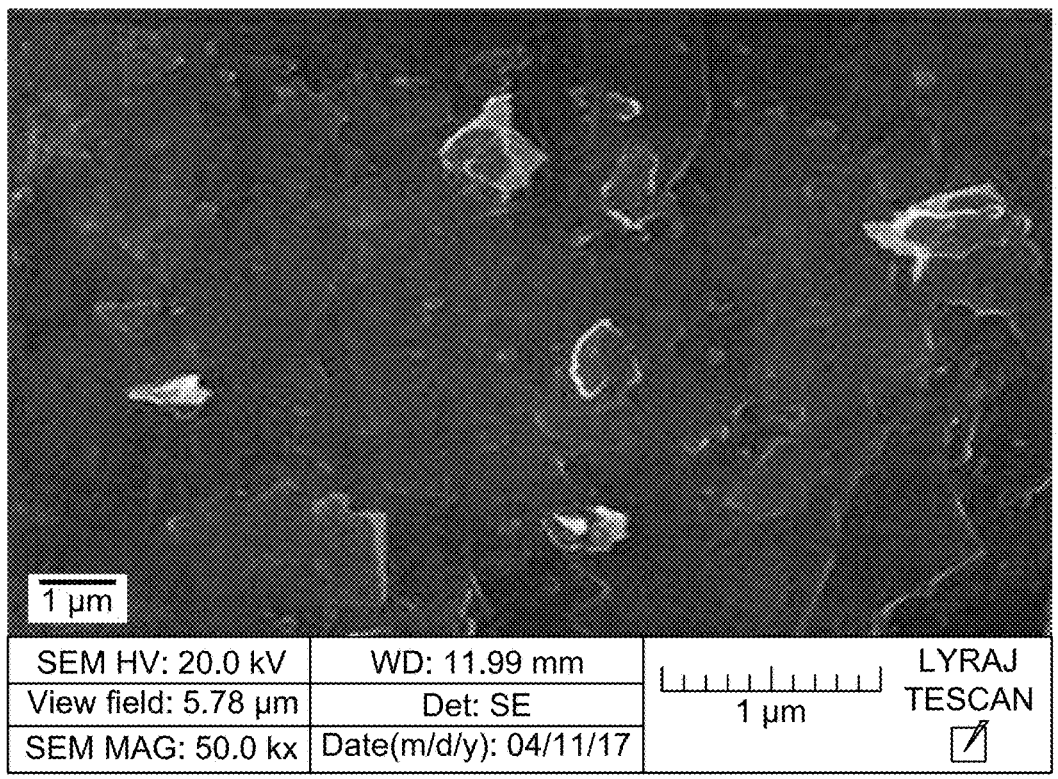
FIG. 4B is a FE-SEM image of a GPE after 25 voltammetry cycles in 0.10 M NaOH.
Figure 4C:
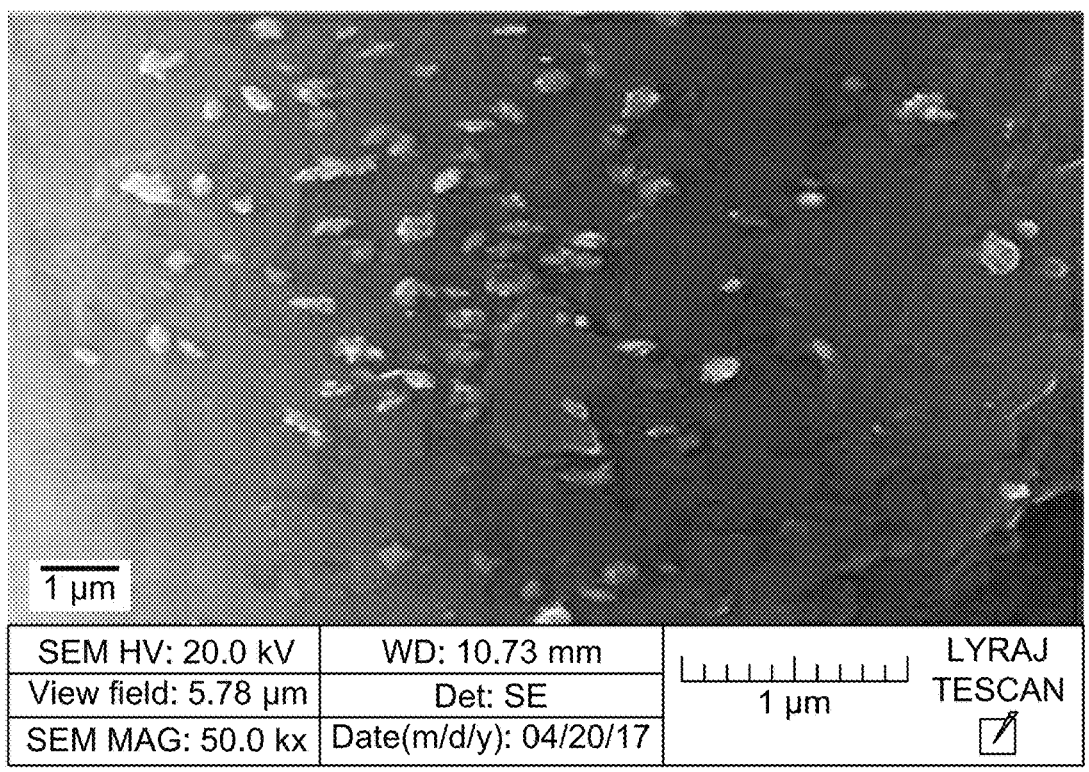
FIG. 4C is a FE-SEM image of a GPE after 25 voltammetry cycles in 0.10 M NaOH and 10.00 ppm $Cu(NO_3)_2$.
Figure 4D:
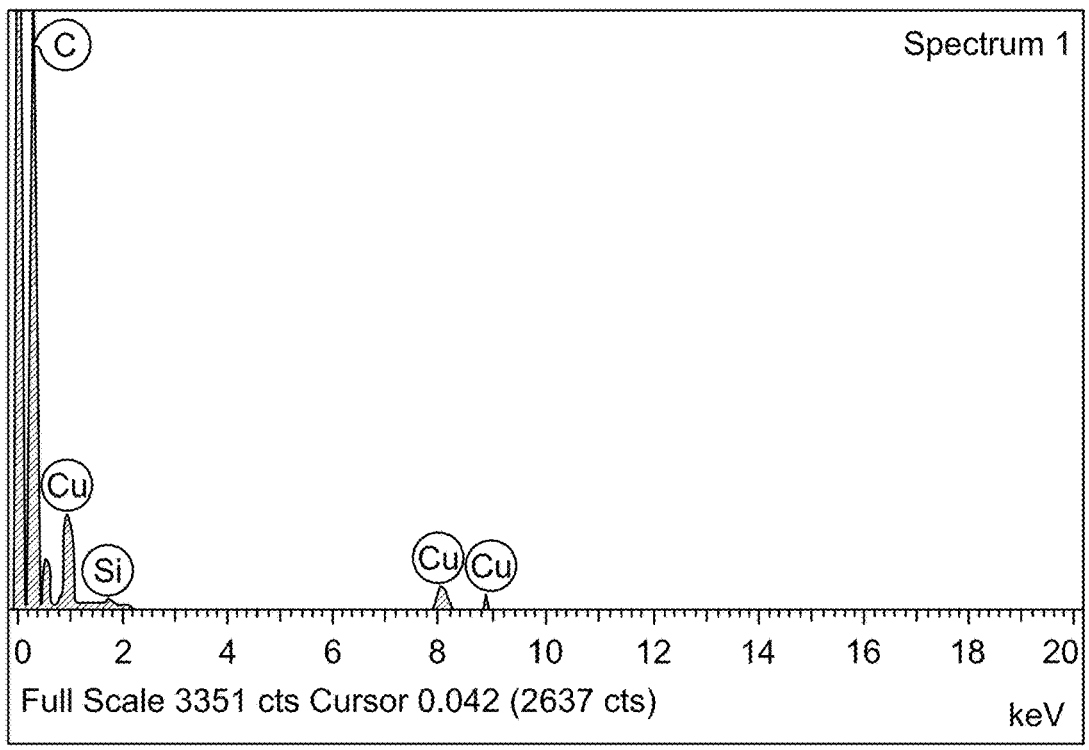
FIG. 4D is an EDX elemental composition analysis of the GPE from FIG. 4C.

The effects of the $Cu^{2+}$ to $Cu^+$ reduction peak on the surface of GPE were investigated by FE-SEM EDX analysis after 25 cycles CV as measured previously in FIGS. 3A and 3B. FIG. 4A and 4B show the image of bare GPE, and GPE in 0.10 M NaOH without $Cu(NO_3)_2$ solution, respectively. The formation of irregularly shaped Cu oxides can be observed on the GPE surface from the solution containing 10.00 ppm $Cu(NO_3)_2$ in 0.1 M NaOH (FIG. 4C). Elemental composition of the surface of GPE by EDX spectra (FIG. 4D) reveal an average weight percent of 5 spot analyses of 96.02, 0.42, and 3.56 for C, Si, and Cu, respectively, confirming the presence of Cu on the GPE surface.

Figure 5A:
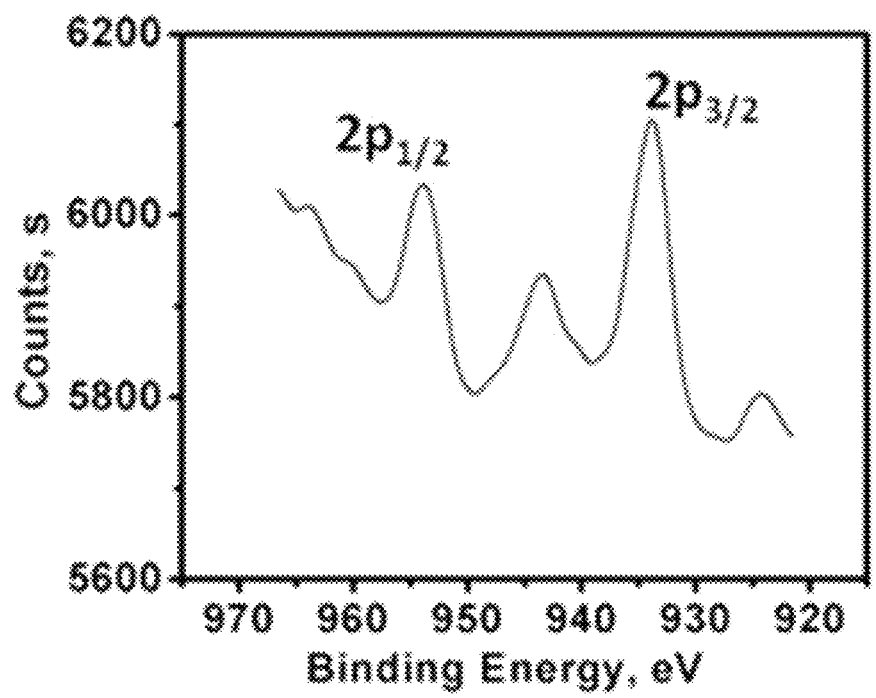
FIG. 5A is an XPS analysis of Cu 2p on a GPE surface after 25 voltammogram cycles in 10.00 ppm $Cu(NO_3)_2$ and 0.1 M NaOH.
Figure 5B:
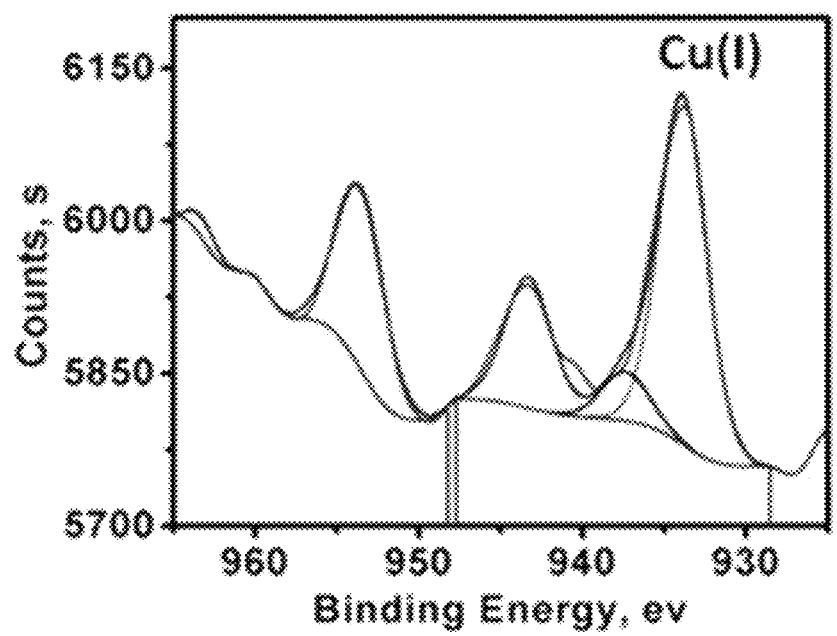
FIG. 5B is a deconvolution of the peaks in FIG. 5A
Figure 5C:
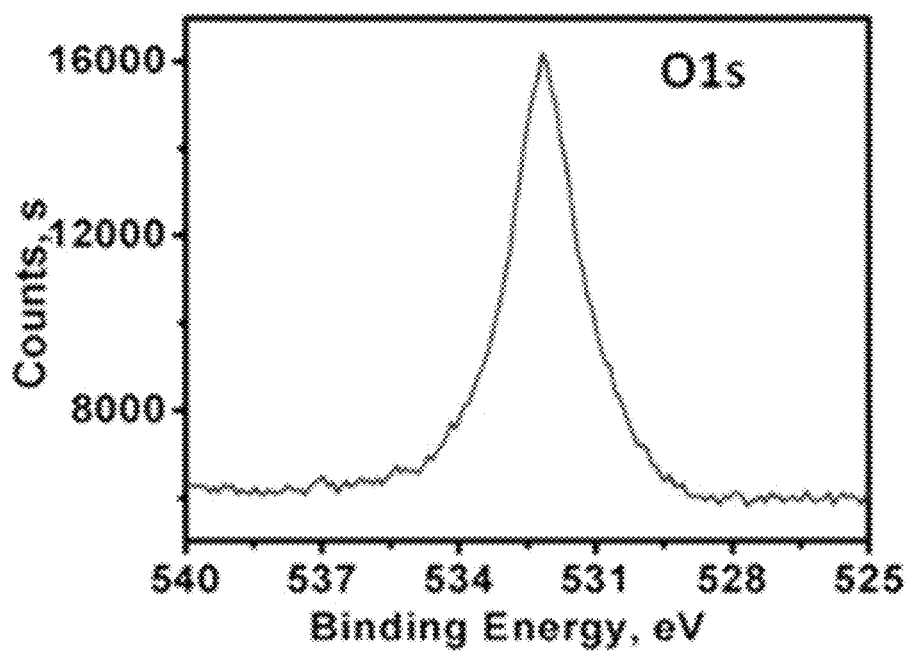
FIG. 5C is an XPS analysis of O 1 s on a GPE surface after 25 voltammogram cycles in 10.00 ppm $Cu(NO_3)_2$ and 0.1 M NaOH.
Figure 5D:
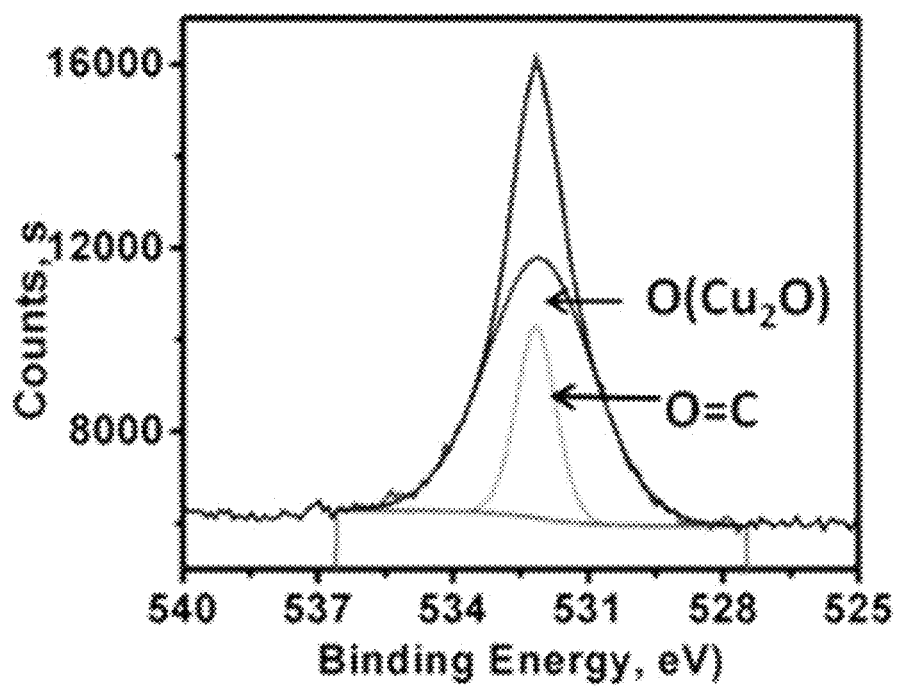
FIG. 5D is a deconvolution of the peaks in FIG. 5C.

The chemical state of the Cu revealed by the EDX elemental analysis (FIG. 4D) was investigated with XPS Cu 2p and O 1 s spectra (FIGS. 5A-5D). Characteristic peaks of Cu $2p_{1/2}$ and Cu $2p_{3/2}$ at about 953 eV and 933 eV, respectively, attributed to $Cu_2O/CuO$ can be observed in FIG. 5A. See Y.-Y. Liu, Z.-X. Wang, X. He, M. Shao, M.-X. Li, One unexpected mixed-valence Cu(I,II)-cyanide coordination polymer in situ originating from the cleavage of acetonitrile, Inorganic Chemistry Communications, 80 (2017) 46-48; and K. Tang, X. Wang, W. Yan, J. Yu, R. Xu, Fabrication of superhydrophilic $Cu_2O$ and CuO membranes, Journal of Membrane Science, 286 (2006) 279-284, each incorporated herein by reference in their entirety. Analysis of FIG. 5A revealed the presence of CuO on the GPE by a strong $Cu^{2+}$ satellite peak with a binding energy (BE) of 943.31 eV as shown in FIG. 5B. This peak is expected to be weak if it is pure $Cu_2O$, but the weak intensity of the second satellite peak of $Cu^{2+}$ at 960.06 eV leverages the influence of CuO. The dominance of $Cu_2O$ on GPE surface was further confirmed by an obvious higher ratio peak with BE of 933.36 eV (10:1) compared with its counterpart with BE of 937.36 eV, which is regarded as a footprint of $Cu_2O$, and confirmation of $Cu_2O$ as the significant species of Cu on the GPE-surface. See B. V. Crist, Handbooks of monochromatic XPS spectra, XPS International, 1999, incorporated herein by reference in its entirety. Similar observation of the presence of $Cu_2O$ was reveal in the O 1 s spectra at about 532 eV (FIG. 5C). Presence of $Cu_2O$ (532.08 eV) along with O═C (532.16 eV) that can be attributed to the adsorption of $Cu_2O$ to GPE can be observed in FIG. 5D.

Proposed Glucose Redox Reactions Mechanism on GPE

Oxidations of different forms of copper immobilized on solid electrodes to +1, +2 and +3 oxidation states for glucose detection have been reported with mechanisms supporting copper peroxide (CuOOH) which have often referred to as $Cu^+$ as the species responsible for electrocatalysis of glucose in basic medium. These mechanisms are shown in eqn. (1-3). See A. A. Ensafi et al.; C. Kong et al.; S. Pourbeyram et al.; J. Xu et al.; and B. Wang et al., each incorporated herein by reference in their entirety. This mechanism is valid for oxidation of glucose based on the abstraction of hydrogen from the β-OH group of the hemiacetal carbon center (carbon with ether and alcohol groups) by $Cu^{3+}$ species and can be supported by a comprehensive study of $Cu^{3+}$ complex for hydrogen atom abstraction from hydrocarbon. See D. Dhar, W. B. Tolman, Hydrogen Atom Abstraction from Hydrocarbons by a Copper(III)-Hydroxide Complex, Journal of the American Chemical Society. 137 (2015) 1322-

1329, incorporated herein by reference in its entirety. However, $Cu^{2+}$ species complex have also been reported to be an active hydrogen atom abstraction from organic molecules. See M. Taki, H. Kumei, S. Itoh, S. Fukuzumi, Hydrogen atom abstraction by Cu(II)- and Zn(II)-phenoxyl radical complexes, models for the active form of galactose oxidase, Journal of Inorganic Biochemistry, 78 (2000) 1-5, incorporated herein by reference in its entirety.

$$Cu^0+2OH^-\rightarrow CuO+H_2O+2e^- \text{ or } Cu^0+2OH^-\rightarrow Cu(OH)_2+H_2O+2e^- \quad (1)$$

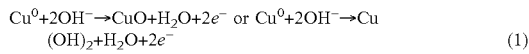

$$CuO+OH^-\rightarrow CuOOH+e^- \text{ or } CuO+H_2O+2OH^-\rightarrow Cu(OH)_4^-+e \quad (2)$$

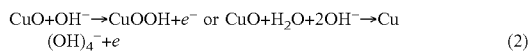

$$Cu^{3+}+glucose+e^-\rightarrow gluconolantone+Cu^{2+} \quad (3)$$

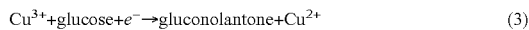

It is worth mentioning that none of the equations (1-3) represents a redox reaction of Cu (either metallic or $Cu^{2+}$) to +1 oxidation state. Besides, a misrepresentation of oxidation state of Cu in CuOOH as shown in equation (2) needs special consideration. The oxidation state of Cu in CuOOH is +1, in contrast to +3, because oxygen always has an oxidation number of −1 in peroxides. So, equation (2) can also be possible electrochemically by reduction reaction of $Cu^{2+}$ to $Cu^+$ by gaining of an electron as shown in FIG. 1.

The scheme in FIG. 1 is a proposed mechanism of the glucose secondary oxidation peak on GPE as represented by equations (4-6). This mechanism is possible based on the coincidental reduction peaks of $Cu^{2+}$ $Cu^+$ between 0.50 and 0.60 V (FIG. 2B) and secondary oxidation peak of glucose on GPE (FIG. 2A). This is in agreement with the model predicted by Pletcher, 1984. See D. Pletcher, Electrocatalysis: present and future, Journal of Applied Electrochemistry, 14 (1984) 403-415, incorporated herein by reference in its entirety. It involves simultaneous adsorption of glucose on the surface containing metal electro-catalyst ($Cu^+$) and removal of hemiacetal hydrogen atom which is the rate determining step for electro-oxidation of glucose.

$$Cu(OH)_2+OH^-+e^-\rightarrow CuOOH+H_2O \text{ (Reduction)} \quad (4)$$

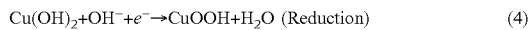

$$CuOOH \text{ }(Cu^+)+glucose\rightarrow gluconolactone+Cu(OH)_2+e^- \text{ (Oxidation)} \quad (5)$$

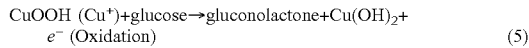

$$Gluconolactone+H_2O\rightarrow Gluconic \text{ } acid \text{ (Hydrolysis)} \quad (6)$$

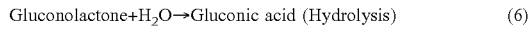

Effect of Cu Concentration on Glucose Oxidation

Figure 2B:
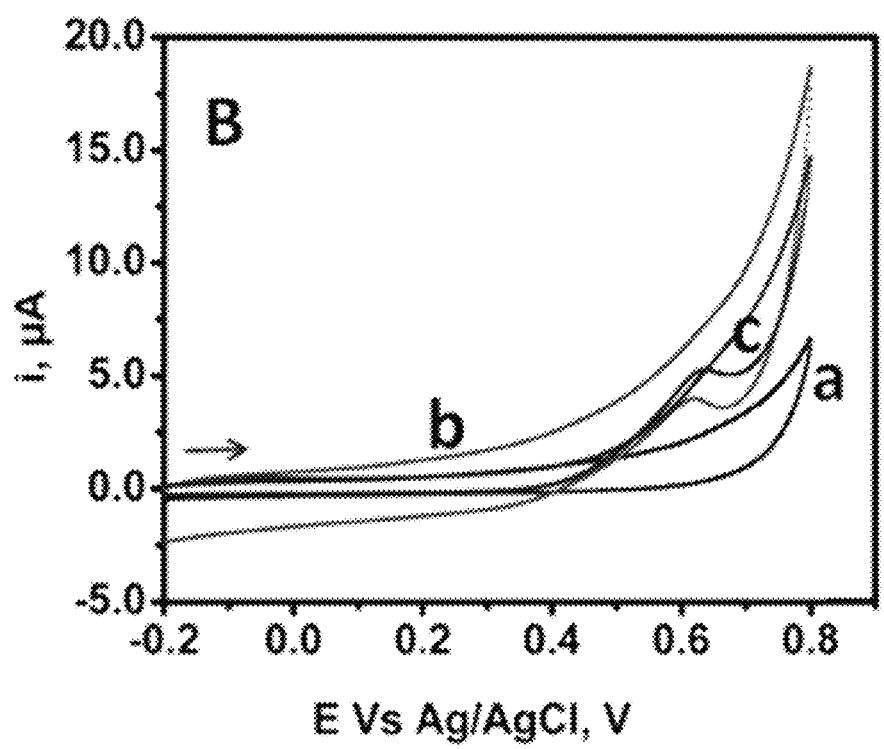
FIG. 2B is a cyclic voltammogram by a GPE in 0.10 NaOH in the presence of 5.00 ppm $Cu(NO_3)_2$ and with (a) 0, (b) 2 mM, or (c) 4 mM glucose.
Figure 6A:
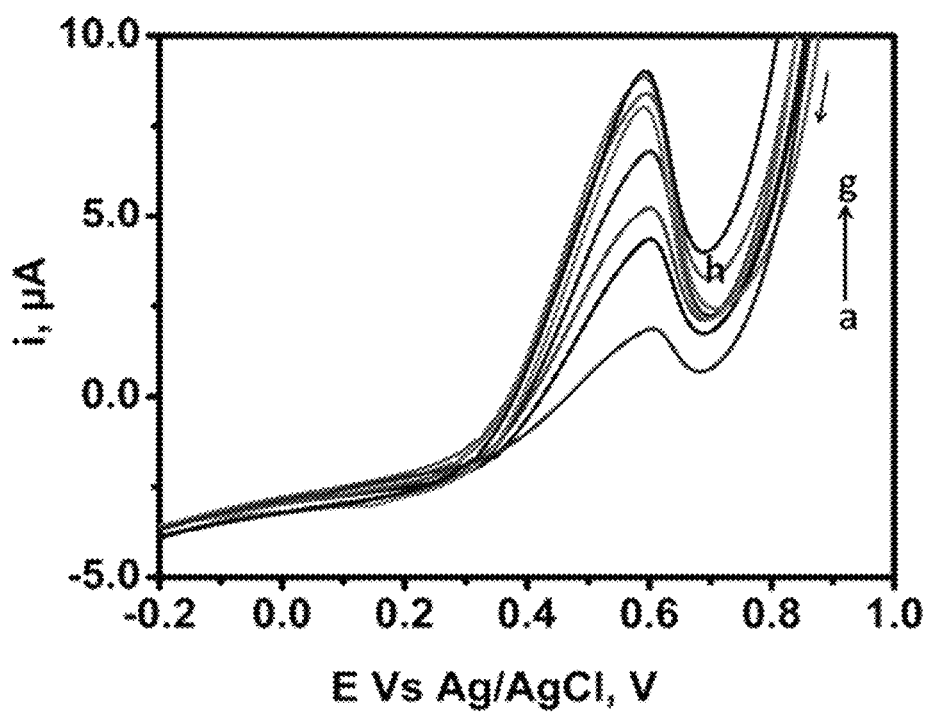
FIG. 6A shows CSLSVs of 2 mM glucose in 0.10 M NaOH at different concentrations of Cu (ppm): (a) 0.0 (b) 0.20 (c) 0.40, (d) 0.50, (e) 1.00, (0 2.00, (g) 4.00, and (h) 5.00.
Figure 6B:
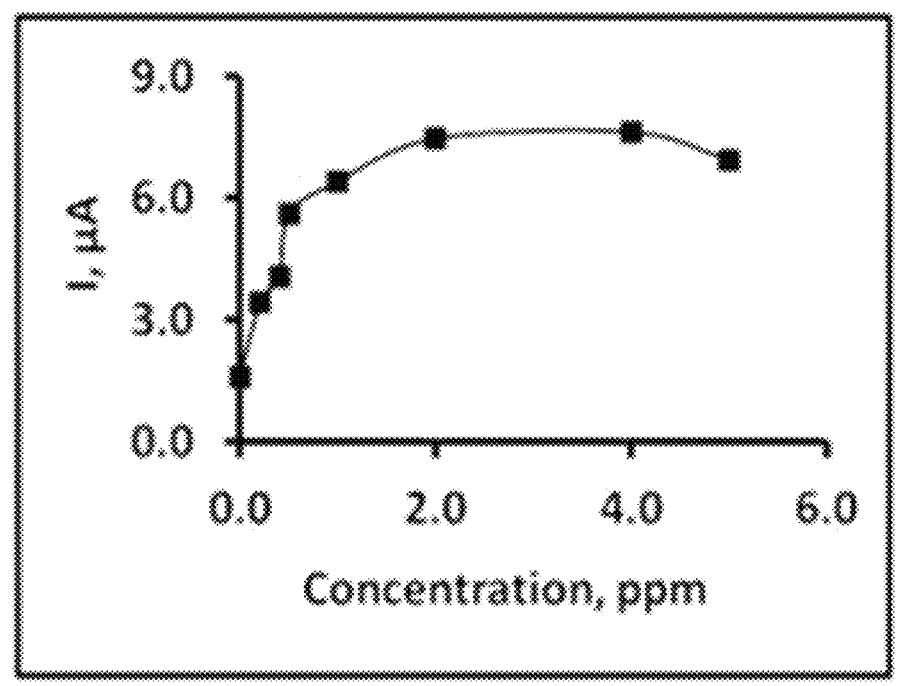
FIG. 6B shows the current peaks obtained for each sample of FIG. 6A.

CSLSV was used for subsequent electrochemical investigations since all the a lions involving glucose detection occur on the cathodic segment of the CVs as presented in FIGS. 2A and 2B. In order to obtain the optimal concentration of Cu required for glucose enhancement, a series of concentrations of Cu were tested by measuring the current-peak of 2 mM glucose in 0.10 M NaOH solution by CSLSV as represented in FIGS. 6A and 6B. Measurement began with zero (0 ppm) concentration of Cu (curse (a) in FIG. 6A), and proceeded with addition of 0.20 ppm 5.00 ppm Cu to the 2 mM glucose solution as presented in curves (b) to (h) of FIG. 6A. The corresponding current-peaks are represented with a bar chart in FIG. 6B. The electro-catalytic effect of Cu can be observed by the increase of the current-peak of 2 mM glucose when comparing with and without Cu. Current-peaks of glucose were found to be increasing with continuous addition of Cu from 0.20 to 2.00 ppm (FIG. 6A, curves (b) to (f)). However, no significant difference was observed between the current-peak for 2 mM glucose with 2.00 ppm Cu vs. 4.00 ppm Cu (curves (1) and (g), FIG. 6A). Additional concentration of Cu beyond 4.00 ppm leads to a reduction in current-peak of glucose as shown for the 5.00 ppm Cu concentration (curve (h)). The trend of this electro-catalytic behavior of Cu for the enhancement of glucose current-peak suggests 2.00 ppm Cu as the optimal value for glucose detection.

Electro-Catalytic Activity of Cu in Glucose Oxidation

Figure 7A:
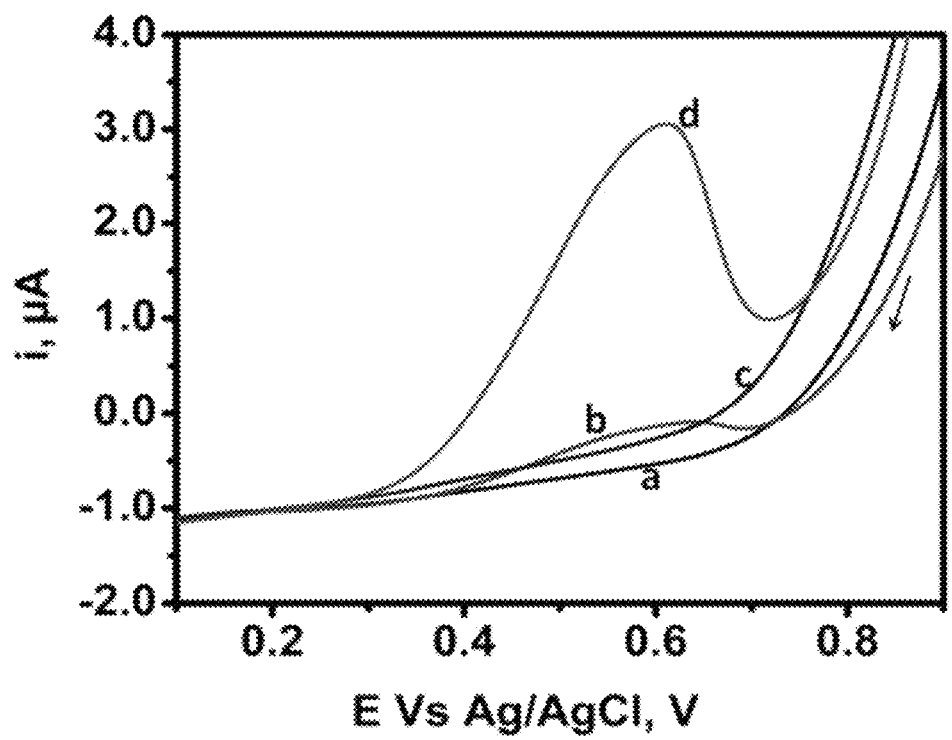
FIG. 7A shows CSLSVs for (a) 0.10 M NaOH (blank), (b) 1 mM glucose with 0.10 M NaOH. (c) 2.00 ppm Cu with 0.10 M NaOH, and (d) 1 mM glucose and 2.00 ppm Cu with 0.10 M NaOH.
Figure 7B:
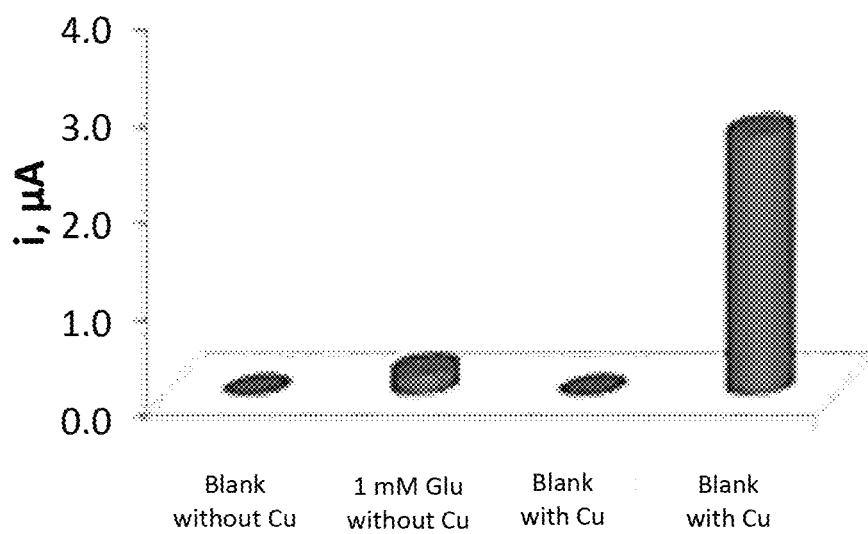
FIG. 7B shows the current peaks obtained for each sample of FIG. 7A.

Effects of Cu as an effective electro-catalyst of glucose on the surface of GPE at optimized parameters (−0.20 V accumulation potential, 60 s accumulation time, 6 mV sample interval, and 75 mV/s scan rate) for 1 mM glucose in the presence of 2.00 ppm Cu were adequately demonstrated in FIGS. 7A and 7B. Well-defined current-peaks of glucose without interference from Cu redox species were obtained. FIG. 7A curve (a) represents the voltammogram of a 0.10 M NaOH (blank glucose concentration) in absence of 2.00 ppm Cu while (b) is the corresponding voltammogram in the presence of 1 mM glucose without Cu. Curve (c) represents the voltammogram of a 0.10 NI NaOH (blank glucose concentration) in presence of 2.00 ppm Cu. A huge enhancement, greater than a 10-fold increase (>1,000%) of current-peak of (b) was observed in (d) as a result of the addition or spiking of 2.00 ppm Cu. This result shows an amazing electro-catalysis activity of Cu in 0.10 M NaOH for glucose oxidation as a potential cost saving approach for glucose sensor fabrication.

Electro-Analytical Performance

Figure 8A:
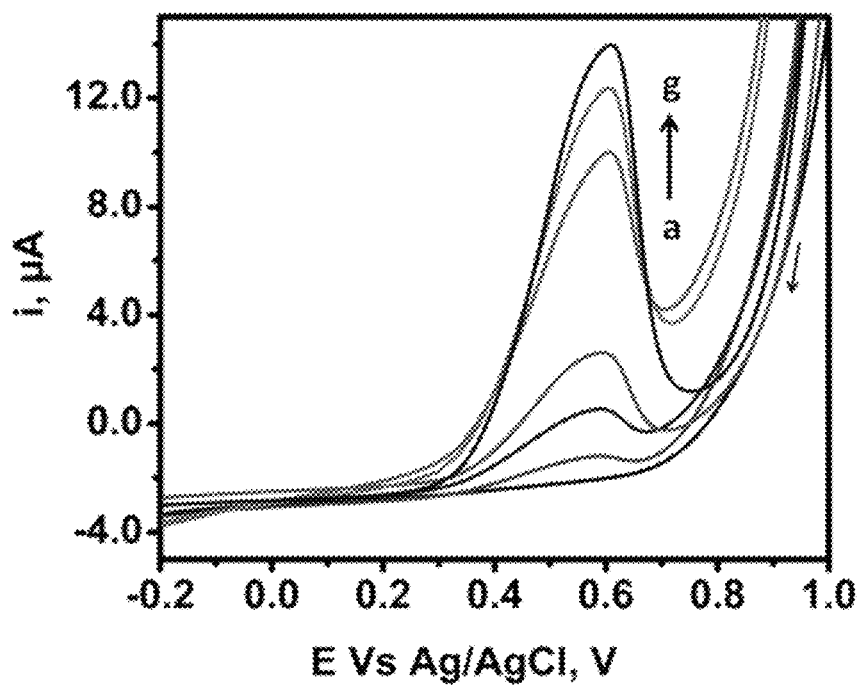
FIG. 8A shows CSLSVs in 0.10M NaOH and 2.00 ppm Cu with glucose at concentrations (mM) of (a) 0.00 (b) 0.20, (c) 0.40, (d) 1.00, (e) 2,00, (f) 3.00, and (g) 4.00.
Figure 8B:
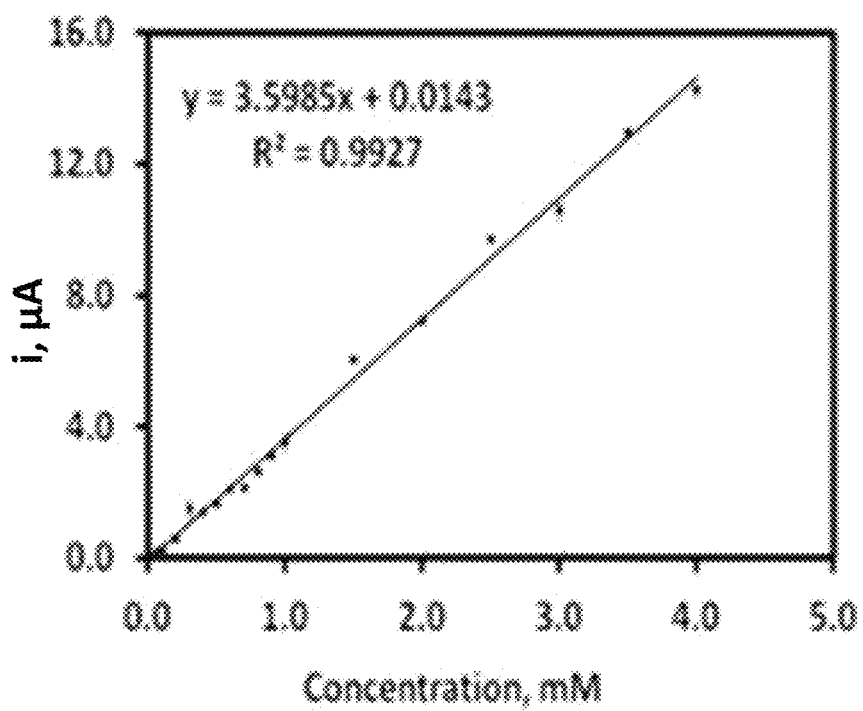
FIG. 8B shows a calibration curve constructed from the peak-currents of FIG. 8A.

CSLVs of oxidation of glucose on GPE in a medium comprising 0.10 M NaOH and 2.00 ppm Cu conditions are presented in FIGS. 8A and 8B by comparing the average values of 3 replicated successive additions of different concentrations (mM) of glucose. Response of the GPE to different concentrations of glucose can be observed from the voltammograms by the increase in the current-peak corresponding to the oxidation of glucose as the concentration of glucose increases from 0.20 to 4.00 mM as shown in FIG. 8A. This is a unique attribute for a solid electrode with no surface modification to respond to glucose oxidation in such a way. This characteristic will likely reduce the cost of sensor fabrication fix real life glucose sensing technologies.

The corresponding calibration curve for the GPE response to glucose is shown in FIG. 8B. Glucose concentration has a linear response between 0.06 mM and 4.00 mM as exhibited by the electrode by the regression equation of $i(\mu A)=3.5985C_{glu}+0.0143$, which has a correlation coefficient ($R^2$) of 0.9927 and a sensitivity of 315 $\mu A \cdot mM^{-1} \cdot cm^{-2}$. An estimated limit of detection from where a signal to noise ratio equals 3 (S/N=3) is 1.36 $\mu M$.

Performance of the sensor was found to compete favorably with previous published articles on the use of copper as an electro-catalyst for non-enzymatic glucose detection. These differences are outlined in Table 1. This performance can be attributed to simultaneous adsorption of glucose on the surface containing $Cu^+$ due to similarity in the reduction potential of $Cu^{2+}$ to $Cu^+$ and oxidation potential of glucose. This coincidence will lead to the removal of hemiacetal hydrogen atom by $Cu^+$ which is the rate determining step for electro-oxidation of glucose as predicted by Pletcher 1984. See D. Pletcher et al., incorporated herein by reference in its entirety.

potential interferences. Concentrations of AA and some other interferences are always below 0.10 mM compared to the physiological level of glucose which has been estimated

TABLE 1

Electroanalytical performance of different forms of copper modified electrodes for glucose detection

| Electrode Materials | Techniques | LOD (µM) | Linear range (mM) | Sensitivity (µA · $mM^{-1} · cm^{-2}$) | Medium | Ref.[†] |
|---|---|---|---|---|---|---|
| Bare GPE | CSLSV | 1.36 | 0.06-4 | 315 | 0.1M NaOH with Cu std solution | Present work |
| CuNcs-MWCNTs\GC | Amperometry | 1 | Up to 7.5 | 1096 | 0.1M NaOH | (a) |
| CuO-Np-CC | Amperometry | 1 | Up to 1.22 | 1245.9 | 0.1M NaOH | (b) |
| CuO-Nw-CC |  | 1 | Up to 1.12 | 2973.2 |  |  |
| CuO-Ns-CC |  | 1 | Up to 1 | 4901.9 |  |  |
| CuNps-MWCNTs\GC | Amperometry | 0.5 | 0.01-0.3 | 714 | 0.02M NaOH | (c) |
| CuNps-RGO\GC | Amperometry | 0.2 | 0.005-1.4 | 604 | 0.1M NaOH | (d) |
| CuNps-GS\GC | Amperometry | 0.5 | Up to 4.5 |  | 0.1M NaOH | (e) |
| CuNws\GC | Amperometry | 1 | Up to 3 | 420 | 0.05M NaOH | (f) |
| Cu-Psi\CP | Amperometry | 0.2 | 0.001-0.19, 0.19-2.3 | — | 0.1M NaOH | (g) |
| CuO polyhedron-Nafion\GC | Amperometry | 0.33 | Up to 4 | 1112 | 0.1M NaOH | (h) |
| CuNps\GP | DPV | 0.44 | 1-6 | 1467 | 0.1M NaOH | (i) |
| Cu-$PMo_{12}$-GR\GC | Amperometry | 0.03 | 0.001-1 | — | 0.1M NaOH | (j) |
| Cu-RGO\FP | Amperometry |  | 0.002-2, 2-13 | 50.4[a] | 0.1M NaOH | (k) |

Abbreviations:
CSLSV: cathodic sweep linear scan voltammetry;
DPV: differential pulse voltammetry;
GP: graphite pencil;
CC: carbon clothes;
GC: glassy carbon;
FP: flexible paper;
GS: graphene sheet;
RGO: reduced graphene oxide;
Psi; Porous silicon;
$PMo_{12}$: Phosphomolybdic acid;
Ns: nano sheet;
Nw: nanowire;
Np: nano particle;
[a]mA · $mM^{-1}$ · $cm^{-2}$
[†]Table 1 References:
(a) J. Yang, W.-D. Zhang, S. Gunasekaran, An amperometric non-enzymatic glucose sensor by electrodepositing copper nanocubes onto vertically well-aligned multi-walled carbon nanotube arrays, Biosensors and Bioelectronics, 26 (2010) 279-284;
(b) Y. Zhong, et al.;
(c) H.-X. Wu, W.-M, Cao, Y. Li, G. Liu, Y. Wen, H.-F. Yang, S.-P. Yang, In situ growth of copper nanoparticles on multiwalled carbon nanotubes and their application as non-enzymatic glucose sensor materials, Electrochimica Acta, 55 (2010) 3734-3740;
(d) J. Luo, H. Zhang, S. Jiang, J. Jiang, X. Liu, Facile one-step electrochemical fabrication of a non-enzymatic glucose-selective glassy carbon electrode modified with copper nanoparticles and graphene, Microchimica Acta, 177 (2012) 485-490;
(e) J. Luo, et al.;
(f) Y. Zhang, L. Su, D. Manuzzi, H.V.E. de los Monteros, W. Jia, D. Huo, C. Hou, Y. Lei, Ultrasensitive and selective non-enzymatic glucose detection using copper nanowires, Biosensors and Bioelectronics, 31 (2012) 426-432;
(g) A.A. Ensafi, et al.;
(h) C. Kong, et al.;
(i) S. Pourbeyram, et al.;
(j) J. Xu, et al.;
(k) B. Wang, et al., each incorporated herein by reference in their entirety.

Potential Interference from other Compounds on Glucose Detection

Figure 9A:
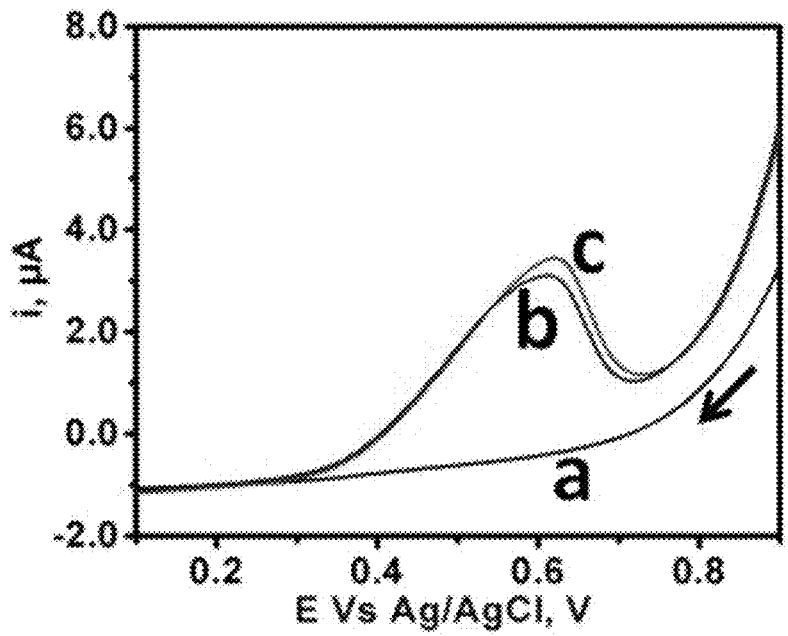
FIG. 9A shows CSLSVs of 0.1 M NaOH and 2.00 ppm Cu and (a) with 0.10 mM ascorbic acid, (b) 0.10 mM ascorbic acid and 1 mM glucose, or (c) 1 mM glucose.
Figure 9B:
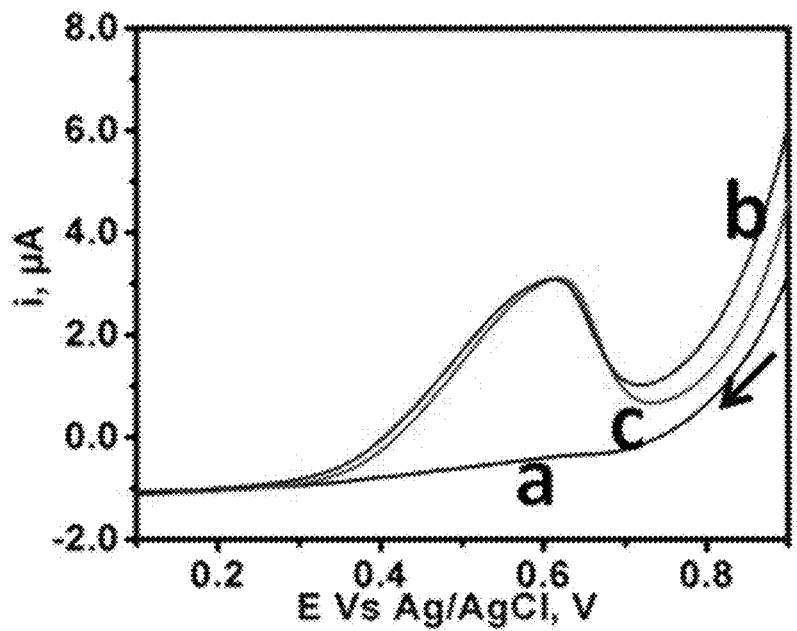
FIG. 9B shows CSLSVs of 0.1 M NaOH and 2.00 ppm Cu and (a) with 0.10 mM fructose, (b) 0.10 mM fructose and 1 mM glucose, or (c) 1 mM glucose.
Figure 9C:
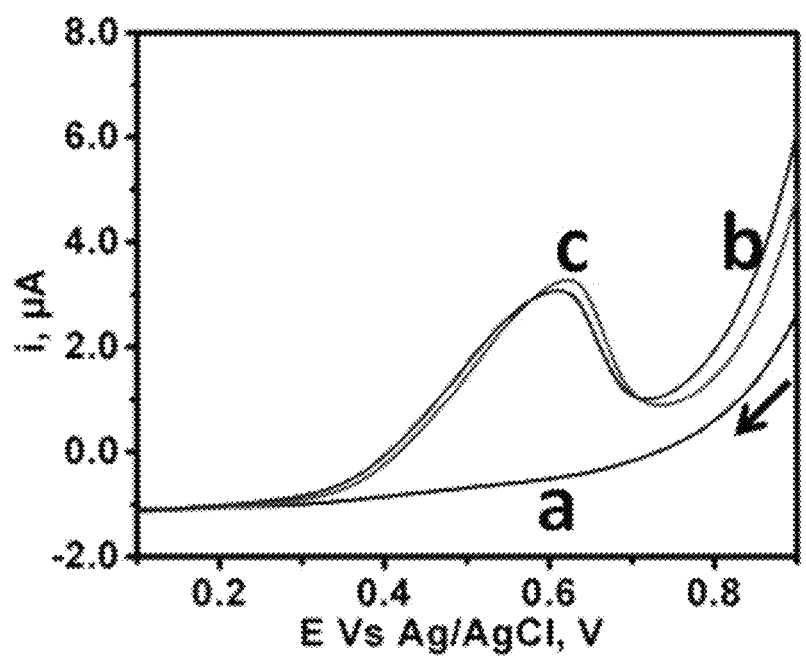
FIG. 9C shows CSLSVs of 0.1 M NaOH and 2.00 ppm Cu and (a) with 0.10 mM alanine, (b) 0.10 mM alanine and 1 mM glucose, or (c) 1 mM glucose.

The co-existence of some saccharides (such as fructose), amino acids (such as alanine) and ascorbic acid (AA), along with glucose in real life samples necessitate the investigation to prove the potency of the sensor in the presence of these to be between 3.00 to 8.00 mM. See Z. Zhuang, X. Su, H. Yuan, Q. Sun, D. Ciao, M. M. F. Choi, An improved sensitivity non-enzymatic glucose sensor based on a CuO nanowire modified Cu electrode, Analyst, 133 (2008) 126-132, incorporated herein by reference in its entirety. Base the physiological ratio of glucose to its potential interferences, 0.10 mM of AA (FIG. 9A), fructose (FIG. 9B) and alanine (FIG. 9C) were used as an interference concentration against 1 mM glucose. Cathodic sweep LSV of 0.10 mM of AA, fructose, and alanine in the absence of 1 mM glucose are represented by FIG. 9A (a), FIG. 9B (a), and FIG. 9C (a), respectively. It can be observed that none of the interference current-peak signal was bund around the electro-decomposition potential of glucose in the absence of any interference presented by FIG. 9A (b), FIG. 9B (b) and. FIG. 9C (b). Addition of 1 mM glucose into the solution containing 0.10 mM AA, fructose, and alanine (FIG. 9A (c), FIG. 9B (c), and FIG. 9C (c), respectively) show no significant change in the current-peak when compared with the current peak of glucose in the absence of interferences. Apart from a slight change in background noise of the current-peak which does not significantly affect the current-peak of 1 mM glucose, percentage increase in 1 mM glucose current peaks as a result of all the study interference are not more than 5%. The interference study confirms the capability of GPE as a potential transducer for glucose sensor in the presence of potential interferences.

Voltammetric Determination of Glucose in Serum Sample

Developed technique was tested on the serum sample obtained from a healthy patient in King Fand University Teaching Hospital. Protein-free serum sample diluted 200 times in 0.10 M NaOH was used for analysis of glucose by spiking of a series of glucose standard solutions. Results of the serum sample analysis are enumerated in Table 2. About 0.04 mM glucose concentration equivalent to about 8.00 mM glucose concentration in the undiluted serum was found with a good recovery range between 97-110%. This performance is an indication of the capability of the developed technique with bare GPE in the presence of Cu for a real life application.

A unique and cost effective voltammetric technique for the development of a non-enzymatic glucose sensor by in-situ reduction of $Cu^{2+}$ to $Cu^+$ and electrochemical oxidation of glucose on the surface of graphite pencil electrode (GPE) was proposed. Adsorbed $Cu^+$ on GPE was characterized with flame emission scanning electron microscope-electron dispersed X-ray (FESEM-Edx) and X-ray spectroscopy (XPS). Electro-catalytic property of copper (Cu) was explored to enhance the secondary oxidation current-peak of glucose at about 0.63 V to more than 10 fold (>1,000%) in 0.1 M NaOH solution. Linearity dependence of the electrode was determined as $i(\mu A)=3.5985C_{glu}+0.0143$ for 0.06-4.0 mM concentration of glucose with a correlation coefficient ($R^2$) of 0.9927, sensitivity of 315 $\mu A \cdot mM^{-1} \cdot cm^{-2}$, and limit of detection (S/N=3) of 1.36 $\mu M$. Developed technique is an inexpensive and competent method for the development of a non-enzymatic glucose sensor for human fluid samples due to almost no interference of L-ascorbic acid (AA), alanine, and fructose with the current-peak of glucose.

TABLE 2

Glucose detection in healthy human serum sample

| # | Spiked Amount (mM) | Amount Found (mM) | Amount Recovered (mM) | % Recovery |
|---|---|---|---|---|
| 1 | 0.50 | 0.04 | 0.49 | 97.00 |
| 2 | 1.00 | 0.04 | 1.01 | 101.30 |

TABLE 2-continued

Glucose detection in healthy human serum sample

| # | Spiked Amount (mM) | Amount Found (mM) | Amount Recovered (mM) | % Recovery |
|---|---|---|---|---|
| 3 | 1.50 | 0.04 | 1.52 | 101.56 |
| 4 | 2.00 | 0.04 | 1.98 | 98.98 |

EXAMPLE 3

Materials And Methods For Methionine Detection
Chemicals 1000 mg/L±4.00 Ag standard was prepared in nitric acid having a AAS specification from Fluka. NaOH pellets, DL-methionine, L-ascorbic acid, L-alanine, and L-cysteine were supplied by Sigma-Aldrich. For the supporting electrolyte, phosphate buffer solution, pH 7.00, 0.10 M, was prepared by mixing appropriate volumes of 0.20 M monosodium phosphate and disodium phosphate prepared with double distilled water and sodium acetate. These salts were all used as collected from Sigma-Aldrich. All solutions were prepared with double distilled water obtained from AQUA-TRON water still A4000D water purification system.

Electrochemical Cell and Procedure

A system comprising 3 electrodes was utilized with 0.10 M NaOH and phosphate buffer solution (PBS) as supporting electrolyte. PBS was prepared with appropriate mixture of sodium phosphate mono and di-basic anhydrous salts. The working electrode is a graphite pencil lead whose fabrication, description, and working principle have been widely reported previously, See J. Wang, A. -N. Kawde, Pencil-based renewable biosensor for label-free electrochemical detection of DNA hybridization, Anal. China. Acta 431 (2001) 219-224, incorporated herein by reference in its entirety. Platinum wire and Ag/AgCl saturated KCl were connected with CHI potentiostat workstation (CHI1140A, CH Instruments Inc, Austin, Tex., USA) as counter and reference electrodes, respectively, for all electroanalytical measurements. Approximately 10 am length of 0.50 mm diameter graphite lead corresponding to about 16.10 mm$^2$ surface area was propelled out of a vertically positioned pencil through a TEFLON hole to make contact with the supporting electrolyte. Electrical contact of the graphite lead was achieved by soldering copper wire with the metallic part of the pencil.

Electroanalytical techniques adapted for the electrochemical studies are cyclic voltammetry and linear scan voltammetry (CSLSV) for the analytical performance of the developed technique at room temperature and cathodic sweeping at quiescent condition.

Surface Characterization of GTE

Images of GPE were recorded by FE-SEM by a TESCAN LYRA 3 instrument from the Center of Research Excellence in Nanotechnology ((ENT), King Fand University of Petroleum and Minerals (KFUPM), Kingdom of Saudi Arabia (KSA). X-ray photon Spectroscopy (XPS) investigation was performed with Thermo-Scientific ESCALAB-250Xi instrument with monochromatic Al Kα radiation (hv=1486.6 eV) installed in the Physics Department of KFUPM, KSA. Data obtained from XPS were processed with Thermo Advantage version 5.51, Surface Chemical Analysis software.

Real Sample (Serum) Preparation

The collection of the serum sample from a healthy patient was achieved with the assistance of Imam Abdulrahman University Teaching Hospital's blood bank section (King Fahd University, Hospital). The serum sample was stored in the refrigerator to defrost, and a 450 µL aliquot was taken and treated with methanol (900 µL) in a 1:2 volume ratio to separate the protein from the serum sample. The precipitated protein was separated by centrifuging the mixture for 20 minutes at 2000 rpm, decanting, and subsequently filtering the clear supernatant with a Millipore filter having a 0.45 µm pore size.

EXAMPLE 4

Figure 10A:
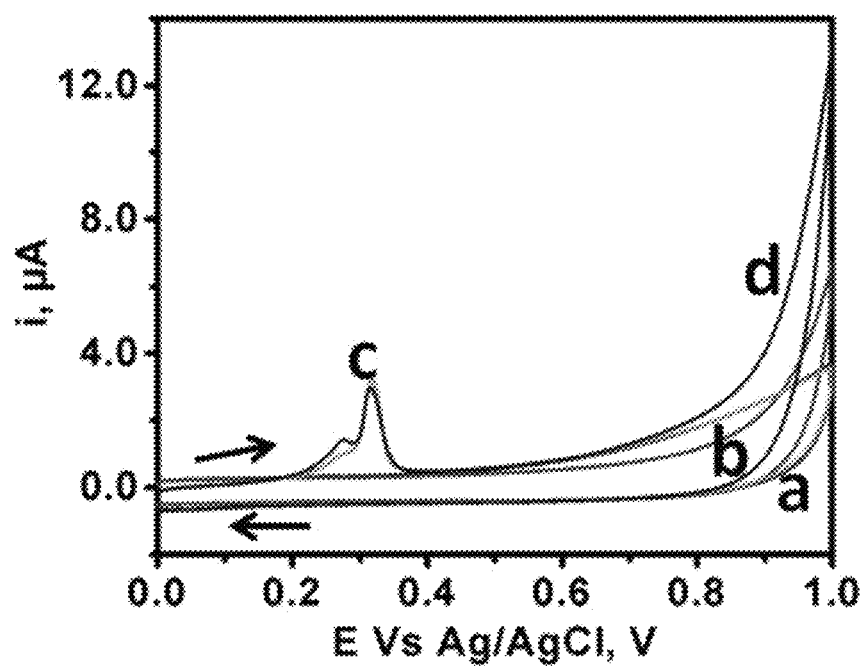
FIG. 10A shows CVs of a GPE in 0.10 M phosphate buffer solution (PBS) pH 7.00±0.20 as (a) a blank, (b) with 0.50 mM DL-methionine, (c) with 5 ppm Ag, or (d) with both 0.50 mM DL-methionine and 5 ppm Ag.
Figure 10B:
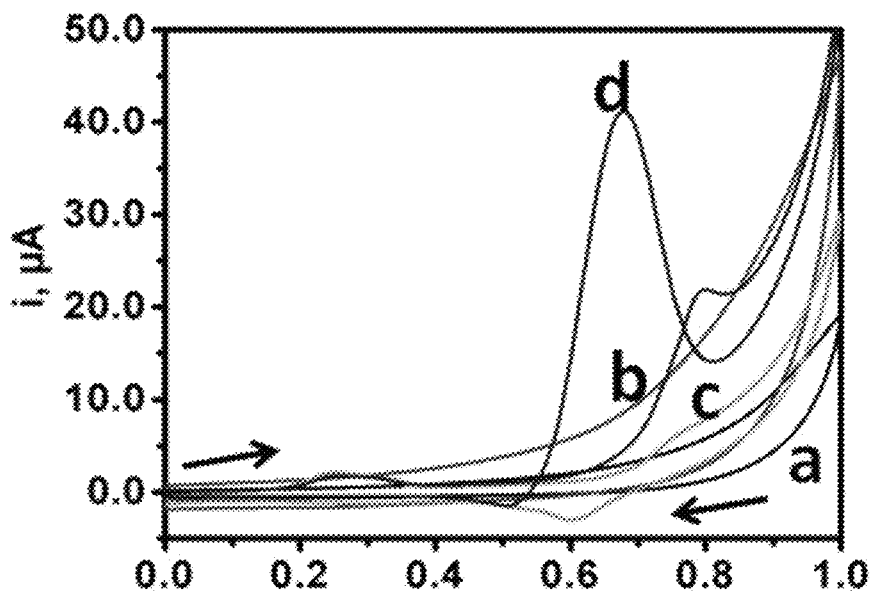
FIG. 10B shows CVs of a GPE in 0.1M NaOH pH 13.70±0.20 as (a) a blank, (b) with 0.50 mM DL-methionine, (c) with 5 ppm Ag, or (d) with both 0.50 mM DL-methionine and 5 ppm Ag.

Results and Discussion for Methionine Detection
Effect of Buffer on Methionine Redox Reactions on GEE Cyclic voltammograms (CVs) showing the redox reaction of methionine in 0.1 M PBS pH 7.00±0.20, and 0.10 M NaOH pH 13.70±0.20, are shown in FIGS. 10A and 10B, respectively. It can be observed that the presence of 0.50 mM methionine in FIG. 10A "b" and FIG. 10B "b" could not generate any redox peaks when compared with their corresponding FIG. 10A "a" and FIG. 1B "a" which represent the CV of 0.10 M PBS pH 7.00±0.20 and 0.10 M NaOH pH 13.70±0.2 without methionine, respectively. A peak attributed to the oxidation of $Ag^0$ to $Ag^+$ between 0.20 and 0.40 V as reported by Wan et al. 2013 can be observed in FIG. 10A "c" and FIG. 10B "c" due to the presence of 5 ppm $AgNO_3$ solution in the electrolyte. See Y. Wan, X. Wang, S. Liu, Y. Li, H. Sun, Q. Wang, Effect of Electrochemical Factors on Formation and Reduction of Silver Oxides, Int. J. Electrochem. Sci. 8 (2013) 12837-12850, incorporated herein by reference in its entirety. Addition of 0.50 mM methionine into PBS containing 5 ppm $AgNO_3$ solution could not generate an additional peak for methionine as shown in FIG. 10A "d." Surprisingly, a very sharp secondary oxidation peak can be observed in FIG. 10B "d" as a result of the addition of 0.50 mM methionine to NaOH electrolyte containing 5 ppm $AgNO_3$ solution. So, oxidation of methionine on the surface of GPE can only be initiated by the presence $AgNO_3$ in NaOH electrolyte but not in PBS solution. A characteristic peak of the oxidation of $Ag^+$ to $Ag^{2+}$ at about 0.80 V as shown in FIG. 10B "c" can be responsible for the oxidation of methionine. This observation can be supported by a pulse radiolysis investigation reported for $Ag^{2+}$ in metal-induced oxidation of methionine by hydroxyl radical ($OH^-$): a readily available mechanism which generates a sulphonium center (Zwitterionic methionine) as an intermediate in both cyclic of aliphatic depending on pH and can later oxidize to methionine sulphoxide. See K. O. Hiller, B. Masloch, M. Göbi, K. D. Asmus, Mechanism of the OH- radical induced oxidation of methionine in aqueous solution, J. Am. Chem. Soc. 103 (1981) 2734-2743; and K. O. Hiller, K. D. Asmus, $Tl^{2+}$ and $Ag^{2+}$ Metal-ion-induced Oxidation of Methionine in Aqueous Solution. A Pulse Radiolysis Study, Int. J. Radiat. Biol. 40 (1981) 597-604, each incorporated herein by reference in their entirety.

Figure 11A:
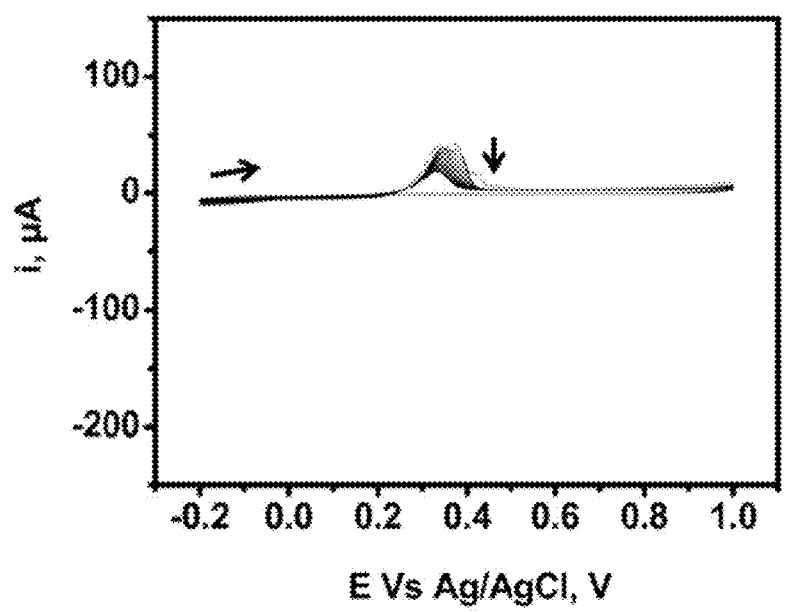
FIG. 11A shows a cyclic voltammogram with 25 voltage sweeps with the GPE in 5 ppm $AgNO_3$ and 0.10 M PBS pH 7.00±0.20.
Figure 11B:
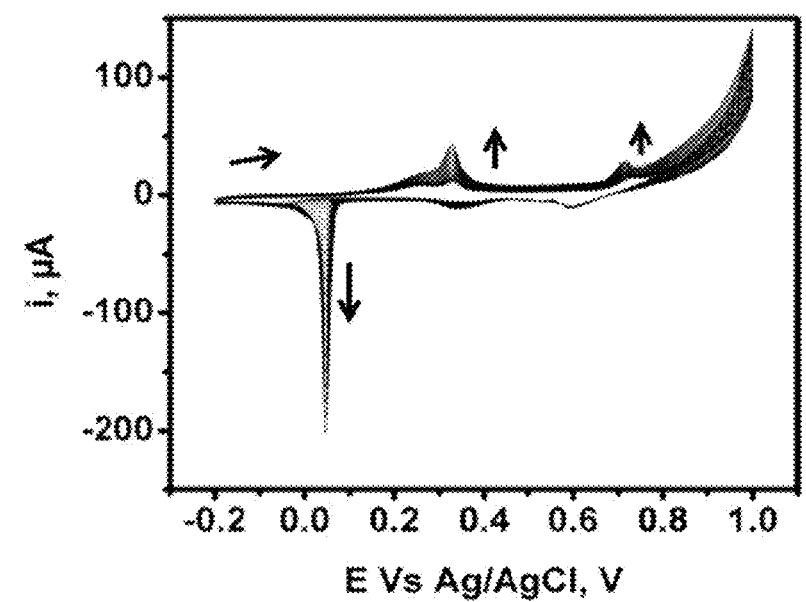
FIG. 11B shows a cyclic voltammoarram with 25 voltage sweeps with the GPE in 5 ppm $AgNO_3$ and 0.1M NaOH pH 13.70±0.20.

Electrochemical redox reaction of $AgNO_3$ on the surface of GPE was further studied in PBS and NaOH electrolyte by multiple cycle CV. FIGS. 11A and 11B represent 25 cycles of 5 ppm $AgNO_3$ solution in PBS and NaOH, respectively. The current attributed to oxidation of $Ag^+$ to $Ag^{2+}$ was only observed in FIG. 11A with a reduced current peak after the first cycle of CV. However, apart from the $Ag^+$ to $Ag^{2+}$ oxidation peak observed in FIG. 11A, an additional oxidation peak and about 3 reduction peaks were observed in FIG. 11B with an increase in peak current of each peak as the CV cycles increased. This redox behavior suggests that the property of a pure silver sample has been successfully induced on the surface of GPE based on the report of the formation and reduction of different silver oxides (AgOs) in NaOH electrolyte when 99.99% silver sample was used as a working electrode. This also suggests that there is propagation in the formation of Ag oxide layers as the number of cycles increases by OW from NaOH of the supporting electrolyte. See Y. Wan et al., incorporated herein by reference in its entirety.

Characterization of GPE Surface FE-SEM and EDX Analysis

Figure 12A:
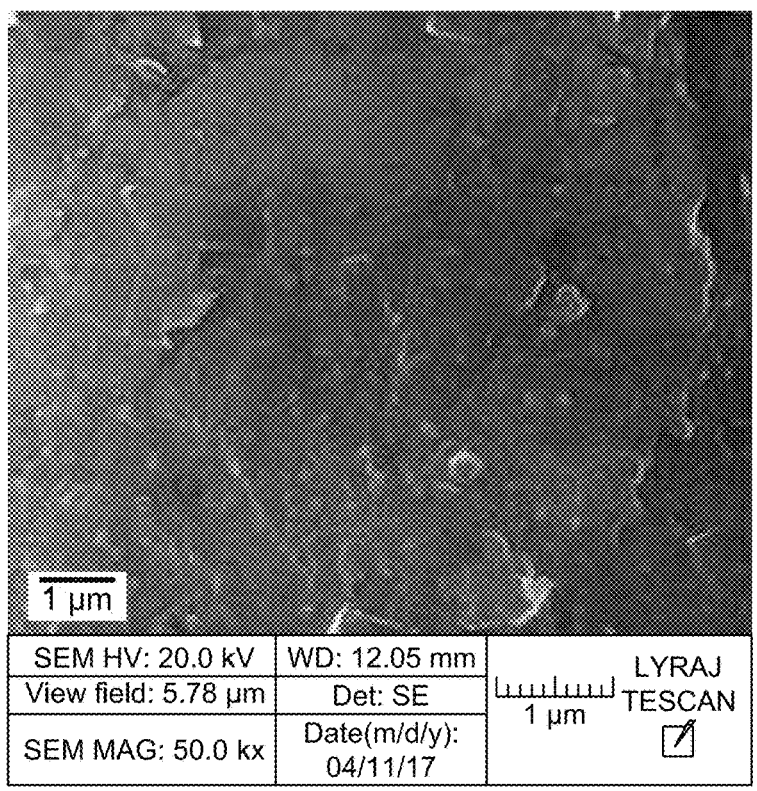
FIG. 12A is an FE-SEM image of a GPE surface before any CV measurement.
Figure 12B:
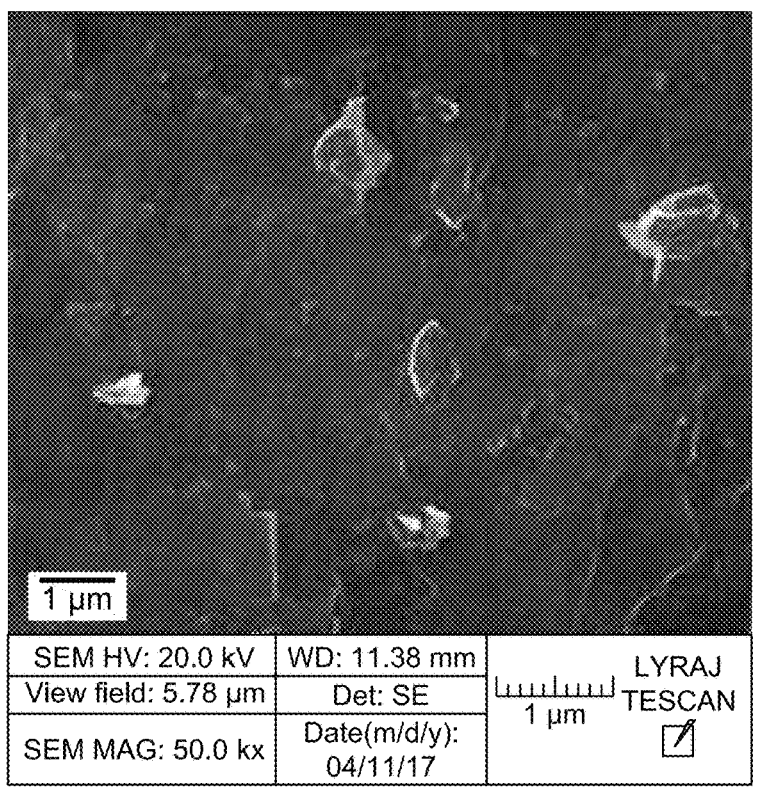
FIG. 12B is an FE-SEM image of a GPE surface after 25 cycles of CV in 0.10 M PBS pH 7.00±0.20.
Figure 12C:
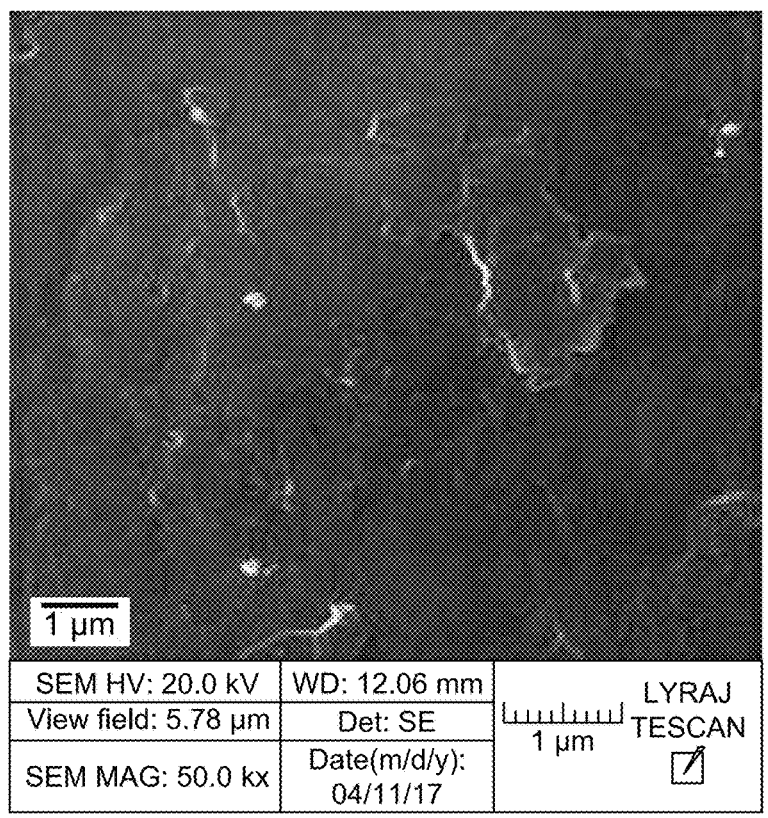
FIG. 12C is an FE-SEM image of a GPE surface after 25 cycles of CV in 0.10 M NaOH.
Figure 12D:
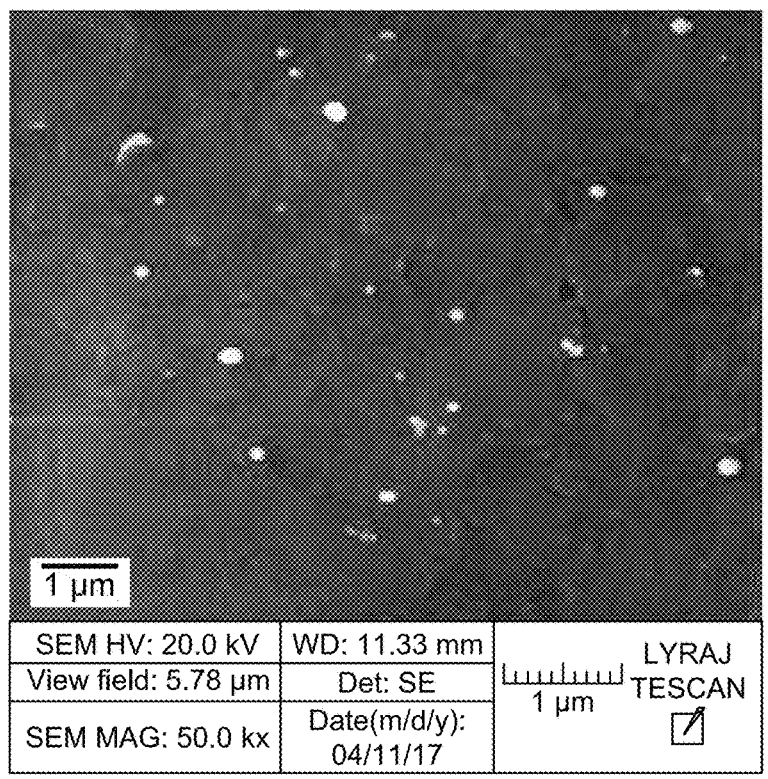
FIG. 12D is an FE-SEM image of a GPE surface after 25 cycles of CV in PBS with 5 ppm $AgNO_3$.
Figure 12E:
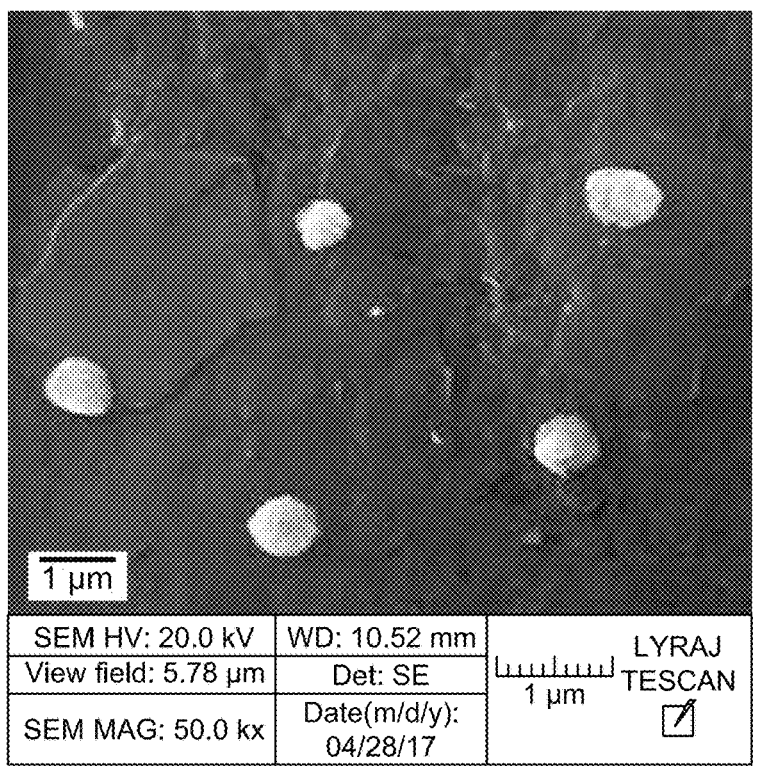
FIG. 12E is an FE-SEM image of a GPE surface after 25 cycles of CV in 0.10 M NaOH pH 13.70±0.20 with 5 ppm $AgNO_3$.
Figure 12F:
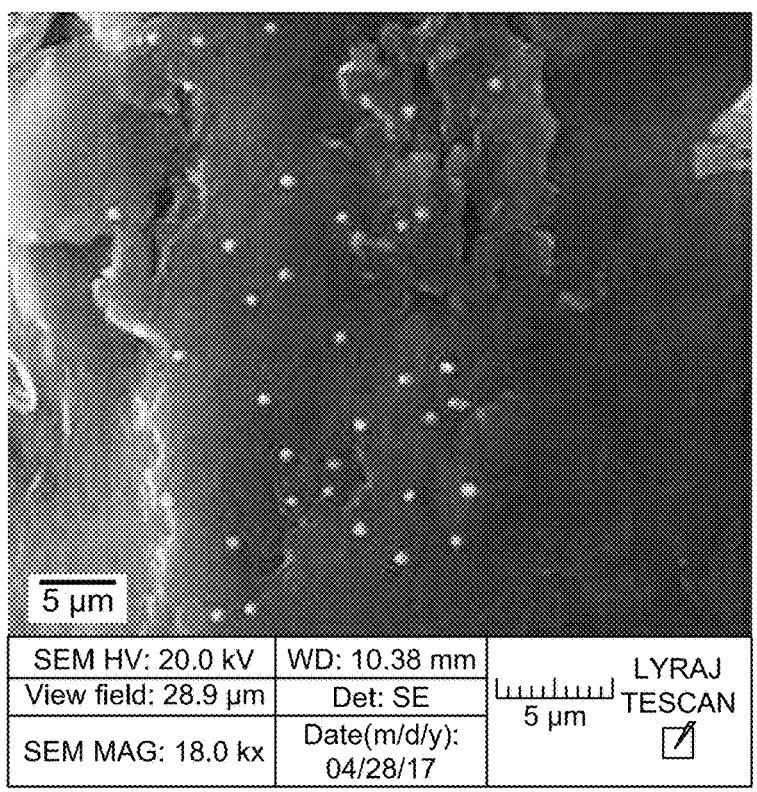
FIG. 12F is an FE-SEM image of the sample in FIG. 12E, taken at a lower magnification.

Effects of the oxides layers on the surface of GPE (FIGS. 12A-12F) were further investigated by FE-SEM/EDX analysis after 25 cycles CV. FIGS. 12A, 12B, and 12C show the image of GPE, GPE in 0.10 M PBS, and GPE in NaOH in absence of $AgNO_3$ solution, respectively. Formation of spherical shape Ag oxides can be observed in FIGS. 3D and 3F on the GPE surface with 5 ppm $AgNO_3$ in PBS or NaOH, respectively. By comparison, the formation of Ag is more obvious in NaOH than in PBS medium. EDX spectra (Figure not shown) of the images further confirmed the presence of Ag on the GPE in both media with a greater weight % observed for the NaOH sample.

Characterization of GPE Surface XPS Analysis

Figure 13A:
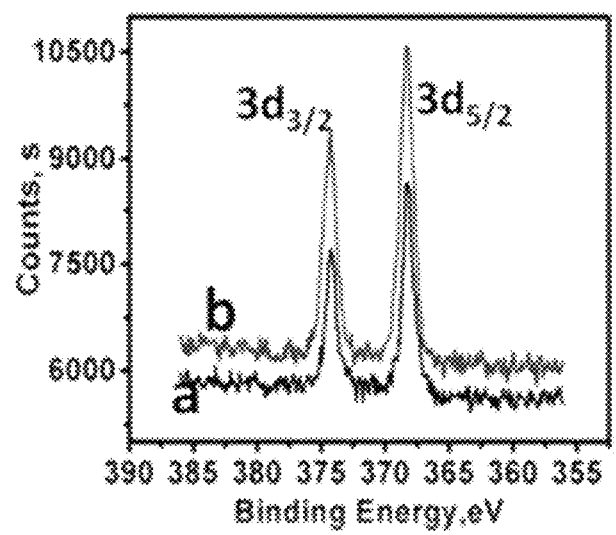
FIG. 13A is an XPS analysis of Ag 3d on DGLPE surface after 25 cycles of CV in 5 ppm $AgNO_3$ with (a) 0.10 M PBS pH 7.00±0.20 or (b) 0.10 M NaOH pH 13.70±0.20.
Figure 13B:
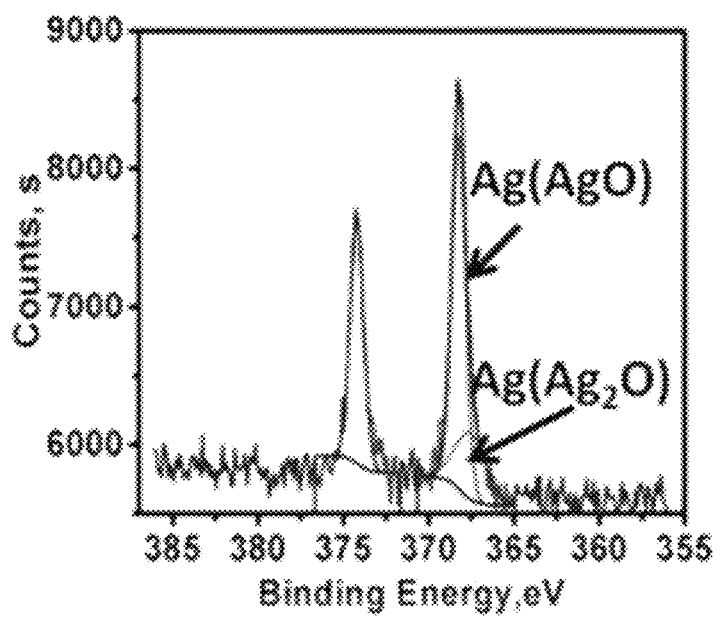
FIG. 13B is a deconvolution of curve (a) in FIG. 13A.
Figure 13C:
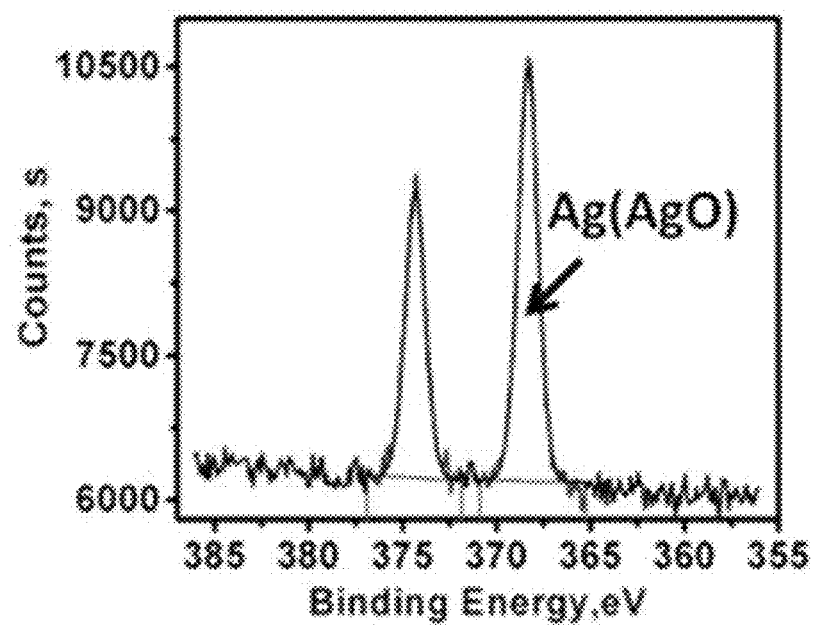
FIG. 13C is a deconvolution of curve (b) in FIG. 13A.
Figure 13D:
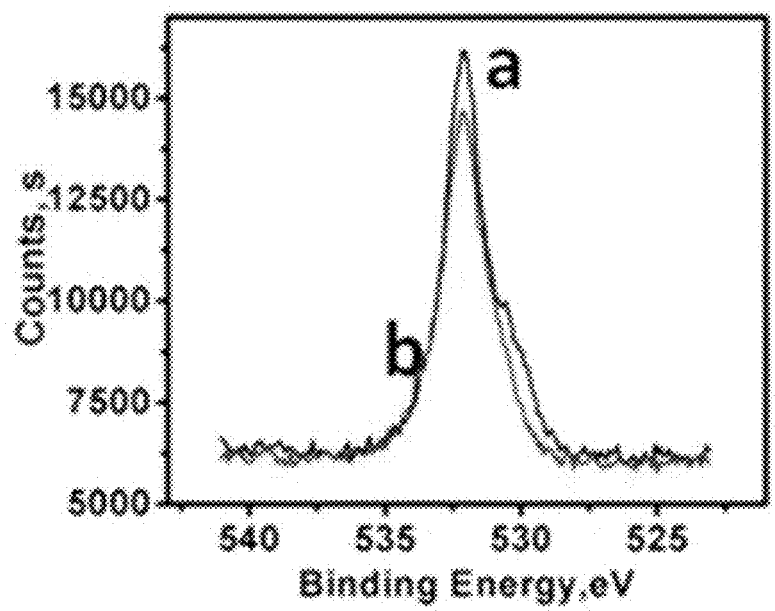
FIG. 13D is an XPS analysis of O 1 s on DGLPE surface after 25 cycles of CV in 5 ppm $AgNO_3$ with (a) 0.10 M PBS pH 7.00±0.20 or (b) 0.10 M NaOH pH 13.70±0.20.
Figure 13E:
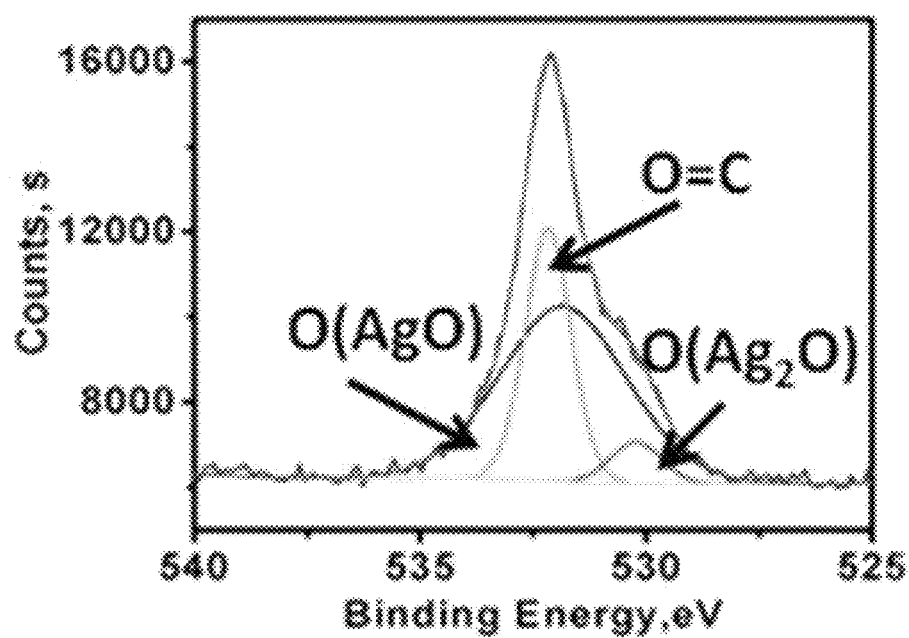
FIG. 13E is a deconvolution of curve (a) in FIG. 13D.
Figure 13F:
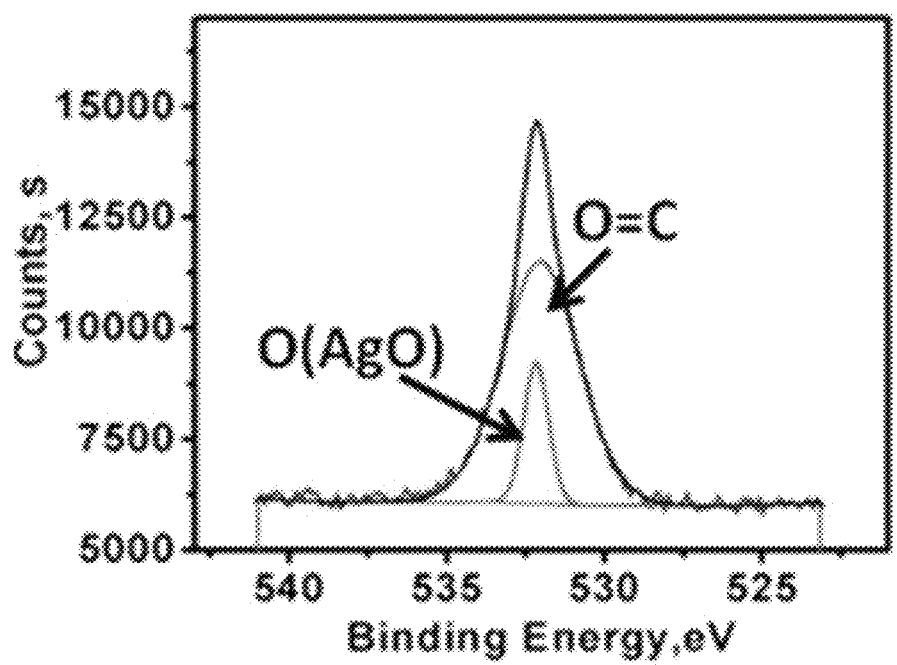
FIG. 13F is a deconvolution of curve (b) in FIG. 13D.

Investigation of the oxidation states of Ag presence on GPE surface 5 ppm $AgNO_3$ in 0.10 M PBS and NaOH by XPS Ag 3d and O 1 s spectra are presented in FIGS. 13A-13F. Two characteristic peaks of AL, indicated as $3d_{3/2}$ and $3d_{5/2}$ can be observed at about 374 eV and 368 eV binding energy (BE) respectively in both media, but with higher intensity in NaOH (FIG. 13A (b)) than in PBS (FIG. 13A (a)), confirming the presence of Ag on the GPE surface with different oxidation states. Further analysis of FIG. 13A as show in FIG. 13B and FIG. 13C for PBS and NaOH media, respectively, reveal the presence of additional peak of lower intensity in $3d_{5/2}$ with BE of 367.56 eV while there are no additional peaks observed in the analysis of (b) from FIG. 13A. This observation is an indication of the presence of Ag in $Ag_2O$ along with Ag in AgO with FIG. 13A confirming the dominance of $Ag_2O$ on the surface of GPE in PBS medium and AgO on the surface of GPE in NaOH medium. Sec G. B. Hoflund, Z. F. Hazos, G. N. Salaita, Surface characterization study of Ag, AgO, and $Ag_2O$ using X-ray photoelectron spectroscopy and electron energy-loss spectroscopy, Phys. Rev. B 62 (2000) 11126; and R. Rebelo, S. V. Calderon, R. Fangueiro, M. Henriques, S. Carvalho, Influence of oxygen content on the antibacterial effect of Ag—O coatings deposited by magnetron sputtering, Surf and Coat. Technol. 305 (2016) 1-10, each incorporated herein by reference in their entirety. This behavior was further observed in O 1 s spectra (FIG. 13D) with the appearance of a hump on the O 1 s spectrum ((a) of FIG. 13D) of the PBS medium compared with O1 s spectrum of the NaOH sample ((b) in FIG. 13D). Analysis of FIG. 13D presented as FIG. 13E for the PBS medium reveal an extra peak with 530.22 eV BE, showing the presence of O in $Ag_2O$ in the PBS medium and O of AgO in the NaOH medium (FIG. 13F), Both Ag 3d and the O 1 s spectra complement each other as proof for the deposition of AgO on GPE in NaOH and $Ag_2O$ an GPE in PBS medium with a common O=C peak at about 532 eV for graphite attachment with the O of the oxides in both spectra. See B. V. Crist, Handbooks of monochromatic XPS spectra, XPS International, 1999. incorporated herein by reference in its entirety.

Effect of Ag Concentration on Methionine Oxidation

Figure 14A:
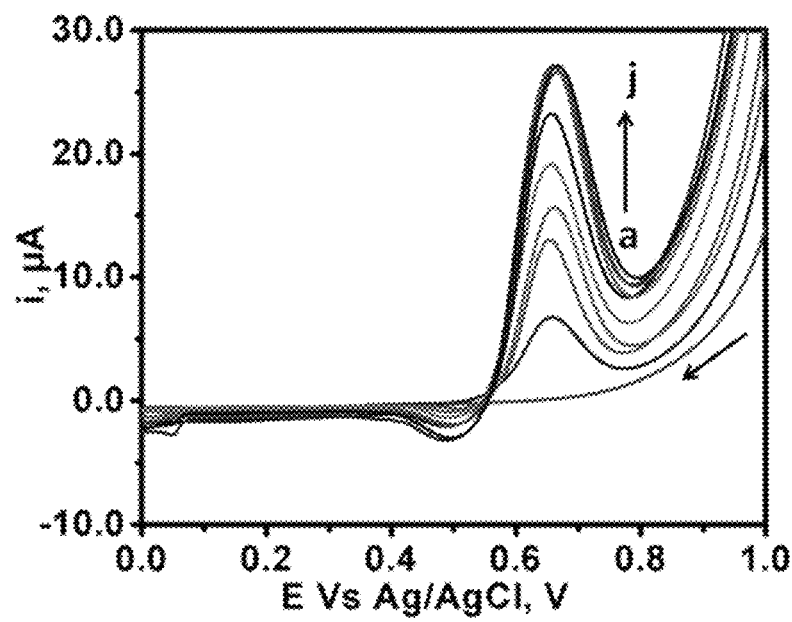
FIG. 14A shows CSLSVs of 0.20 mM DL-methionine in 0.10 M NaOH pH 13.70±0.20 and with different concentration of Ag (ppm): (a) 0.0 (blank), (b) 0.50, (c) 1.00, (d) 1.50, (e) 2.00, (f) 2.50, (g) 3.00. (h) 4.00, (i) 5.00, and (j) 6.00.
Figure 14B:
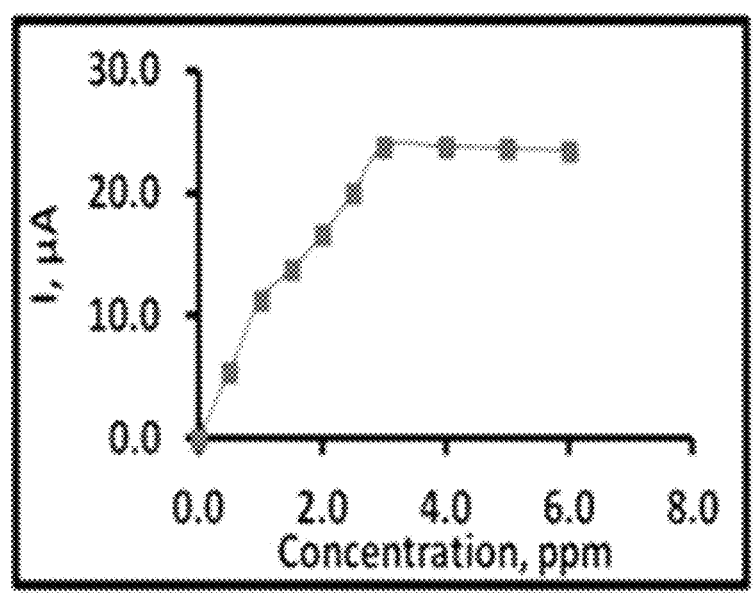
FIG. 14B is a plot of the peak current values observed for each Ag concentration in FIG. 14A.
Figure 15A:
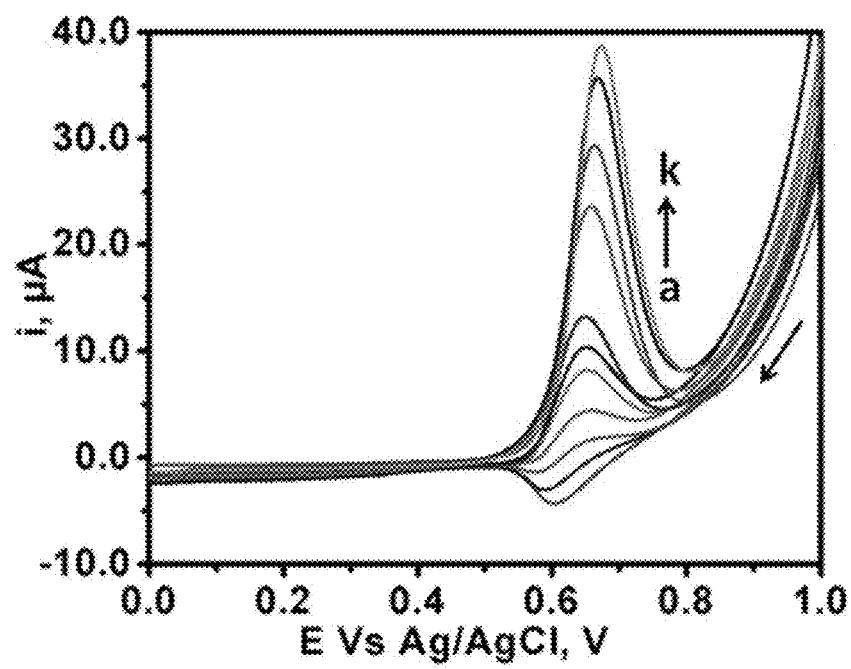
FIG. 15A shows cathodic sweep linear scan voltammograms of a GPE in 0.10 M NaOH pH 13.70±0.20 plus 3.00 ppm $AgNO_3$ with the following concentrations of DL-methionine (mM): (a) 0.00, blank, (b) 0.01, (c) 0.02, (d) 0.04, (e) 0.06, (0 0.08, (g) 0.10, (h) 0.20, (i) 0.30, (j) 0.40, and (k) 0.50.

Based on the redox peaks of Ag on the GPE surface and the oxidation of methionine in the cathodic region of the CVs shown in FIG. 10B, cathodic sweep linear sweep voltammetry (CSLSV) was used for subsequent electrochemical investigations. An amount of $AgNO_3$ solution necessary for effective oxidation of methionine needs to be determined. Effect of $AgNO_3$ solution on the oxidation of 0.20 mM methionine is presented in FIGS. 14A-14B. Oxidation of methionine could not be noticed in (a) of FIG. 14A due to the absence of $AgNO_3$ solution. However, introduction of $AgNO_3$ solution into the medium containing 0.10 M NaOH and 0.20 mM methionine leads to emergence of oxidation peaks of methionine around 0.65 V along with 2 reduction peaks of Ag at about 0.50 V and 0.05 V. It was observed that the peak current increases as the concentration of the $AgNO_3$ solution increases from 0.50 ppm (b) to 3.00 ppm (g). Peak current response of methionine to subsequent addition of $AgNO_3$ solution was shown in a corresponding bar chart of the voltammogram presented in FIG. 14B. Concentrations of $AgNO_3$ solution above 3 ppm do not show significant difference in peak current with 0.20 mM methionine (curves (h) to (j) of FIG. 14A). This could be as a result of the agglomeration of the Ag particles formed on the GPE surface, which may likely reduce or slow down the oxidation process. The concentration of $AgNO_3$ solution that can effectively initiate oxidation of methionine was considered to be 3 ppm Electro-Analytical Performance Performance of the developed sensor was ascertained by constructing a calibration curve (FIG. 15B) from mean values of 3 voltammograms replicated with successive additions of methionine while retaining 0.10 M NaOH and 3 ppm $AgNO_3$ (FIG. 15A). A characteristic reduction peak of $Ag^{2+}$ to $Ag^+$ responsible for the initiation of methionine oxidation, similar to what was observed in FIG. 11B between 0.70 V and 0.60 V, can be observed in (a) of FIG. 15A in the absence of methionine. Possible conversion of $Ag^+$ to $Ag^{2+}$ in the supporting electrolyte by the initial applied 0.20 V accumulation potential for 30 s can be attributed to CSLSV response to the reduction peak by GPE. This peak can still be observed despite addition of 0.01, 0.02, and 0.04 mM of methionine producing an oxidation peak with a deflection around 0.65 V potential in (b), (c), and (d), respectively, of FIG. 15A. Moreover, as the concentration of methionine increases from 0.06 to 0.50 mM as shown in (e) to (k) of FIG. 15A, the Ag reduction peak is no longer observed due to relatively higher current generated by oxidation of methionine on the GPE surface.

Figure 15B:
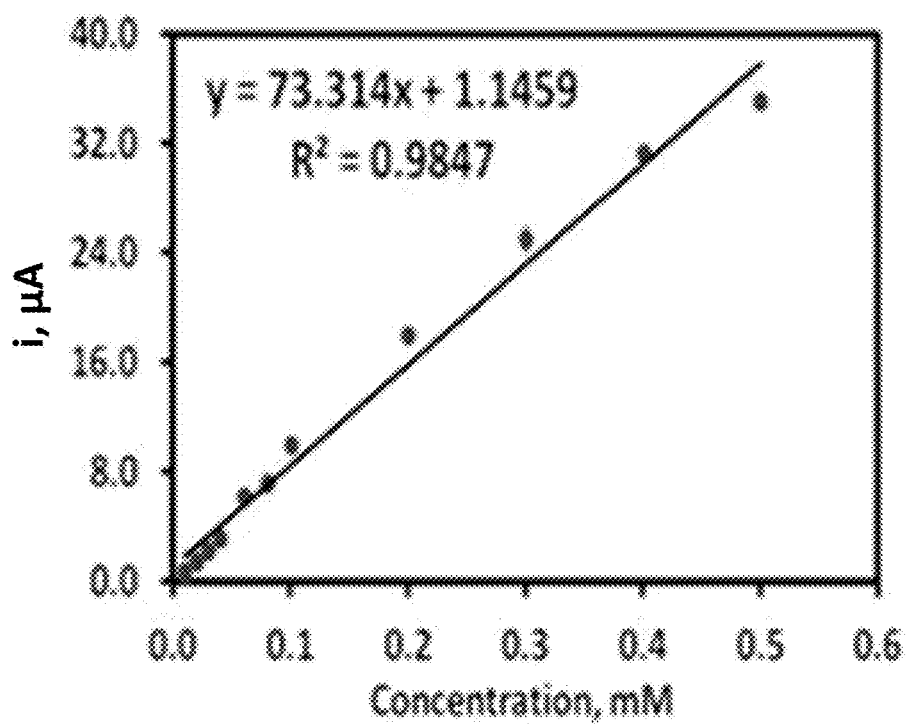
FIG. 15B shows the calibration curve produced from the peak current values of FIG. 15A.

A calibration curve for the corresponding voltammograms of methionine is shown in FIG. 15B. The observed current has a linear dependence on methionine concentration between 0.01 mM and 0.50 mM methionine as defined by the equation i(μA)=73.314 $C_{DLM}$+1.1459 with a correlation coefficient ($R^2$) of 0.9847 and sensitivity of 4553.66 μA·mM$^{-1}$·cm$^{-2}$. Limit of quantification (LOQ) is 10 μM with an estimated limit of detection (LOD) of 0.04 μM using a signal to noise ratio of 3 (S/N=3). The performance of the sensor was found to compete favorably as enumerated in Table 3 with previously published articles on different chemically-modified electrodes for methionine detection.

TABLE 3

Performance Comparison of Different Modified Electrode with GPE in the Presence of $AgNO_3$ for Methionine Determination.

| Transducer | Medium | Technique | LOD (μM) | Linear Range (μM) | Ref†† |
| --- | --- | --- | --- | --- | --- |
| Ru-Metden/CtCE | 0.1 M PBS, pH 7.0 | Amperometry | 0.60 | 1-10 | (a) |
| CAu-Cystm/CPE | 0.1 M PBS, pH 7.0 | DPV | 0.56 | 1-100 | (b) |
| Ni-P/CCE | 0.1 M NaOH | Ch-Amp | 2 | 2-90 | (c) |
| Fullerene-$C_{60}$/AuE | 0.1 M $KNO_3$ | HDV | 8.2 | Up to 100 | (d) |
| SPGME | 0.1 M PBS, pH 7.0 | DPV | 95 | 50-5000 | (e) |
| p-4α-$Cu^{II}$TAPc/GCE | 0.2 M PBS, pH 4.0 | DPV | 0.027 | 50-500 | (f) |
| $TiO_2$-Pt/CNT/GCE | 0.1 M PBS, pH 7.0 | Amperometry | 0.1 | 0.5-100 | (g) |
| MWCNT-NFMIP/DGLPE | 0.1 M PBS pH 2.0 | DPCSV | 0.02 | 0.08-10 | (h) |
| RGO-GCE | 0.1 M PBS, pH 5.5 | DPV | 100 | 450-4950 | (i) |

TABLE 3-continued

Performance Comparison of Different Modified Electrode with GPE in the Presence of AgNO$_3$ for Methionine Determination.

| Transducer | Medium | Technique | LOD (μM) | Linear Range (μM) | Ref†† |
|---|---|---|---|---|---|
| Ag-Au (BMNp)/GCE | 0.1 M PBS, pH 7.0 | LSV & ch-Amp | 30 | 50-500 | (j) |
| Bare DGLPE | 0.1 M NaOH, AgNO$_3$ | CLSV & Amp | 0.42 | 10-500 | This work |

Abbreviations:
Ru: Ruthenium (II);
Metden: Metallodendrimer;
CAu: Colloidal Gold;
Cystm: Cysteamine;
Ni-P/CCE: Nickel Powder Doped Carbon Ceramic Electrode;
SPGME: Screen Printed Graphite Macroelectrode;
p-4α-Cu$^{II}$TAPc: 1,8,15,22-tetraaminophthalocyanato-copper(II);
NFMIP: Nano film molecular Imprinted;
BMNp: Bimetallic Nanoparticle;
CNT: Carbon Nanotube;
MWCNT: Multiple wall Carbon Nanotube;
RGO: reduced graphene;
CtCE: Conducting Composite Electrode;
DGLPE: Renewable Graphite Lead Pencil Electrode;
GCE: glassy Carbon Electrode;
CLSV: Cathodic Linear Scan Voltammetry;
DPV: Differential Pulse voltammetry;
Ch-Amp: Chronoamperometry.
††Table 3 References:
(a) S. D. Holmstrom, J. A. Cox, Electrocatalysis at a conducting composite electrode doped with a ruthenium(II) metallodendrimer, Anal. Chem. 72 (2000) 3191-3195;
(b) L. Agüí, J. Manso, P. Yáñez-Sedeño, J. M. Pingarrón, Colloidal-gold cysteamine-modified carbon paste electrodes as suitable electrode materials for the electrochemical determination of sulphur-containing compounds: Application to the determination of methionine, Talanta 64 (2004) 1041-1047;
(c) A. Salami, et al.;
(d) W. T. Tan, J. K. Goh, Electrochemical oxidation of methionine mediated by a fullerene-C 60 modified gold electrode, Electroanal. 20 (2008) 2447-2453;
(e) M. Gómez-Mingot, J. Iniesta, V. Montiel, R. O. Kadara, C. E. Banks, Direct oxidation of methionine at screen printed graphite macroelectrodes: Towards rapid sensing platforms, Sens. Actuators, B 155 (2011) 831-836;
(f) A. J. Jeevagan, et al.;
(g) F. Chekin, et al.;
(h) B. B. Prasad, et at.;
(i) D. Zhang, et al.;
(j) M. Murugavelu, et al., each incorporated herein by reference in their entirety.

Figure 16A:
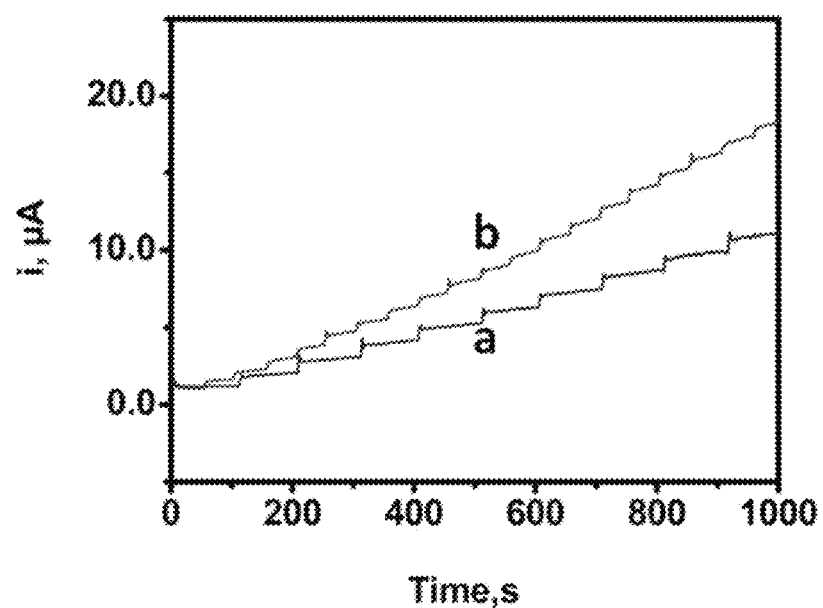
FIG. 16A shows amperometry studies of a GPE in 0.10 M NaOH pH 13.70±0.20 with 3.00 ppm $AgNO_3$ at 0.65 V and with (a) 9 additions of 20 μM DL-methionine at 100 s intervals or (b) 19 additions of 20 μM DL-methionine at 50 s intervals.

Amperometric Response and Interference Studies Amperometric response of the developed sensor to successive additions of 20 μM methionine at 0.65 V at different time interval is shown in FIG. 16A. Sensitivity of the sensor to effective oxidation of methionine shows clear response for 9 consecutive additions of 20 μM at 100 s interval ((a) in FIG. 16A). However the ability of the transducer to respond to a higher range of concentrations was also demonstrated for 19 consecutive addition of 20 μM methionine at 50 s intervals ((b) in FIG. 16A). This result shows that the developed method can be utilized for both voltammetric and amperometric techniques in the determination of methionine.

Figure 16B:
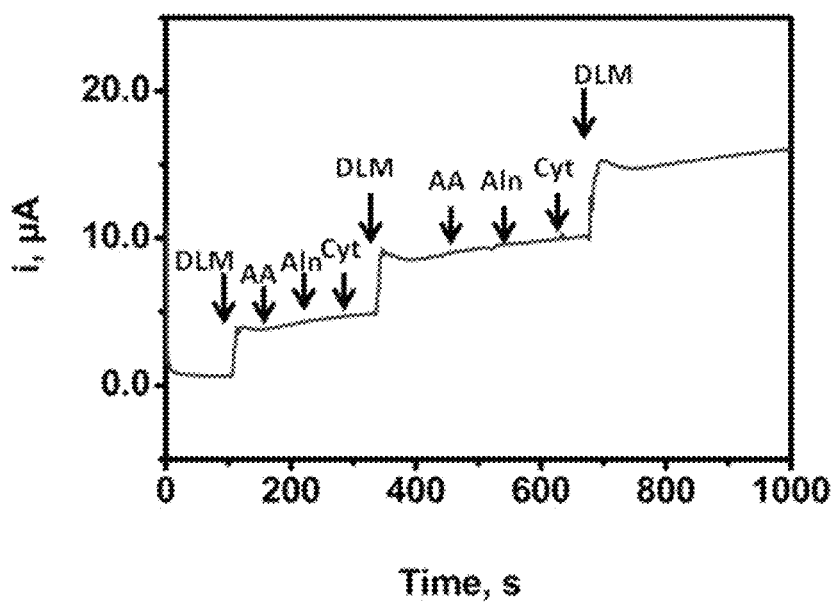
FIG. 16B shows amperometry studies of a GPE in 0.10 M NaOH pH 13.70±0.20 with 3.00 ppm $AgNO_3$ at 0.65 V and with repeated serial additions of 0.10 mM DL-methionine (DLM), 20 μM ascorbic acid (AA), 20 μM alanine (Aln), and 20 μM cysteine (Cyt).

Interference studies of methionine with ascorbic acid (AA), L-alanine (Aln) and cysteine (Cyt), which are representative of essential vitamins and amino acids that can co-exist with methionine in human serum, were investigated with the amperometric measurement technique at the same 0.65 V (FIG. 16B). Addition of 100 μM methionine (DLM) shows a very sharp response in the amperogram at about 120 s but no response can be observed for the consecutive spiking of 20 μM AA, An, and Cyt. However, a very Rood response indicating the selectivity of methionine can also be observed when another 100 μM was added at about 380 s. interference compounds added for the second periods between 400 s and 700 s again show no amperometric response by interference and further confirm the selectivity of the sensor to methionine detection. Ability of the sensor to be sensitive to methionine after a series of interference compounds being added twice was proved by its third response to a third methionine addition after 700 s.

Application of the Developed Technique on Serum Sample

Figure 17A:
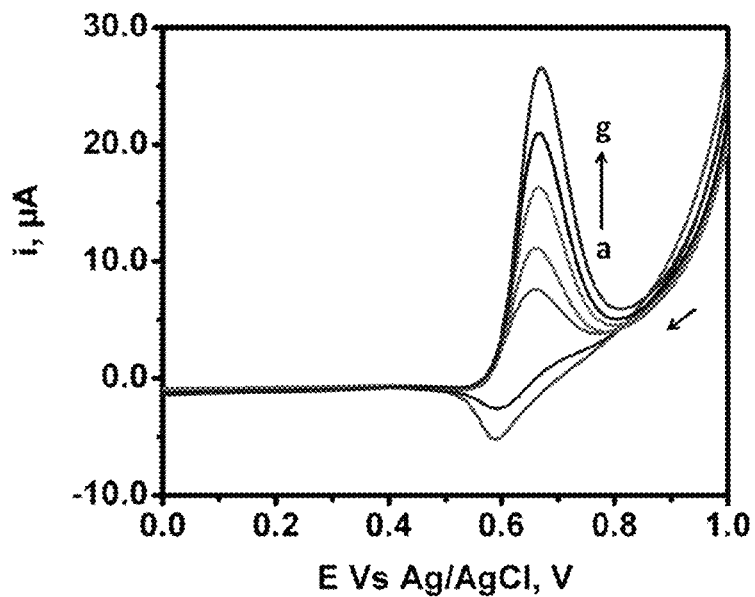
FIG. 17A shows CSLSVs of GPE in 0.10 M NaOH pH 13.70±0.20 and 3 ppm $AgNO_3$ with (a) nothing added (blank), (b) 50 μL serum added, (c) 0.05 mM, (d) 0.10 mM, (e) 0.15 mM, (f) 0.20 mM, or (g) 0.25 mM methionine added.
Figure 17B:
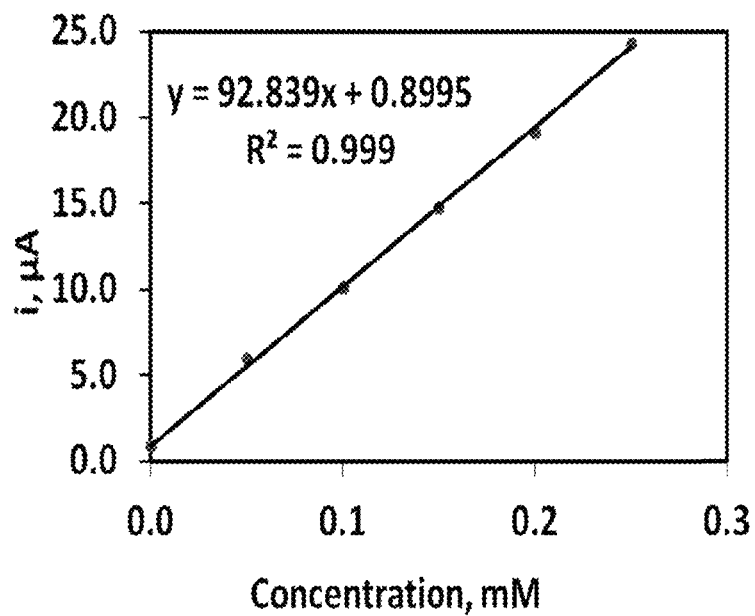
FIG. 17B shows a corresponding calibration curve of the data shown in FIG. 17A.

Methionine concentration was analyzed by a standard addition method using a sample obtained from a healthy patient at the King Fand University Teaching Hospital. The sample was treated to remove protein, and 50 μL was spiked in the 0.1 M NaOH to make a 100 s dilution of the serum. A good response of the serum on GPE can be observed in (b) of FIG. 17A at about 0.65 V, corresponding to DLM signal in the serum sample when compared with (a), representing the blank voltammogram. Successive addition of 0.05 mM methionine standard solution give a remarkable response observed from (c) to (g) of FIG. 17A for 0.05-0.25 mM of methionine (hose analysis is enumerated in Table 4. About 9.69 μM, corresponding to ~0.97 mM concentration of methionine in the serum sample was detected with a good recovery range between 98-109%. This result indicates a high concentration of methionine in the serum sample of the patient. In this instance, a medical professional should guide a patient to MRD along with regular methionine evaluation to prevent the consequences excess methionine metabolism. Performance of the developed technique on this serum sample is an indication of its capability for real life applications.

A proficient and cost effective electrochemical method by in-situ single-step AgO modification of a graphite pencil electrode (GPE) and determination of serum methionine have been successfully developed and characterized. Electro-catalytic activity of Ag in 0.10 M NaOH pH 13.70±0.20 in the presence of $AgNO_3$ was used to initiate the oxidation reaction of methionine on GPE surface by a $Ag^{2+}$ metal-induced reaction by hydroxyl radical ($OH^-$) readily available mechanism. Other supporting electrolytes explored (0.10 M PBS pH 7.00±0.20) could not initiate oxidation of methionine. Electrode linearity dependence obtained is given as $i=(\mu A)=73.314C_{DLM}+1.1459$ for a linear range concentration of 10 μM-500 μM with correlation coefficient ($R^2$) of 0.9927 and limit of detection of 0.42 μM. Effects of potential interferences such as ascorbic acid (AA), L-alanine (Aln) and cysteine was found to be insignificant. Developed method was found to be suitable fur both voltammetric and amperometric techniques for the development of non-enzymatic sensor for methionine and its real life application on human serum sample by standard addition method with correlation coefficient ($R^2$) of 0.999, The developed method is also suitable in the presence of potential interferences such as ascorbic acid, L-alanine, and cysteine.

TABLE 2

Methionine Detection in Healthy Human Serum Sample

| # | Spiked Amount (mM) | Amount Found (mM) | Amount Recovered (μM) | % Recovery |
|---|---|---|---|---|
| 1 | 0.05 | 0.055 | 9.69 | 109.88 |
| 2 | 0.10 | 0.099 | 9.69 | 99.32 |
| 3 | 0.15 | 0.149 | 9.69 | 99.38 |
| 4 | 0.20 | 0.197 | 9.69 | 98.34 |
| 5 | 0.25 | 0.252 | 9.69 | 100.99 |

The invention claimed is:

1. A method of measuring a concentration of an analyte in an aqueous sample, the method comprising:
   immersing a graphite electrode, a reference electrode, and a counter electrode in the aqueous sample;
   measuring a current response at a voltage of 0.4-0.8 V; and
   determining the concentration of the analyte in the aqueous sample by comparing the current response to a correlation chart,
   wherein the analyte is glucose or methionine at a concentration of 1.0 μM-10.0 mM,
   wherein the aqueous sample comprises an inorganic base at a concentration of 0.02-1.0 M and a metal salt at a concentration of 0.1-10 ppm,
   wherein the metal salt comprises at least one metal ion selected from the group consisting of $Cu^{2+}$, $Ag^+$, $Ni^{2+}$, $Co^{2+}$, $Co^{3+}$, $Zn^{2+}$, $Sn^{2+}$, $Pb^{2+}$, $Fe^{2+}$, $Fe^{3+}$, $Cr^{2+}$, and $Cr^{3+}$.

2. The method of claim 1, wherein the inorganic base is NaOH, and the aqueous sample has a pH of 12.0-14.0.

3. The method of claim 1, wherein the graphite electrode has no surface modification prior to the immersing.

4. The method of claim 1, wherein the graphite electrode has a diameter or width of 0.1-2.0 mm and a length of 3.0-20.0 mm in contact with the aqueous sample after the immersing.

5. The method of claim 1, wherein the aqueous sample further comprises at least one selected from the group consisting of ascorbic acid, alanine, fructose, uric acid, and cysteine, each independently at a concentration of 0.01-1.00 mM.

6. The method of claim 1, wherein the reference electrode is an Ag/AgCl electrode, and the counter electrode comprises platinum.

7. The method of claim 1, further comprising removing a precipitated protein from the aqueous sample prior to the immersing, wherein the aqueous sample further comprises serum.

8. The method of claim 7, wherein the removing comprises mixing an alcohol with the serum at a volume ratio of 1:4-4:1 to produce the precipitated protein, and centrifuging the precipitated protein.

9. The method of claim 7, wherein the serum is derived from a human donor.

10. The method of claim 1, wherein the measuring involves applying linear scan voltammetry to the aqueous sample.

11. The method of claim 1, further comprising constructing a calibration curve from a current response of two or more standard solutions.

12. The method of claim 1, wherein the analyte is glucose, and
   wherein the metal salt comprises $Cu^{2+}$, the $Cu^{2+}$ having a concentration of 1-5 ppm in the aqueous sample.

13. The method of claim 12, wherein the glucose is present in the aqueous sample at a concentration of 0.06-4.0 mM.

14. The method of claim 12, wherein the voltage is 0.60-0.65 V.

15. The method of claim 12, wherein the metal salt is $Cu(NO_3)_2$.

16. The method of claim 1, wherein the analyte is methionine, and
   wherein the metal salt comprises $Ag^+$, the $Ag^+$ having a concentration of 2-6 ppm in the aqueous sample.

17. The method of claim 16, wherein the methionine is present in the aqueous sample at a concentration of 0.01-0.50 mM.

18. The method of claim 16, wherein the voltage is 0.63-0.67 V.

19. The method of claim 16, wherein the metal salt is $AgNO_3$.

20. The method of claim 16, wherein the measuring produces silver oxide nanoparticles on the graphite electrode.

* * * * *